US012054768B2

(12) United States Patent
Robinson et al.

(10) Patent No.: US 12,054,768 B2
(45) Date of Patent: *Aug. 6, 2024

(54) METHODS FOR DETECTING AGGLUTINATION AND COMPOSITIONS FOR USE IN PRACTICING THE SAME

(71) Applicant: The Regents of the University of California, Oakland, CA (US)

(72) Inventors: Peter Robinson, Berkeley, CA (US); Cheng-Ting Tsai, Berkeley, CA (US); Carolyn Bertozzi, Stanford, CA (US)

(73) Assignee: The Regents of the University of California, Oakland, CA (US)

( * ) Notice: Subject to any disclaimer, the term of this patent is extended or adjusted under 35 U.S.C. 154(b) by 360 days.

This patent is subject to a terminal disclaimer.

(21) Appl. No.: 17/474,424

(22) Filed: Sep. 14, 2021

(65) Prior Publication Data

US 2021/0403978 A1 Dec. 30, 2021

Related U.S. Application Data

(63) Continuation of application No. 15/566,594, filed as application No. PCT/US2016/027906 on Apr. 15, 2016, now Pat. No. 11,149,296.

(60) Provisional application No. 62/149,324, filed on Apr. 17, 2015.

(51) Int. Cl.
*C12Q 1/6804* (2018.01)
*C12Q 1/6806* (2018.01)
*C12Q 1/686* (2018.01)
*G01N 33/543* (2006.01)

(52) U.S. Cl.
CPC ......... *C12Q 1/6804* (2013.01); *C12Q 1/6806* (2013.01); *C12Q 1/686* (2013.01); *G01N 33/54306* (2013.01); *C12Q 2525/117* (2013.01); *C12Q 2525/155* (2013.01); *C12Q 2525/197* (2013.01); *C12Q 2531/113* (2013.01)

(58) Field of Classification Search
None
See application file for complete search history.

(56) References Cited

U.S. PATENT DOCUMENTS

| | | |
|---|---|---|
| 4,292,403 A | 9/1981 | Duermeyer |
| 7,198,900 B2 | 4/2007 | Woudenberg et al. |
| 7,666,598 B2 | 2/2010 | Piepenburg et al. |
| 7,932,060 B2 | 4/2011 | Nadeau et al. |
| 8,114,962 B2 | 2/2012 | Weininger et al. |
| 8,673,567 B2 | 3/2014 | Wang et al. |
| 8,993,347 B2 | 3/2015 | Reisacher |
| 2002/0051986 A1 | 5/2002 | Baez et al. |
| 2005/0003361 A1 | 1/2005 | Fredriksson |
| 2005/0009050 A1 | 1/2005 | Nadeau et al. |
| 2005/0233351 A1 | 10/2005 | Landegren |
| 2007/0281367 A1 | 12/2007 | Hennessy et al. |
| 2009/0162840 A1 | 6/2009 | Fredriksson et al. |
| 2014/0194311 A1 | 7/2014 | Gullberg et al. |

FOREIGN PATENT DOCUMENTS

| | | |
|---|---|---|
| CN | 101410530 A | 4/2009 |
| WO | WO 1992/001814 | 2/1992 |
| WO | WO 2001/061037 A1 | 8/2001 |
| WO | WO 2004/094456 | 11/2004 |
| WO | WO 2005/074417 A2 | 8/2005 |
| WO | WO 2008/066483 A1 | 6/2008 |
| WO | WO 2011/062933 A2 | 5/2011 |
| WO | WO 2013/073932 A1 | 5/2013 |

OTHER PUBLICATIONS

Agaylan, et al.; "A Highly Sensitive Particle Agglutination Assay for the Detection of P53 Autoantibodies in Patients With Lung Cancer"; Cancer; vol. 110, No. 11, pp. 2502-2506 (Dec. 1, 2007).
Attar, et al.; "Medical conditions associated with a positive anti-double-stranded deoxyribonucleic acid"; Saudi Med J.; vol. 31, No. 7, pp. 781-787 (Jul. 2010).
Chen, et al.; "Rapid Detection of Hepatitis B Virus Surface Antigen by an Agglutination Assay Mediated by a Bispecific Diabody against Both Human Erythrocytes and Hepatitis B Virus Surface Antigen"; Clinical and Vaccine Immunology; vol. 14, No. 6, pp. 720-725 (Jun. 2007).
Damoiseaux, et al.; "Autoantibodies 2015: From diagnostic biomarkers toward prediction, prognosis and prevention"; Autoimmunity Reviews; vol. 14, pp. 555-563 (2015).
Gajadhar, et al.; "A proximity ligation assay using transiently transfected, epitope-tagged proteins: application for in situ detection of dimerized receptor tyrosine kinases"; Biotechniques; vol. 48, No. 2, pp. 145-152 (Feb. 2010).
Gajadhar, et al.; "In Situ Analysis of Mutant EGFRs Prevalent in Glioblastoma Multiforme Reveals Aberrant Dimerization, Activation, and Differential Response to Anti-EGFR Targeted Therapy"; Molecular Cancer Research; vol. 10, No. 3, pp. 428-440 (Mar. 2012).
Gupta, et al.; "Whole-Blood Agglutination Assay for On-Site Detection of Human Immunodeficiency Virus Infection"; Journal of Clinical Microbiology; vol. 41, No. 7, pp. 2814-2821 (Jul. 2003).
Gurtler; "Difficulties and strategies of HIV diagnosis"; The Lancet; vol. 348, pp. 176-179 (1996).
Gustafsdottir, et al.; "In vitro analysis of DNA-protein interactions by proximity ligation"; PNAS; vol. 104, No. 9, pp. 3067-3072 (Feb. 27, 2007).

(Continued)

*Primary Examiner* — Samuel C Woolwine
(74) *Attorney, Agent, or Firm* — BOZICEVIC, FIELD & FRANCIS LLP; James J. Diehl

(57) ABSTRACT

Methods are provided for detecting antigen binding agents in samples. Aspects of the methods include detection of the aggregation of antigen binding agents with polynucleotide-bound antigens by sensitive proximity-based association of the antigen-bound polynucleotides. Aspects of the methods also include methods for the detection of such proximity-based association through nucleic acid amplification. In addition, compositions, e.g., reagents, kits, and devices, useful in practicing various embodiments of the methods are provided.

22 Claims, 23 Drawing Sheets

Specification includes a Sequence Listing.

(56) References Cited

OTHER PUBLICATIONS

Janssen, et al.; "Nucleic Acids for Ultra-Sensitive Protein Detection"; Sensors; vol. 13, pp. 1353-1384 (2013).
Karp, et al.; "A serological assay to detect SARS-CoV-2 antibodies in at-home collected finger-prick dried blood spots"; MedRixiv; 13 pages (Jun. 3, 2020).
Leslie, et al.; "Autoantibodies as predictors of disease"; The Journal of Clinical Investigation; vol. 108, No. 10, pp. 1417-1422 (Nov. 2001).
Leuchowius, et al.; "Parallel visualization of multiple protein complexes in individual cells in tumor tissue"; Molecular & Cellular Proteomics; vol. 12, No. 6, 1563-1571 (Jun. 2013).
Lundberg, et al.; "Multiplexed Homogeneous Proximity Ligation Assays for High-throughput Protein Biomarker Research in Serological Material"; Molecular & Cellular Proteomics; vol. 10, No. 4, 38 pages (2011).
Molina-Bolivar, et al.; "Comprehensive Review: Latex Immunoagglutination Assays"; Journal of Macromolecular Science Part C—Polymer Reviews; vol. 45, pp. 59-98 (2005).
Rouquette, et al.; "Detection of antibodies to dsDNA: an overview of laboratory assays"; Lupus; vol. 15, pp. 403-407 (2006).
Tsai, et al.; "Ultrasensitive Antibody Detection by Agglutination-PCR (ADAP)"; ACS Central Science; vol. 2, pp. 139-147 (2016).
Virella; "Chapter 8: Antigen-Antibody Reactions, in Medical Immunology"; pp. 119-133 (2001).
Virella; "Chapter 12: The Humoral Immune Response and Its induction by Active Immunization, in Medical Immunology"; pp. 225-243 2001).
Zaenker, et al.; "Serologic Autoantibodies as Diagnostic Cancer Biomarkers—A Review"; Cancer Epidemiol Biomarkers Prev.; vol. 22, No. 12, pp. 2161-2181 (Dec. 2013).
Tsai, et al.; "Antibody detection by agglutination-PCR (ADAP) enables early diagnosis of HIV infection by oral fluid analysis"; PNAS; vol. 115, No. 6, pp. 1250-1255 (Feb. 6, 2018).

FIG. 10

| Antibody | Sequence | Diluent | Detection limit | |
|---|---|---|---|---|
| | | | ng/ml | attomoles |
| Biotin | 4 | buffer | 0.89 ±0.39 | 12 ±5 |
| Biotin | 4 | serum | 3.7 ±2 | 49 ±27 |
| Biotin | 1 | buffer | 0.072 ±0.008 | 0.96 ±0.11 |
| | | | | |
| Mouse IgG | 4 | buffer | 1.9 ±0.6 | 25 ±8 |
| Mouse IgG | 4 | serum | 2.3 ±0.3 | 31 ±4 |
| Mouse IgG | 2 | buffer | 0.096 ±0.023 | 1.3 ±0.3 |
| Mouse IgG | 2 | serum | 0.060 ±0.008 | 0.8 ±0.1 |
| | | | | |
| GFP pAb | 4 | buffer | 2.0 ±1.1 | 27 ±15 |
| GFP pAb | 4 | serum | 1.7 ±0.6 | 23 ±8 |
| GFP mAb | 4 | Bugger | 0.16 ±0.05 | 2.1 ±0.7 |
| GFP mAb | 4 | cell culture media | 0.12 ±0.05 | 1.6 ±0.7 |
| | | | | |
| Insulin | 2 | buffer | 0.39±0.48 | 4.3 ±5.3 |
| Insulin | ELISA | buffer | 6.7±1.9 | 3722 ±1056 |
| Insulin | 2 | serum | 0.015±0.004 | 0.17 ±0.04 |
| Insulin | 2 | saliva | 11±3 | 122 ±33 |
| | | | | |
| DNP | 4 | antisera | 9400±2100 | N/A |

METHODS FOR DETECTING AGGLUTINATION AND COMPOSITIONS FOR USE IN PRACTICING THE SAME

CROSS-REFERENCE

This application is a continuation of U.S. patent application Ser. No. 15/566,594, filed, Oct. 13, 2017, which is a national stage application under 35 U.S.C. § 371 of PCT/US2016/027906, filed Apr. 15, 2016, which claims the benefit of U.S. Provisional Patent Application No. 62/149,324, filed Apr. 17, 2015, which applications are incorporated herein by reference in their entirety.

STATEMENT REGARDING FEDERALLY SPONSORED RESEARCH

This invention was made with government support under Grant No. GM059907 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-284WO_SeqList_ST25.txt" created on Apr. 15, 2016 and having a size of 4 KB. The contents of the text file are incorporated by reference herein in their entirety.

INTRODUCTION

Of the many biomolecule detection assays methods available, those based on particle agglutination, including latex particle agglutination, continue to be widely used in research biology and human and veterinary medicine, particularly for the detection of antibodies in a fluid test sample. Agglutination assay procedures have advantages of being simple, widely applicable, and nonhazardous. Agglutination assays are also generally rapid, producing results in a short time. Despite these advantages, agglutination assays are typically overlooked for analytical purposes in favor of enzyme-linked immunosorbent assays (ELISA) due to the poor detection limits and/or requirements for large sample volumes in agglutination assays.

SUMMARY

Methods are provided for detecting antigen binding agents in samples. Aspects of the methods include detection of the aggregation of antigen binding agents with polynucleotide-bound antigens by sensitive proximity-based association of the antigen-bound polynucleotides. Aspects of the methods also include methods for the detection of such proximity-based association through nucleic acid amplification. In addition, compositions, e.g., reagents, kits, and devices, useful in practicing various embodiments of the methods are provided.

Aspects of the instant disclosure include a method of detecting an antigen-binding agent in a sample, the method comprising: a) contacting the sample with a first molecule of an antigen conjugated to a first polynucleotide and a second molecule of an antigen conjugated to a second polynucleotide under conditions sufficient to form a complex comprising the antigen binding agent bound to the first and second molecules; b) binding the first polynucleotide and the second polynucleotide of the complex to form an amplicon; c) amplifying the amplicon to generate an amplification product; and d) detecting the amplification product, wherein detection of the amplification product provides for detection of the antigen binding agent. In some cases, the antigen of the first molecule and the antigen of the second molecule are the same. In some cases, the antigen binding agent is an antibody, e.g., an immunoglobulin A (IgA), an immunoglobulin D (IgD), an immunoglobulin E (IgE), an immunoglobulin G (IgG) or an immunoglobulin M (IgM). In some cases, the antigen is a polypeptide. In some cases, the binding comprises hybridizing a bridging polynucleotide to the first polynucleotide and the second polynucleotide. In some cases, the binding comprises hybridization of a nucleotide sequence of the first polynucleotide to a complementary nucleotide sequence of the second polynucleotide. In some cases, the complementary nucleotide sequences of the first and second polynucleotides are at least 6 nucleotides in length. In some cases, the binding comprises ligating the first polynucleotide and the second polynucleotide. In some cases, the method further comprises contacting the sample with a splint polynucleotide and the binding comprises ligating the split polynucleotide to the first polynucleotide or the second polynucleotide or both the first and second polynucleotides. In some cases, the first polynucleotide, second polynucleotide, and bridging polynucleotide are DNA polynucleotides and the ligating comprises contacting the sample with a DNA ligase. In some cases, the method comprises hybridizing a bridging polynucleotide to the first polynucleotide and the second polynucleotide, ligating the first polynucleotide and the second polynucleotide following the hybridizing and specifically degrading the bridging polynucleotide following the ligating. In some cases, the bridging polynucleotide comprises one or more nucleoside analogs and the degrading comprises base excision of the one or more nucleoside analogs mediated by contacting the sample with one or more base excision reagents. In some cases, the one or more base excision reagents comprise a glycosylase, an endonuclease, or a combination thereof. In some cases, the one or more nucleoside analogs comprise deoxyribouracil. In some cases, the amplifying comprises polymerase chain reaction (PCR) amplification. In some cases, the amplifying comprises isothermal amplification. In some cases, the detecting comprises measuring the amount of the antigen binding agent in the sample based on quantifying the amplification product. In some cases, the amplifying comprises quantitative PCR. In some cases, the method detects the presence of the antigen binding agent in the sample at a concentration of less than 15 ng/mL. In some cases, the method detects the presence of the antigen binding agent in the sample at a concentration of less than 100 pg/mL. In some cases, the sample is obtained from a subject suspected of having anti-polynucleotide antibodies. In some cases, the sample is obtained from a subject suspected of having a condition. In some cases, the condition comprises an infection. In some cases, the condition comprises an autoimmune disorder or an inflammatory disorder. In some cases, the condition comprises an immune response to a neoplasm. In some cases, the condition is a paraneoplastic syndrome. In some cases, the neoplasm is a cancer selected from the group consisting of prostate cancer, breast cancer, lung cancer, colon cancer, stomach cancer, liver cancer and thyroid cancer. In some cases, the condition comprises a metabolic disease. In some cases, the metabolic disease is diabetes. In some cases, the sample is a tissue sample. In some cases, the tissue sample is a blood sample. In some cases, the blood sample is a serum sample. In some cases, the sample is an excreted bodily fluid or semi-solid. In some cases, the excreted bodily fluid or semi-solid is selected from the group consisting of: urine, saliva, tears, sweat, pus and stool. In some cases, the sample is derived from a cell configured to produce the antigen binding agent. In some cases, the cell is a hybridoma and the antigen binding agent is an antibody produced by the hybridoma. In some cases, the sample is derived from a laboratory animal configured to produce the antigen binding agent. In some cases, the sample is a blood sample. In some cases, the blood sample is a serum sample. In some cases, the sample is an excreted bodily fluid or semi-solid. In some cases, the excreted bodily fluid or semi-solid is selected from the group consisting of: urine, saliva, tears, sweat, pus and stool. In some cases, the contacting further comprises contacting the sample with free DNA. In some cases, the first molecule of antigen and the first polynucleotide and the second molecule of antigen and the second polynucleotide are both conjugated with molar ratios of antigen to polynucleotide between 1:1 and 1:4.

Aspects of the instant disclosure include a kit for the detection of an antigen binding agent, the kit comprising: a) a first antigen, conjugated to a first polynucleotide, that specifically binds to the antigen binding agent at a first antigen binding site of the antigen binding agent; and b) a second antigen, conjugated to a second polynucleotide, that specifically binds to the antigen binding agent at a second antigen binding site of the antigen binding agent. In some cases, the kit further comprises a bridging polynucleotide the specifically hybridizes to the first and second polynucleotides. In some cases, the first polynucleotide comprises a nucleotide sequence that is complementary to a nucleotide sequence of the second polynucleotide. In some cases, the kit further comprises a splint polynucleotide that specifically hybridizes to one or more of the first polynucleotide, the second polynucleotide or the bridging polynucleotide. In some cases, the first antigen and the second antigen are the same. In some cases, the kit further comprises a ligase. In some cases, the kit further comprises one or more amplification reagents. In some cases, kit components are present in a single container. In some cases, kit components are present in separate containers.

Aspects of the instant disclosure include a library for multiplexed detection of antigen-binding agents, the library comprising: a) a plurality of antigen pairs, each antigen pair comprising two of the same antigen each conjugated to a polynucleotide comprising a unique primer binding site; and b) a plurality of primer pairs, each primer pair comprising complementary sequence to the unique primer binding sites of an antigen pair, wherein, upon binding of the antigen pairs to antigen-binding agents, the polynucleotides of the antigen pairs form amplicons that can be specifically amplified by the primer pairs thereby allowing multiplexed detection of the antigen-binding agents. In some cases, the antigens of the plurality of antigen pairs comprise autoimmune disease antigens. In some cases, the antigens of the plurality of antigen pairs comprise cancer antigens. In some cases, the antigens of the plurality of antigen pairs comprise pathogen antigens. In some cases, the polynucleotides of each antigen pair comprise complementary sequence to one another. In some cases, the polynucleotides of each antigen pair each comprise sequence complementary to a bridging polynucleotide. In some cases, the plurality of antigen pairs are in a single container. In some cases, each primer pair of the plurality of primer pairs are present in a separate container or separate well of a multi-well plate.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 10 provides Table 1.

DEFINITIONS

Figure 1:
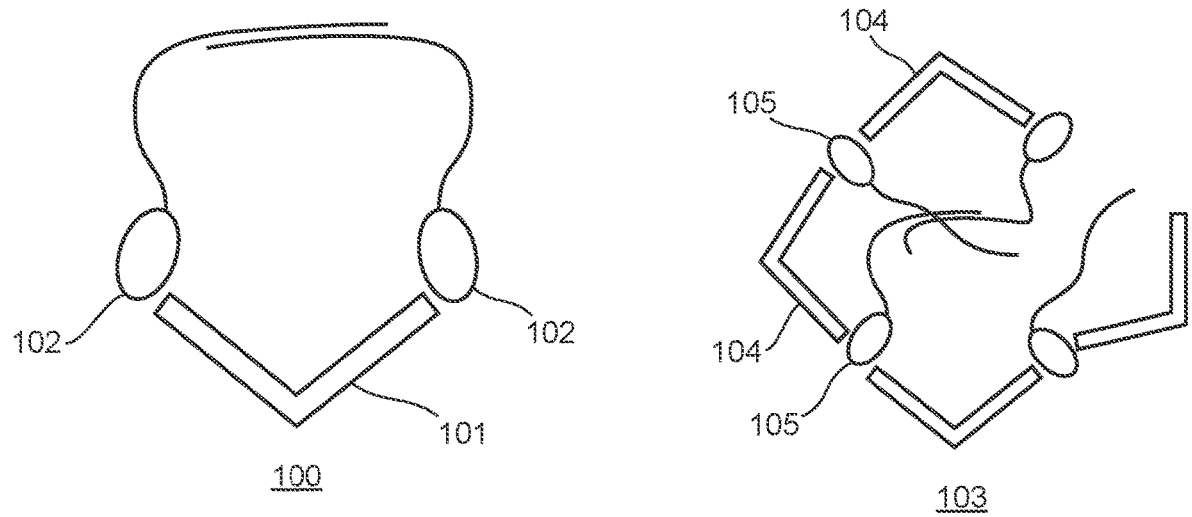
FIG. 1 depicts embodiments of agglutinated antigen and antigen binding agents.

The terms "agglutination" and "aggregation" are used interchangeably and, as used herein, refer to the joining together of antigens and antigen binding agents into a complex where the complex includes more than one antigen and one antigen binding agent. In general agglutination makes use of multivalent antigen binding agents or antigen binding agents that bind more than one molecule of antigen. Multivalent antigen binding agents may facilitate the aggregation of many antigens and antigen binding agents into a complex. In agglutination, antigens may be monovalent or multivalent. In certain embodiments, agglutination is achieved through the use of monovalent antigens and multivalent antigen binding agents. In certain embodiments, agglutination is achieved through the use of monovalent antigens and bivalent antigen binding agents. In certain embodiments, agglutination is achieved through the use of multivalent antigen binding agents that bind multivalent antigens. In certain embodiments, agglutination is achieved through the use of bivalent antigen binding agents that bind multivalent antigens. In certain embodiments, agglutination is achieved through the use of multivalent antigen binding agents that bind bivalent antigens. In certain embodiments, agglutination is achieved through the use of bivalent antigen binding agents that bind bivalent antigens. As used herein, the components of an aggregated complex may be held in close proximity such that the components are able to associate and/or interact. In some instances, certain components of a reaction mixture, due to specifics of their interaction and/or their relative concentration in the reaction mixture, may only have a significant likelihood of interaction, e.g., interaction necessary for detection of agglutination, when held in close proximity within an aggregated complex.

The term "antigen" as used herein refers to any naturally occurring or synthetic immunogenic substance. Immunogenic substances include those that are foreign and those that are naturally occurring within the body of an organism. As such, the introduction of a foreign immunogenic substance may induce an organism to generate a general or specific immune response to the foreign immunogenic substance. In other instances, the production of an immunogenic substance within the body of an organism may induce the organism to generate a specific or general autoimmune response to the native immunogenic substance. Antigens, as used herein, encompass but are not limited to chemicals, small molecules, biomolecules (e.g., nucleic acids), macromolecules, peptides, polypeptides, cell fragments, cells, unicellular organisms, multicellular organisms, fragments thereof, and combinations thereof. In some instances, antigens may be antigens for which an agent that binds the antigen is known, e.g., a polypeptide for which an antibody that binds the polypeptide is known. In some instances, antigens may be antigens for which an agent that binds the antigen is unknown, e.g., a polypeptide for which an antibody that binds the polypeptide is unknown. For example, the use of polypeptides and peptides, both naturally occurring and synthetic, as antigens to which antibodies may be raised has been described in, e.g., *Methods in Molecular Biology: Immunochemical Protocols*. Ed. Burns, R., Humana Press, 2005, the disclosure of which is incorporated herein by reference in its entirety.

The terms "polypeptide" and "protein" and "peptide" are used interchangeably to refer to a polymer of amino acid residues linked by peptide bonds, and for the purposes of the instant disclosure, may have a minimum length of at least 8 amino acids. Oligopeptides, oligomers multimers, and the like, typically refer to longer chains of amino acids and are also composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 8 amino acids are encompassed by the definition. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

The terms "antibody" and "immunoglobulin", as used herein, are used interchangeably may generally refer to whole or intact molecules or fragments thereof and modified and/or conjugated antibodies or fragments thereof that have been modified and/or conjugated. The immunoglobulins can be divided into five different classes, based on differences in the amino acid sequences in the constant region of the heavy chains. All immunoglobulins within a given class will have very similar heavy chain constant regions. These differences can be detected by sequence studies or more commonly by serological means (i.e. by the use of antibodies directed to these differences). Immunoglobulin classes include IgG (Gamma heavy chains), IgM (Mu heavy chains), IgA (Alpha heavy chains), IgD (Delta heavy chains), and IgE (Epsilon heavy chains).

Antibody or immunoglobulin may refer to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized, see for instance *Fundamental Immunology* Ch. 7 (Paul, W., ed., 2nd ed.

Raven Press, N.Y. (1989)). Briefly, each heavy chain typically is comprised of a heavy chain variable region (abbreviated as $V_H$) and a heavy chain constant region (abbreviated as $C_H$). The heavy chain constant region typically is comprised of three domains, $C_H1$, $C_H2$, and $C_H3$. Each light chain typically is comprised of a light chain variable region (abbreviated as $V_L$) and a light chain constant region (abbreviated herein as $C_L$). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs).

Whole or largely intact antibodies are generally multivalent, meaning they may simultaneously bind more than one molecule of antigen whereas antibody fragments may be monovalent. Antibodies produced by an organism as part of an immune response are generally monospecific, meaning they generally bind a single species of antigen. Multivalent monospecific antibodies, i.e. antibodies that bind more than one molecule of a single species of antigen, may bind a single antigen epitope (e.g., a monoclonal antibody) or multiple different antigen epitopes (e.g., a polyclonal antibody).

Multispecific (e.g., bispecific) antibodies, which bind multiple species of antigen, may be readily engineered by those of ordinary skill in the art and, thus, may be encompassed within the use of the term "antibody" used herein where appropriate. Also, multivalent antibody fragments may be engineered, e.g., by the linking of two monovalent antibody fragments. As such, bivalent and/or multivalent antibody fragments may be encompassed within the use of the term "antibody", where appropriate, as the ordinary skilled artisan will be readily aware of antibody fragments, e.g., those described below, which may be linked in any convenient and appropriate combination to generate multivalent monospecific or polyspecific (e.g., bispecific) antibody fragments.

Antibody fragments include but are not limited to antigen-binding fragments (Fab or F(ab), including Fab' or F(ab'), (Fab)$_2$, F(ab')$_2$, etc.), single chain variable fragments (scFv or Fv), "third generation" (3G) molecules, etc. which are capable of binding the epitopic determinant. These antibody fragments retain some ability to selectively bind to the subject antigen, examples of which include, but are not limited to:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab)$_2$, the fragment of the antibody that can be obtained by treating whole antibody with the enzyme pepsin without subsequent reduction;

(4) F(ab)$_2$ is a dimer of two Fab' fragments held together by two disulfide bonds;

(5) Fv, defined as a genetically engineered fragment containing the variable region of the light chain and the variable region of the heavy chain expressed as two chains;

(6) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, tetrabodies, etc. which may or may not be polyspecific (see, for example, WO 94/07921 and WO 98/44001) and (7) "3G", including single domain (typically a variable heavy domain devoid of a light chain) and "miniaturized" antibody molecules (typically a full-sized Ab or mAb in which non-essential domains have been removed).

The term "recombinant", as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide, means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. The terms also include such molecules with modifications, such as by methylation and/or by capping, and unmodified forms of a polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing non-nucleotidic backbones, polymers, and other synthetic sequence-specific nucleic acid polymers providing that the polymers contain nucleobases in a configuration which allows for base pairing and base stacking, such as is found in DNA and RNA. Polynucleotides also encompass those containing one or more "nucleoside analogs" or "nucleotide analogs", which are nucleoside or nucleotide analogs of naturally occurring nucleosides and nucleotides as in e.g., RNA and DNA. Non-limiting examples of nucleoside analogs and reagents used in the synthesis or modification of nucleoside analogs include but are not limited to e.g., 1,3,9-Trimethylxanthine; 1,3-Dimethyluric acid; 1,N6-Etheno-2'-deoxyadenosine; 1,N6-Ethenoadenine; 1-Allyl-3,7-dimethyl-8-phenylxanthine; 1-Allyl-3,7-dimethyl-8-sulfophenylxanthine; 1-Cyclohexyluracil; 1-Methylthymine; 1-Methyluric acid; 2,3'-Anhydrothymidine; 2',3',5'-Tri-O-acetyladenosine; 2',3',5'-Tri-O-acetylcytidine hydrochloride; 2',3',5'-Tri-O-acetyluridine; 2',3',5'-Tri-O-benzoyluridine; 2',3'-Dideoxy-5-iodouridine; 2',3'-Dideoxyadenosine; 2',3'-Di-O-benzoyluridine; 2',3'-O-Isopropylidene-6-mercaptopurine riboside; 2',3'-O-Isopropylideneguanosine; 2',3'-O-Isopropylideneuridine; 2'-Deoxyadenosine monohydrate; 2'-Deoxycytidine; 2'-Deoxycytidylyl(3'→5')-2'-deoxyguanosine; 2'-Deoxyguanosine monohydrate; 2'-Deoxyinosine; 2'-Deoxyuridine; 2'-O-Methyladenosine; 2'-O-Methylcytidine; 2-Amino-6-chloropurine riboside; 2-Amino-6-methylmercaptopurine; 2-Aminopurine; 2-Chloro-2'-deoxyadenosine antileukemic; 2-Chloro-N6-cyclopentyladenosine adenosine receptor agonist; 2-Dimethylamino-6-hydroxypurine; 2-Mercaptopurine; 2-Thiouracil; 3'-Deoxyguanosine; 3'-O-Methyluridine; 3-Methyladenine; 3-Methyluracil; 4,5,6-Triaminopyrimidine sulfate; 4-Amino-1,3-dimethyl-2,6-dioxy-5-nitrosopyrimidine; 4-Amino-5-carboxy-2-ethylmercaptopyrimidine; 4-Chlorouracil; 4-Methylumbelliferyl β-L-fucoside glycosidase substrate; 4-Thiouridine; 5,6-Dihydrodeoxyuridine; 5'-(4-Fluorosulfonylbenzoyl)adenosine hydrochloride; 5'-Amino-5'-deoxythymidine; 5'-Deoxy-5'-(methylthio)adenosine; 5'-Deoxyadenosine methylthioadenosine/S-adenosylhomocysteine (MTA/SAH) nucleosidase substrate; 5'-O-(4,4'-Dimethoxytrityl)-2'-deoxyuridine; 5'-O-Tritylthymidine; 5-Carbethoxyuracil; 5-Carboxy-2-thiouracil; 5-Chloro-2'-deoxyuridine thymidine analog; 5-Ethyl-2'-deoxyuridine; 5-Fluoro-1-(tetrahydro-2-furyl) uracil; 5-Fluorouridine; 5-Iodo-2,4-dimethoxy-pyrimidine; 5-Iodo-2'-deoxycytidine; 5-Iodocytosine; 5-Methoxyuridine; 5-Methyl-2-thiouridine; 5-Methylcytidine; 5-Methylcytosine hydrochloride; 5-Methyluridine; 5-n-Propyluracil; 5-Propyl-2-thiouracil; 5-Sulfaminouracil; 6-(Dimethylamino)purine; 6-Azauracil; 6-Azauridine; 6-Chloropurine riboside; 6-Cyanopurine; 6-Ethoxypurine; 6-Ethylmercaptopurine; 6-Mercaptopurine-2'-deoxyriboside; 6-Methylmercaptopurine riboside; 6-Methylpurine; 6-n-Butoxypurine; 6-n-Heptylmercaptopurine crystalline; 6-n-Propoxypurine; 6-Phenyl-2-thiouracil; 6-Propyl-2-thiouracil; 6-Selenopurine; 7-Methylguanosine; 8-(3-Carboxypropyl)-1,3-dimethylxanthine; 8-Bromo-2',3',5'-tri-O-acetylguanosine; 8-Bromoadenosine; 9-(2',3',5'-Tri-O-benzyl-β-D-arabinofuranosyl)adenine; 9-Ethylguanine; 9-Methyluric acid; Adefovir dipivoxil; Allopurinol riboside; Bromonucleic acid; Glycitein; Guanosine; Guanylyl(2'→5) adenosine; Guanylyl(3'→5)cytidine; Guanylyl(3'→5')uridine; Hypoxanthine; Indoxyl β-D-glucoside; Isocytosine; Isoxanthopterin; Kinetin riboside; N2-Isobutyryl-3'-O-benzoyl-2'-deoxyguanosine; N2-Isobutyryl-5'-O-(4,4'-dimethoxytrityl)-2'-deoxyguanosine; N2-Isobutyryl-5'-O-(4,4'-dimethoxytrityl)-2'-deoxyguanosine 3'-O-succinic acid; N2-Methylguanosine; N4-Acetylcytidine; N4-Aminocytidine; N4-Anisoylcytidine; N4-Benzoyl-5'-O-(4,4'-dimethoxytrityl)-2'-deoxycytidine; N4-Octadecylcytosine β-D-arabinofuranoside; N6-Benzoyladenine; N6-Methyl-2'-deoxyadenosine; N6-Phenoxyacetyl-5'-O-(4,4'-dimethoxytrityl)-2'-deoxyadenosine; Orotic acid potassium salt; Orotidine; Oxypurinol; R(−)-PD 128,908 hydrochloride; S-(2-Hydroxy-5-nitrobenzyl)-6-thioguanosine; S-(2-Hydroxy-5-nitrobenzyl)-6-thioinosine; Se-(p-Nitrobenzyl)-6-selenoinosine; Thymidylyl(3'→5')-2'-deoxyadenosine; Thymidylyl(3'→5')thymidine; Thymine 1-β-D-arabinofuranoside; Trifluorothymidine; Uracil 1-β-D-arabinofuranoside; Zeatin riboside; and the like.

The terms "polynucleotide-bound antigen" and "antigen-bound polynucleotide" are used interchangeably herein and generally refer to a polynucleotide, as described herein, bound to an antigen, as described herein, in such a manner as the polynucleotide and antigen are unlikely or are known not to disassociate under the expected reaction conditions and/or any other relevant conditions the polynucleotide-bound antigen are likely to be subjected to. Such a polynucleotide and an antigen may be bound by any convenient or appropriate method of binding a polynucleotide and an antigen including direct binding, e.g., covalent binding, and indirect binding, e.g., through the use of a linker molecule or other mediator of polynucleotide-antigen binding.

The term "amplicon" as used herein refers to a nucleic acid complex that is the source of an amplified nucleic acid or the initiating nucleic acid in a nucleic acid amplification reaction. A "nucleic acid complex" refers to two or more joined nucleic acids including but not limited to e.g., a duplex, a triplex, a quadruplex, a pentaplex, a hexaplex, and the like. The nucleic acids of a nucleic acid complex may be joined, e.g., hybridized, through hydrogen bonding interactions including Watson-Crick base-pairing. In some instances, two or more nucleic acids of a nucleic acid complex may be ligated together through the covalent linking of two ends of individual nucleic acid molecules, e.g., through the use of an enzyme that catalyzes the covalent joining of nucleic acids or ligases. In an amplification reaction additional amplification product may be amplified from amplification product that is the result of the initial amplicon and, as such, the term amplicon may also refer to the product of an amplification reaction which is subsequently used in further amplification, however, as used herein, an amplicon generally refers to the initial polynucleotide or polynucleotide complex from which amplification is initiated.

The term "ligase" as referred to herein refers collectively to enzymes that catalyze the covalent joining of two adjacent ends of a nucleic acid molecule or molecules. For example, a nucleic acid ligase may catalyze the formation of a phosphodiester bond between juxtaposed 5' phosphate and 3' hydroxyl termini in single stranded or double stranded nucleic acid, including, e.g., single-stranded DNA (ssDNA), double-stranded DNA (dsDNA), single-stranded RNA (ssRNA), and double-stranded RNA (dsRNA). Ligases may ligate nucleic acid hybridized to a complementary nucleic acid or may ligate in the absence of a complementary nucleic acid. Any convenient ligase may find use in the methods described herein including but not limited to, e.g., naturally occurring ligases, synthetic or recombinant ligases, mutant ligases, DNA ligases, RNA ligases, sticky-end ligases, blunt end ligases, nick-repair ligases, thermostable ligases, thermolabile ligases, T4 DNA ligase, T3 DNA ligase, T7 DNA ligase, *E. coli* DNA ligase, Taq DNA ligase, *Thermococcus* DNA ligase, *Chlorella* virus DNA Ligase, T4 RNA ligase 1, T4 RNA ligase 2, *Methanobacterium thermoautotrophicum* DNA/RNA ligase, and the like.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with their use in synthesis of primer extension products, and may be in the range of between 8 to 100 nucleotides in length, such as 10 to 75, 15 to 60, 15 to 40, 18 to 30, 20 to 40, 21 to 50, 22 to 45, 25 to 40, and so on, including in the range of between 18-40, 20-35, 21-30 nucleotides long, and any length between the stated ranges. In some instances, primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

The terms "hybridize" and "hybridization" refer to the formation of complexes between nucleotide sequences which are sufficiently complementary to form complexes via Watson-Crick base pairing. For example, where a primer "hybridizes" with target (template), such complexes (or hybrids) are sufficiently stable to serve the priming function required by, e.g., the DNA polymerase to initiate DNA synthesis.

Two nucleotide sequences are "complementary" to one another or have "complementarity" when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel or reverse-complement sense wherein a complementary region of a first sequence in the 5' to 3' orientation binds to its complementary sequence in the 3' to 5' orientation relative to the second and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary". Usually two sequences are sufficiently complementary when at least about 85% of the nucleotides share base pair organization over a defined length of the molecule, including but not limited to in some instances at least about 90%, at least about 95%, at least about 96%, at least about 97%, at least about 98%, at least about 99%, and 100% base pair organization over a defined length of the molecule.

The term "stringent conditions" refers to conditions under which a primer will hybridize preferentially to, or specifically bind to, its complementary binding partner, and to a lesser extent to, or not at all to, other sequences. In some instances, where polynucleotides are bound to one another through hybridization, conditions sufficient to allow such hybridization may include stringent conditions.

By "specifically binds" or "selectively bind" is meant that the molecule binds preferentially to the target of interest or binds with greater affinity to the target than to other molecules. For example, a DNA molecule will bind to a substantially complementary sequence and not to unrelated sequences. Specific binding may refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antigen" includes a plurality of such antigens and reference to "the antigen" includes reference to one or more antigens and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Methods

As summarized above, embodiments of the instant disclosure are directed to methods of detecting the presence of an antigen binding agent in a sample through the aggregation of antigen binding agents with polynucleotide bound-antigen into a complex. Aspects of the methods include proximity-based association of the polynucleotides of the aggregated antigens of the complex and subsequent detection of such association.

Antigens and Antigen Binding Agents

Aspects of the methods include the use of polynucleotide bound antigens for the detection of antigen binding agents. As used herein, by "antigen binding agent" is meant any agent that specifically binds to an antigen and, for the purposes of the described methods, is capable of mediating agglutination and/or aggregation of antigen and antigen binding agent into a complex. In some instances, referring for example to FIG. 1, a complex of antigen and antigen binding agent (100) may comprise, at a minimum, a single molecule of antigen binding agent (101) bound to two molecules of antigen (102). As such, an antigen binding agent, as used herein, may refer to biomolecules that simultaneously bind to at least two molecules of a single antigen and/or biomolecules that simultaneously bind to at least two molecules of different antigens. In some instances, a complex of antigen and antigen binding agent (103) may include at least two molecules of antigen binding agent (104) due to the ability of an antigen (105) to simultaneously bind two or more molecules of antigen binding agent.

Accordingly, antigen binding agents of the subject methods may include two or more antigen binding sites. Such pluralities of antigen binding sites may have specificity for a single antigen or specificity for multiple different antigens. Antigens of the subject methods may include two or more antigen binding agent binding sites. Such pluralities of antigen binding agent binding sites may have specificity for a single antigen binding agent or specificity for multiple different antigen binding agents. Such multiplicity of binding interactions facilities complex formation and the aggregation of antigens and antigen binding agents into close proximity.

In some instances, an antigen binding agent may be an antibody or multivalent antibody fragment that binds to two or more molecules of antigen to mediate agglutination and formation of an antigen-antibody complex. In some instances, an antigen to which a multivalent or bivalent antibody binds will be a bivalent or multivalent antigen such that agglutination is mediated by binding of each antibody to two or more antigens and binding of each antigen to two or more antibodies. As such, antibody-antigen complexes may include a single antibody bound to two molecules of antigen and/or a plurality of antibodies bound to two or more antigens which are each bound to two or more antibodies. As described herein, antibodies may be monospecific or multispecific and, as such, antibody-antigen complexes may include those comprising a single species of antigen and those comprising two or more species of antigens. In some instances, an antibody is bispecific such that each antibody is bound to two different molecules of different antigens to mediate agglutination. As such, bispecific antibody-antigen complexes may include a single bispecific antibody bound to two molecules of two different antigens and/or a plurality of bispecific antibodies bound to two molecules of two different antigens which are each bound to two or more antibodies. An ordinary skilled artisan will readily understand the various multiplicities of interactions possible by the above described components of agglutination complexes as set forth herein. Such complexes, wherein agglutination is mediated by the presence of antibody in the sample, position the antibody-bound antigens in close proximity, e.g., as compared to unbound antigen.

An antigen of the subject methods will include at least one polynucleotide attached to the antigen. The polynucleotide may be attached to the antigen via any convenient method, as described in more detail below. Polynucleotides attached to an antigen of interest will vary depending, in part, on the detection method employed, the method of attachment of the antigen to the polynucleotide, the specific antigen binding agent(s) to be detected, etc. The length of antigen-bound polynucleotides of the subject disclosure will vary and be 15 or more nucleotides and may range from 15 nucleotides to 200 nucleotides or more including but not limited to e.g., 20 or more nucleotides, 25 or more nucleotides, 30 or more nucleotides, 35 or more nucleotides, 40 or more nucleotides, 45 or more nucleotides, 50 or more nucleotides, 55 or more nucleotides, 60 or more nucleotides, 65 or more nucleotides, 70 or more nucleotides, 75 or more nucleotides, 80 or more nucleotides, 90 or more nucleotides, 95 or more nucleotides, 100 or more nucleotides, 15 to 200 nucleotides, 20 to 200 nucleotides, 25 to 200 nucleotides, 30 to 200 nucleotides, 35 to 200 nucleotides, 40 to 200 nucleotides, 45 to 200 nucleotides, 50 to 200 nucleotides, 15 to 100 nucleotides, 20 to 100 nucleotides, 25 to 100 nucleotides, 30 to 100 nucleotides, 35 to 100 nucleotides, 40 to 100 nucleotides, 45 to 100 nucleotides, 50 to 100 nucleotides, etc.

Polynucleotides of the subject disclosure will comprise at least one region of complementarity that binds at least one other polynucleotide and facilitates the formation of a polynucleotide complex (e.g., duplex, triplex, etc.) with other polynucleotides as described. According to the described methods, without being bound by theory, polynucleotide complex formation, through complementary hydrogen bonding, is facilitated by increasing the probability of complementary polynucleotide-to-polynucleotide binding by increasing the time at least two of the complex-forming polynucleotides are in proximity with each other. Such increased time of proximity of the polynucleotide complex forming polynucleotides is achieved through antigen binding agent-mediated aggregation of antigen-bound polynucleotides.

In one embodiment, a first polynucleotide bound to an antigen may include a region of complementarity that is complementary to a second polynucleotide that is also bound to an antigen, including the same antigen or a different antigen. In some instances, the region of complementarity between the first and second polynucleotides is sufficient for hybridization of the two polynucleotides. In certain instances, hybridization between the first and second antigen-bound polynucleotides is sufficiently weak that hybridization essentially does not occur in the absence of complex formation.

In another embodiment, a first polynucleotide bound to an antigen may include a region of complementarity that is complementary to a polynucleotide that is not bound to an antigen, including e.g., a bridging polynucleotide or a splint polynucleotide as described herein. In some instances, a first polynucleotide bound to an antigen may include essentially no regions of significant complementarity to a second antigen-bound polynucleotide such that the first polynucleotide and the second polynucleotide essentially do not hybridize to one another.

Although in many instances, a particular polynucleotide may have of complementarity to only one other polynucleotide, i.e., a second antigen-bound polynucleotide or an polynucleotide that is not bound to an antigen, such polynucleotides need not be so limited and may in some instances may have complementarity to two or more different polynucleotides. For example, in certain embodiments, a first polynucleotide bound to an antigen may include multiple regions of complementary including e.g., a first region of complementarity to a second antigen-bound polynucleotide and a second region of complementarity to a polynucleotide that is not bound to an antigen. In many instances, polynucleotides that are not bound to an antigen will have complementarity to two or more different polynucleotides, including e.g., two or more antigen-bound polynucleotides, two or more antigen-bound polynucleotides and a second polynucleotide that this not bound to an antigen, etc.

Regions of complementarity between two polynucleotides of the subject disclosure will vary and may be 6 or more contiguous base pairs and range from 6 contiguous base pairs to 50 contiguous base pairs or more, including but not limited to e.g., 6 to 50 contiguous base pairs, 6 to 45 contiguous base pairs, 6 to 40 contiguous base pairs, 6 to 35 contiguous base pairs, 6 to 30 contiguous base pairs, 6 to 25 contiguous base pairs, 6 to 20 contiguous base pairs, 6 to 15 contiguous base pairs, 6 to 10 contiguous base pairs, 10 to 50 contiguous base pairs, 10 to 45 contiguous base pairs, 10 to 40 contiguous base pairs, 10 to 35 contiguous base pairs, 10 to 30 contiguous base pairs, 10 to 25 contiguous base pairs, 10 to 20 contiguous base pairs, 10 to 15 contiguous base pairs, 7 or more contiguous base pairs, 8 or more contiguous base pairs, 9 or more contiguous base pairs, 10 or more contiguous base pairs, 11 or more contiguous base pairs, 12 or more contiguous base pairs, 13 or more contiguous base pairs, 14 or more contiguous base pairs, 15 or more contiguous base pairs, 16 or more contiguous base pairs, 17 or more contiguous base pairs, 18 or more contiguous base pairs, 19 or more contiguous base pairs, 20 or more contiguous base pairs, 6 contiguous base pairs, 7 contiguous base pairs, 8 contiguous base pairs, 9 contiguous base pairs, 10 contiguous base pairs, 11 contiguous base pairs, 12 contiguous base pairs, 13 contiguous base pairs, 14 contiguous base pairs, 15 contiguous base pairs, 16 contiguous base pairs, 17 contiguous base pairs, 18 contiguous base pairs, 19 contiguous base pairs, 20 contiguous base pairs, 21 contiguous base pairs, 22 contiguous base pairs, 23 contiguous base pairs, 24 contiguous base pairs, 25 contiguous base pairs, etc.

According to aspects of the instant methods, the polynucleotide employed may be single or double stranded, including partially or completely single or double stranded, and may or may not comprise a primer binding site. In some instances, a first polynucleotide will comprise one half of an amplicon such that, when held in sufficient proximity with a second polynucleotide, comprising the other half of the amplicon, the first and second polynucleotides together comprise a complete amplicon. In some instances, the first and/or second polynucleotide may comprise less than half of one amplicon such that one or more additional polynucleotides may be necessary to complete the amplicon even when the first and second polynucleotides are in sufficient proximity to associate. In some instances, a reaction, e.g., a chemical reaction or enzymatic reaction, may be utilized to join two or more polynucleotides of a complex, formed according to the methods described herein, to generate a single polynucleotide that comprises an amplicon or a portion of an amplicon.

Figure 2:
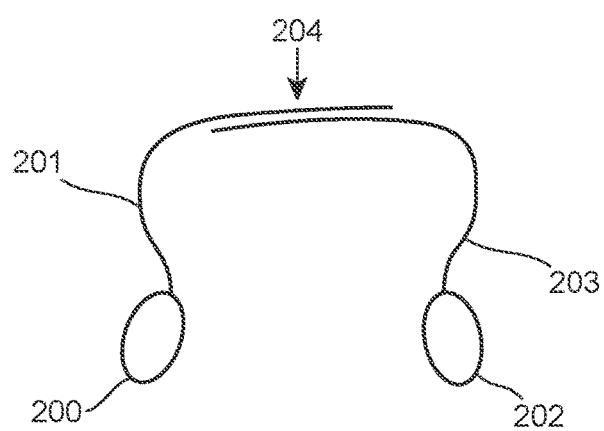
FIG. 2 depicts an embodiment of a polynucleotide duplex formed by proximity association of polynucleotide-bound antigens.

Referring now to the non-limiting embodiment presented in FIG. 2. In some instances, a first polynucleotide (201) attached to first antigen (200) is sufficient to form an amplicon with a second polynucleotide (203) attached to a second antigen (202) when held in relative proximity by formation of a complex that includes the first and second antigens (200 and 202) and one or more antigen binding members. The first and second polynucleotides (201 and 203), containing at least some complementary nucleic acid sequence, bind through sufficient hydrogen bonding interactions to form a nucleic acid duplex (204) that may serve as the initiation point of elongation of one of the polynucleotides.

Figure 3:
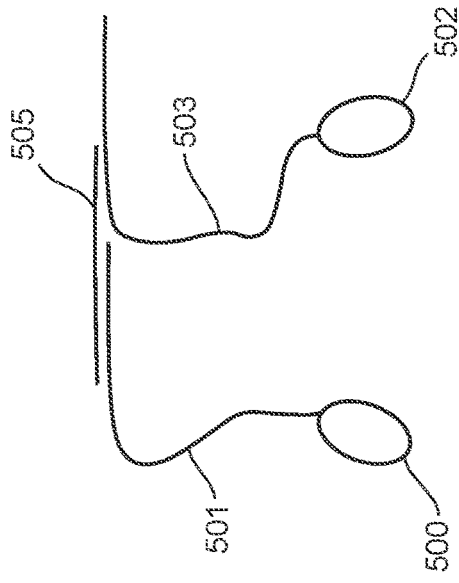
FIG. 3 depicts an embodiment of a polynucleotide complex formed by proximity association of polynucleotide-bound antigens and a bridging polynucleotide.
Figure 4:
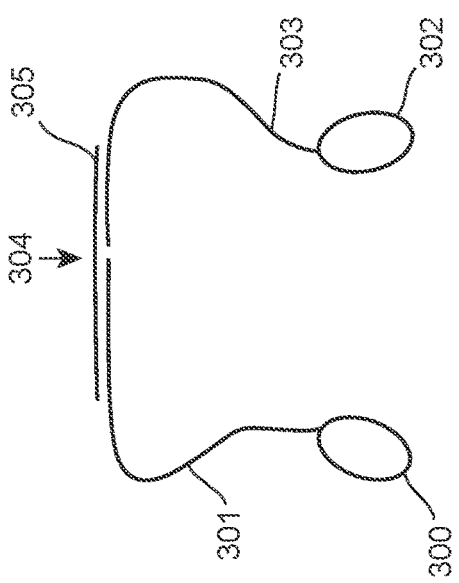
FIG. 4 depicts an embodiment of a polynucleotide complex formed by proximity association of polynucleotide-bound antigens, a bridging polynucleotide, and a splint polynucleotide.

Referring now to the non-limiting example presented in FIG. 3. In some instances, a first polynucleotide (301) attached to first antigen (300) is sufficient to form an amplicon with a second polynucleotide (303) attached to a second antigen (302) and a bridging polynucleotide (305) when the first and second polynucleotides (301 and 303) are held in relative proximity by formation of a complex that includes the first and second antigens (300 and 302) and one or more antigen binding members. The first and second polynucleotides (301 and 303), both containing at least some complementary nucleic acid sequence with the bridging polynucleotide (305), bind the bridging polynucleotide through sufficient hydrogen bonding interactions to form a nucleic acid complex (304) that may serve as the initiation point of elongation of one of the polynucleotides. Optionally, the first and second polynucleotides (301 and 303) may be ligated to form a continuous polynucleotide that may serve as an amplicon, e.g., with the addition of one or more primers or with use of the bridging polynucleotide as a primer. In another embodiment (see FIG. 4), the first and second polynucleotides (401 and 403) are ligated to a splint polynucleotide (406) that has complementarity to the bridging polynucleotide (405).

The polynucleotide may be attached to a desired antigen at any convenient point along the length of the polynucleotide, including at the 3' or 5' termini. In some instances, the first antigen-bound polynucleotide of an amplicon is attached to the antigen at its 3' end and the second antigen-bound polynucleotide of the amplicon is attached to the antigen at its 5' end. In some instances, both the first and second antigen-bound polynucleotides are attached to their respective antigens at their 3' ends. In some instances, both the first and second antigen-bound polynucleotides are attached to their respective antigens at their 5' ends.

Figure 5:
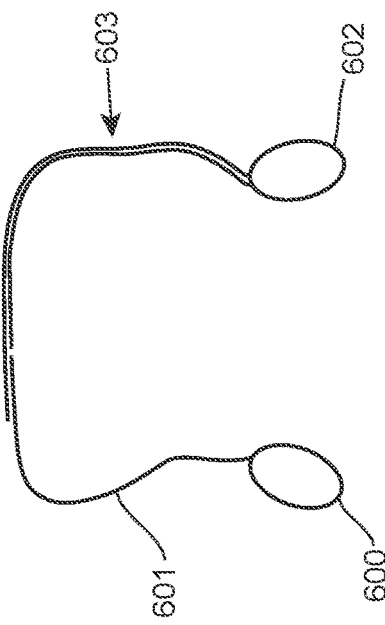
FIG. 5 depicts an embodiment of a polynucleotide complex formed by proximity association of polynucleotide-bound antigens and a bridging polynucleotide.

In another embodiment (see FIG. 5), both the first and second antigen-bound polynucleotides (501 and 503) are attached to their respective antigens (500 and 502) at their 5' or 3' ends and bind a bridging polynucleotide (505) to form a nucleic acid complex from which elongation may be initiated.

As used herein, the term "bridging polynucleotide" refers to any polynucleotide that joins two or more separate polynucleotides or two termini of a single polynucleotide by simultaneously hybridizing with complementary regions on each polynucleotide or complementary regions of the polynucleotide termini. In certain instances, a bridging polynucleotide joins two antigen-bound polynucleotides by simultaneously hybridizing with a first complementary region of a first antigen-bound polynucleotide and a second complementary region of a second antigen-bound polynucleotide. Bridging polynucleotides may be partially or completely single stranded, including partially single stranded and partially double stranded. The length of bridging polynucleotides of the subject disclosure will vary and may be 10 or more nucleotides and range from 10 to 100 or more nucleotides, including e.g., 10 to 100 nucleotides, 12 to 100 nucleotides, 14 to 100 nucleotides, 16 to 100 nucleotides, 18 to 100 nucleotides, 20 to 100 nucleotides, 22 to 100 nucleotides, 24 to 100 nucleotides, 26 to 100 nucleotides, 28 to 100 nucleotides, 30 to 100 nucleotides, 10 to 50 nucleotides, 12 to 50 nucleotides, 14 to 50 nucleotides, 16 to 50 nucleotides, 18 to 50 nucleotides, 20 to 50 nucleotides, 22 to 50 nucleotides, 24 to 50 nucleotides, 26 to 50 nucleotides, 28 to 50 nucleotides, 30 to 50 nucleotides, 10 to 40 nucleotides, 12 to 40 nucleotides, 14 to 40 nucleotides, 16 to 40 nucleotides, 18 to 40 nucleotides, 20 to 40 nucleotides, 22 to 40 nucleotides, 24 to 40 nucleotides, 26 to 40 nucleotides, 28 to 40 nucleotides, 30 to 40 nucleotides, 10 to 30 nucleotides, 12 to 30 nucleotides, 14 to 30 nucleotides, 16 to 30 nucleotides, 18 to 30 nucleotides, 20 to 30 nucleotides, 12 or more nucleotides, 13 or more nucleotides, 14 or more nucleotides, 15 or more nucleotides, 16 or more nucleotides, 17 or more nucleotides, 18 or more nucleotides, 19 or more nucleotides, 20 or more nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, etc.

Bridging polynucleotides may "bridge" two or more polynucleotides to form a polynucleotide complex. In some instances, a bridging polynucleotide may hybridize with two polynucleotide termini, including termini of the same or different nucleic acids, such that the termini are adjacent within the polynucleotide complex, e.g., allowing for the ligation of the adjacent termini. In some instances, a bridging polynucleotide may hybridize with two polynucleotide termini, including termini of the same or different nucleic acids, such that the termini are not adjacent in the resulting polynucleotide complex, e.g., are not adjacent such that they cannot be directly ligated together. In some instances, e.g., where two termini of a polynucleotide complex are not adjacent, a splint polynucleotide may be hybridized in the space between the two termini such that the ends of the splint polynucleotide are located adjacent to one or more of the termini. The term "splint polynucleotide" as used herein refers to a polynucleotide, which may generally be single stranded or partially single stranded and partially double stranded, which may be used to fill one or more gaps between two polynucleotide termini of a polynucleotide complex, e.g., those complexes formed by use of a bridging polynucleotide. In some instances, a splint polynucleotide may have complementarity to one or more portions of a bridging polynucleotide. In some instances, the termini of one or more polynucleotides adjacent to a splint polynucleotide may be ligated to the splint polynucleotide.

In some instances, a bridging polynucleotide of the subject disclosure may include one or more nucleoside analogs. For example, in some instances, a bridging polynucleotide of the instant disclosure may include one or more deoxyribouracil (i.e., deoxyribose uracil, 2'-deoxyuridine, etc.) nucleosides/nucleotides. In certain instances, a bridging polynucleotide may include 2 or more nucleoside analogs including but not limited to e.g., 3 or more, 4 or more, 5 or more, 6 or more, etc. In some instances, the number of nucleoside analogs as a percentage of the total bases of the bridging polynucleotide is 1% or more, including but not limited to e.g., 2% or more, 3% or more, 4% or more, 5% or more, 6% or more, 7% or more, 8% or more, 9% or more, 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, etc.

In certain embodiments, methods of the instant disclosure may include the specific degradation of a bridging polynucleotide. For example, in some instances, the presence of a nucleoside analog within the bridging polynucleotide allows for the targeted degradation of the bridging polynucleotide, e.g., following ligation. In some instances, a bridging polynucleotide containing a nucleoside analog mediates specific degradation of the bridging polynucleotide through one or more base-excision mechanisms specific for the nucleoside analog. Such processes may make use of reagents for the specific excision of the particular nucleoside analog, e.g., by contacting the sample with one or more specific nucleoside excision reagents at a particular point in the method, e.g., following a ligation step. For example, a bridging polynucleotide, that includes one or more deoxyribouracils, hybridizes with and facilitates ligation of two antigen-bound polynucleotides then, following the ligation, the bridging polynucleotide is degraded e.g., through the use of one or more uracil-specific excision reagents.

Such specific excision reagents include those reagents that facilitate the specific excision of the particular nucleoside analog and/or facilitate the cleavage of one or more phosphodiester bonds abutting the particular nucleoside analog. As such, useful base excision reagents may include glycosylases and/or endonucleases. In certain embodiments, e.g., where one or more deoxyribouracils are incorporated into the bridging polynucleotide, useful uracil-specific excision reagents may include those reagents that facilitate the specific excision of uracil and/or facilitate the cleavage of one or more phosphodiester bonds abutting a uracil before or after uracil excision. Non-limiting examples, of uracil-specific excision reagents include but are not limited to e.g., uracil DNA glycosylase (UDG), Endonuclease IV, Endonuclease VIII, and the like. As such, in some instances, specifically degrading a nucleoside analog containing bridging polynucleotide may include contacting the sample with one or more base excision reagents.

Figure 6:
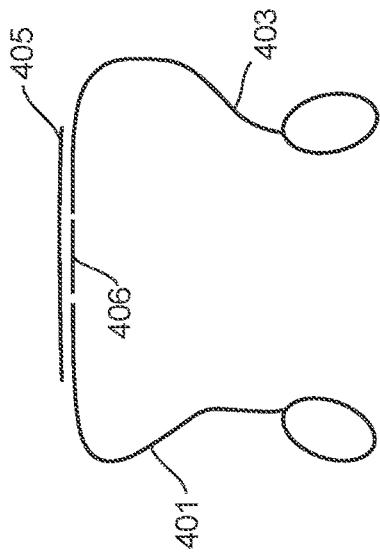
FIG. 6 depicts an embodiment of a polynucleotide complex that includes double-stranded polynucleotide, formed by proximity association of polynucleotide-bound antigens.

As described above, in some instances, one or more of the antigen-bound polynucleotides may be completely or partial double stranded. In one embodiment (see FIG. 6), a first antigen-bound polynucleotide (601) has sufficient complementarity to bind a second, partially double stranded, antigen-bound polynucleotide (603) to form a nucleic acid complex from which elongation may be initiated when the first and second antigens (600 and 602) form a complex with one or more molecules of antigen binding agent.

In some instances, the complementarity between a first antigen-bound polynucleotide and a second antigen-bound polynucleotide, and/or any bridging polynucleotide and/or splint polynucleotide, of the resulting complex is insufficient for significant formation of the polynucleotide complex in the absence of agglutination. For example, in some instances, the complementarity, including all complementarity of a particular complex or the complementarity of two or more components of the larger complex, is sufficiently inefficient such that complex formation necessary for downstream processes, e.g., ligation, elongation, amplification, etc., occurs essentially only when that polynucleotide-bound antigens are in close proximity due to being bound to one or more antigen binding agents in an agglutination complex.

In some instances, hybridization and polynucleotide complex formation, as described herein, is influenced by the concentrations of one or more reagents of the reaction mixture. For example, in some instances, the concentration of one or more components of the reaction mixture is sufficiently low such that the rate of formation of the polynucleotide complex in the absence of agglutination is significantly lower than the rate of formation of the polynucleotide complex within the agglutination complex. In some instances, the relative concentration of the polynucleotide-bound antigen is sufficiently low such that the rate of formation of the polynucleotide complex with free polynucleotide-bound antigen is significantly lower than the rate of formation of the polynucleotide complex with agglutinated polynucleotide-bound antigen. By "significantly lower" in this context is meant that the difference between the rates of formation of the polynucleotide complex between free and agglutinated components is sufficient such that an assay may be developed where the free and agglutinated states may be differentiated, e.g., using a particular detection method as described herein.

Amplification

Upon formation of an amplicon, or a joined polynucleotide from which an amplicon may be formed, or an elongated polynucleotide from which an amplicon may be formed, the amplicon may be amplified to generate an amplification product. Any convenient method of amplification may be utilized in generating the amplification product, as described in more detail below, and may depend upon the particular polynucleotide complex formed and/or particular requirements of the overall detection assay. As the formation of the amplicon is dependent on antigen binding agent-mediated aggregation of the polynucleotide bound-antigens, the presence of the amplification product may be indicative of the presence of the antigen binding agent and/or the amount of the antigen binding agent in the sample.

In some instances, amplification may be performed by polymerase chain reaction (PCR). In representative PCR amplification reactions, the reaction mixture generally includes a template nucleic acid which is combined with one or more primers that are employed in the primer extension reaction, e.g., the PCR primers (such as forward and reverse primers employed in geometric (or exponential) amplification or a single primer employed in a linear amplification). As such, in some instances, the hybridized portions of the above described nucleic acid complexes may serve as "primer" for the amplification reaction. For example, in instances where linear amplification is employed a single free 3'-terminus of hybridized nucleic acid of an above described nucleic acid complex may serve as a primer for amplification. In some instances, one or more additional nucleic acids may be added to serve as primer in a formed nucleic acid complex. For example, in some instances two antigen-bound polynucleotides may be joined in a ligation reaction and two additional primers may be added to facilitate amplification of the newly ligated nucleic acid segment or template. In some instances, a single free 3'-terminus of hybridized nucleic acid of an above described nucleic acid complex may serve as a first primer and a second primer may be added to facilitate amplification.

Any oligonucleotide primers with which the template nucleic acid (hereinafter referred to as template DNA for convenience) is contacted will be of sufficient length to provide for hybridization to complementary template DNA under annealing conditions. The primers will generally be at least 6 bp in length, including but not limited to e.g., at least 10 bp in length, at least 15 bp in length, at least 16 bp in length, at least 17 bp in length, at least 18 bp in length, at least 19 bp in length, at least 20 bp in length, at least 21 bp in length, at least 22 bp in length, at least 23 bp in length, at least 24 bp in length, at least 25 bp in length, at least 26 bp in length, at least 27 bp in length, at least 28 bp in length, at least 29 bp in length, at least 30 bp in length, and may be as long as 60 bp in length or longer, where the length of the primers will generally range from 18 to 50 bp in length, including but not limited to, e.g., from about 20 to 35 bp in length. In some instances, the template DNA may be contacted with a single primer or a set of two primers (forward and reverse primers), depending on whether primer extension, linear or exponential amplification of the template DNA is desired. Methods of PCR that may be employed in the subject methods include but are not limited to those described in U.S. Pat. Nos. 4,683,202; 4,683,195; 4,800,159; 4,965,188 and 5,512,462, the disclosures of which are herein incorporated by reference.

In addition to the above components, a PCR reaction mixture produced in the subject methods may include a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in *Proc. Natl. Acad. Sci USA* (1994) 91:2216-2220, the disclosure of which is incorporated herein by reference in its entirety); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) (e.g., as described in Perler et al., *Proc. Natl. Acad. Sci. USA* (1992) 89:5577, the disclosure of which is incorporated herein by reference in its entirety); *Pyrococcus* species GB-D (Deep Vent); *Pyrococcus furiosus* DNA polymerase (Pfu) (e.g., as described in Lundberg et al., Gene (1991) 108:1-6, the disclosure of which is incorporated herein by reference in its entirety), *Pyrococcus woesei* (Pwo) and the like. Generally, the reaction mixture will include four different types of dNTPs corresponding to the four naturally occurring bases are present, i.e. dATP, dTTP, dCTP and dGTP and in some instances may include one or more modified nucleotide dNTPs.

A PCR reaction will generally be carried out by cycling the reaction mixture between appropriate temperatures for annealing, elongation/extension, and denaturation for specific times. Such temperature and times will vary and will depend on the particular components of the reaction including, e.g., the polymerase and the primers as well as the expected length of the resulting PCR product. In some instances, e.g., where nested or two-step PCR are employed the cycling-reaction may be carried out in stages, e.g., cycling according to a first stage having a particular cycling program or using particular temperature(s) and subsequently cycling according to a second stage having a particular cycling program or using particular temperature(s).

Multistep PCR processes may or may not include that addition of one or more reagents following the initiation of amplification. For example, in some instances, amplification may be initiated by elongation with the use of a polymerase and, following an initial phase of the reaction, additional reagent(s) (e.g., one or more additional primers, additional enzymes, etc.) may be added to the reaction to facilitate a second phase of the reaction. In some instances, amplification may be initiated with a first primer or a first set of primers and, following an initial phase of the reaction, additional reagent(s) (e.g., one or more additional primers, additional enzymes, etc.) may be added to the reaction to facilitate a second phase of the reaction. In certain embodiments, the initial phase of amplification may be referred to as "preamplification".

In some instances, amplification may be carried out under isothermal conditions, e.g., by means of isothermal amplification. Methods of isothermal amplification generally make use of enzymatic means of separating DNA strands to facilitate amplification at constant temperature, such as, e.g., strand-displacing polymerase or a helicase, thus negating the need for thermocycling to denature DNA. Any convenient and appropriate means of isothermal amplification may be employed in the subject methods including but are not limited to: loop-mediated isothermal amplification (LAMP), strand displacement amplification (SDA), helicase-dependent amplification (HDA), nicking enzyme amplification reaction (NEAR), and the like. LAMP generally utilizes a plurality of primers, e.g., 4-6 primers, which may recognize a plurality of distinct regions, e.g., 6-8 distinct regions, of target DNA. Synthesis is generally initiated by a strand-displacing DNA polymerase with two of the primers forming loop structures to facilitate subsequent rounds of amplification. LAMP is rapid and sensitive. In addition, the magnesium pyrophosphate produced during the LAMP amplification reaction may, in some instances be visualized without the use of specialized equipment, e.g., by eye. SDA generally involves the use of a strand-displacing DNA polymerase (e.g., Bst DNA polymerase, Large (Klenow) Fragment polymerase, Klenow Fragment (3'-5' exo-), and the like) to initiate at nicks created by a strand-limited restriction endonuclease or nicking enzyme at a site contained in a primer. In SDA the nicking site is generally regenerated with each polymerase displacement step, resulting in exponential amplification. HDA generally employs: a helicase which unwinds double-stranded DNA unwinding to separate strands; primers, e.g., two primers, that may anneal to the unwound DNA; and a strand-displacing DNA polymerase for extension. NEAR generally involves a strand-displacing DNA polymerase that initiates elongation at a nicks, e.g., created by a nicking enzyme. NEAR is rapid and sensitive, quickly producing many short nucleic acids from a target sequence.

In some instances, entire amplification methods may be combined or aspects of various amplification methods may be recombined to generate a hybrid amplification method. For example, in some instances, aspects of PCR may be used, e.g., to generate the initial template or amplicon or first round or rounds of amplification, and an isothermal amplification method may be subsequently employed for further amplification. In some instances, an isothermal amplification method or aspects of an isothermal amplification method may be employed, followed by PCR for further amplification of the product of the isothermal amplification reaction. In some instances, a sample may be preamplified using a first method of amplification and may be further processed, including e.g., further amplified or analyzed, using a second method of amplification. As a non-limiting example, a sample may be preamplified by PCR and further analyzed by qPCR.

In some instances, the amplification step and the detection step, described below, may be combined, with or without the use of a preamplifcation step. In some instances, the particular amplification method employed allows for the qualitative detection of amplification product, e.g., by visual inspection of the amplification reaction with or without a detection reagent. In one embodiment, agglutinated antigen-bound polynucleotide are amplified by isothermal amplification, e.g., LAMP, and the amplification generates a visual change in the amplification reaction indicative of efficient amplification and thus presence of the antigen binding agent in the sample. In some instances, the amplification and detection steps are combined by monitoring the amplification reaction during amplification such as is performed in, e.g., real-time PCR, also referred to herein as quantitative PCR (qPCR), and described in more detail below.

In some instances, the methods described herein may make use of those methods, e.g., amplification methods, and components thereof, employed in proximity ligation assays (PLA) and proximity elongation assays (PEA) including but not limited to, e.g., rolling circle amplification (RCA), binding-induced DNA assembly (BINDA), nicking enzyme assisted fluorescence signal amplification (NEFSA), and, e.g., those described in Janssen et al. (2013) *Sensors*, 13, 1353-1384, the disclosure of which is incorporated herein by reference in its entirety.

Figure 7:
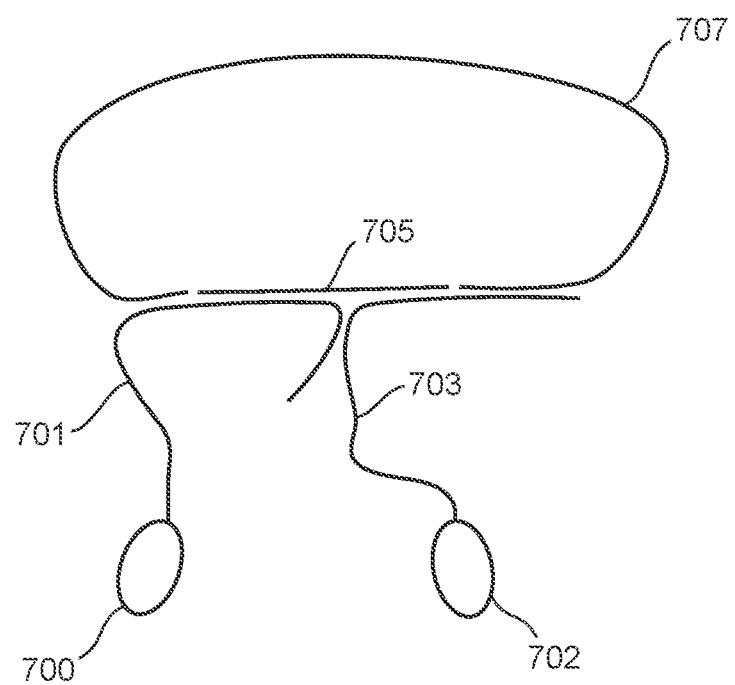
FIG. 7 depicts an embodiment of a polynucleotide complex formed by proximity association of polynucleotide-bound antigens that includes an associated circularizing oligonucleotide.

As a non-limiting example, referring to FIG. 7, in some instances, the association of two antigen-bound polynucleotides (701 and 703) facilitated by the aggregation of their bound antigens (700 and 702) allows for the circularization, e.g., through ligation, of a circularizing oligonucleotide (707) which, optionally, may involve a bridging polynucleotide (705). Circularization of a circularizing polynucleotide may allow for elongation of one of the antigen-bound polynucleotides, e.g., by RCA. In some instances, elongation and/or amplification by RCA involves the production of one or more repetitive sequences of an antigen-bound polynucleotide.

Detection

The presence of the amplification product may be determined, including qualitatively determined or quantitatively determined, by any convenient method. In some instances, the presence of the amplification product may be qualitatively determined, e.g., through a physical change in the amplification reaction that is indicative of efficient amplification of the target polynucleotide complex.

In some instances, the amplification product is detected and/or the amount of amplification product is measured by a detection protocol for non-specific detection of the amplified nucleic acid or a protocol for specific detection of the amplified nucleic acid. Representative non-specific detection protocols of interest include protocols that employ signal producing systems that selectively detect double stranded nucleic acid products, e.g., via intercalation. Representative detectable molecules that find use in such embodiments include fluorescent nucleic acid stains, such as phenanthridinium dyes, including monomers or homo- or heterodimers thereof, that provide enhanced fluorescence when complexed with nucleic acids. Examples of phenanthridinium dyes include ethidium homodimer, ethidium bromide, propidium iodide, and other alkyl-substituted phenanthridinium dyes. In another embodiment, a nucleic acid stain includes an acridine dye, or a homo- or heterodimer thereof, such as acridine orange, acridine homodimer, ethidium-acridine heterodimer, or 9-amino-6-chloro-2-methoxyacridine. In yet another embodiment, the nucleic acid stain is an indole or imidazole dye, such as Hoechst 33258, Hoechst 33342, Hoechst 34580, DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating Tb3+ and Eu3+, for example). In certain embodiments, the nucleic acid stain is a cyanine dye or a homo- or heterodimer of a cyanine dye that gives an enhanced fluorescence when associated with nucleic acids. In some instances, dyes described in U.S. Pat. Nos. 4,883,867, 5,582,977, 5,321,130, and 5,410,030, which are incorporated herein by reference in their entirety, may be used, including nucleic acid stains commercially available under the trademarks TOTO, BOBO, POPO, YOYO, TO-PRO, BO-PRO, PO-PRO and YO-PRO (Life Technologies, Inc. Grand Island, NY). In some instances, dyes described in U.S. Pat. Nos. 5,436,134, 5,658,751 and 5,863,753, which are incorporated herein by reference in their entirety, may be used, including nucleic acid stains commercially available under the trademarks SYBR, SYTO, SYTOX, PICOGREEN, OLIGREEN, and RIBOGREEN (Life Technologies, Inc. Grand Island, NY). In yet other embodiments, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives enhanced fluorescence when associated with nucleic acids, including nucleic acid stains commercially available under the trademarks SYTO, SYTOX, JOJO, JO-PRO, LOLO, LO-PRO (Life Technologies, Inc. Grand Island, NY).

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labeled with a directly or indirectly detectable label. A directly detectable label is one that can be directly detected without the use of additional reagents, while an indirectly detectable label is one that is detectable by employing one or more additional reagent, e.g., where the label is a member of a signal producing system made up of two or more components. In some embodiments, the label is a directly detectable label, where directly detectable labels of interest include, but are not limited to: fluorescent labels, radioisotopic labels, chemiluminescent labels, and the like. In some embodiments, the label is a fluorescent label, where the labeling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels, such as those described above, may also be employed.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, and in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple reaction vessels, e.g., multiple tubes, multi-well plates, etc., can be assessed at the same time.

In some instances, the elongation and/or amplification of a particular polynucleotide of a polynucleotide complex, e.g., an antigen-bound polynucleotide, a bridging polynucleotide, a circularizing oligonucleotide, etc., results in the duplication of one or more specific nucleic acid sequences resulting in one or more strands containing repeats of the one or more specific nucleic acid sequences. Such repetitive sequences may be detected, e.g., through hybridization of a probe nucleic acid specific for the repeated specific sequence. In certain instances, a tagged probe nucleic acid, e.g., a fluorescently tagged probe nucleic acid, an enzymatically tagged probe nucleic acid, a radiolabel tagged probe nucleic acid, etc., specific for the repeated specific sequence may be utilized to detect an elongated polynucleotide or amplification product that contains the repeated specific sequence. In some instances, hybridization of a tagged probe nucleic acid to a repeating sequence of an elongated polynucleotide or amplification product allows for the detection of the elongated polynucleotide or amplification product due to the high number of tagged probe nucleic acids hybridized to the elongated polynucleotide or amplification product, which results in a high local concentration of detectable tag.

For example, in some instances, repeats of one or more sequences of an antigen-bound polynucleotide are contained in an amplification product or elongation product produced according to the methods described herein and the repeats are detected through the use of a tagged probe nucleic acid specific for the repeating sequence units. In some instances, repeats of one or more sequences of a bridging polynucleotide are contained in an amplification product or elongation product produced according to the methods described herein and the repeats are detected through the use of a tagged probe nucleic acid specific for the repeating sequence units. In some instances, repeats of one or more sequences of a circularizing oligonucleotide are contained in an amplification product or elongation product produced according to the methods described herein and the repeats are detected through the use of a tagged probe nucleic acid specific for the repeating sequence units.

In certain embodiments, a repeating nucleic acid sequence may be produced by one or more of the elongation and/or amplification methods described herein, e.g., PCR amplification, isothermal amplification (e.g., RCA), etc., and the elongation and/or amplification product may be made detectable through hybridization of one or more fluorescently labeled probe nucleic acid to the elongation and/or amplification product. Such detectable elongation and/or amplification product may be identified through any convenient means for detecting fluorescence, including but not limited to, e.g., fluorescent microscopy, flow cytometry, imaging flow cytometry, etc. In some instances, identification of a detectable elongation and/or amplification product may allow for detection or identification of a molecule, particle, cell, tissue, organism, etc., associated with the antigen binding agent of the complex from which the elongation and/or amplification product was derived. For example, in some instances, fluorescent probe-bound elongation and/or amplification product may remain associated with a cell that produced the antigen binding agent allowing identification of the cell, e.g., by fluorescent microscopy, and/or isolation of the cell, e.g., by fluorescent activated cell sorting (FACS).

As noted above, in some instances, amplification may be monitored in real time to provide detection and/or quantitation. Where the detection protocol is a real-time protocol, e.g., as employed in qPCR reaction protocols, data may be collected at frequent intervals, for example once every 10 ms, or more or less frequently than once every 10 ms, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signaling moiety (i.e. fluorophore). The areas under the peaks can be determined which represents the intensity value for each signal, and if required, expressed as quotients of each other. The differential of signal intensities and/or ratios will allow changes in labeled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the amplification reaction, or multiple times during the reaction, e.g., after each cycle (e.g., as is done in real-time PCR monitoring).

According to the methods described herein, the presence of antigen binding agent may be detected, e.g., as above or below a particular detection threshold, or may be measured, e.g., the actual amount or concentration of the antigen binding agent in the sample may be measured when present above a particular detection threshold. The actual detection threshold for a subject antigen binding agent detection reaction will vary and will depend on, e.g., the antigen binding agent to be detected the particular amplification method employed, the detection method employed, and the like. In some instances, the detection threshold for the subject detection methods may range from 15 ng/ml to 1 pg/ml and may include less than 15 ng/ml, less than 14 ng/ml, less than 13 ng/ml, less than 12 ng/ml, less than 11 ng/ml, less than 10 ng/ml, less than 9 ng/ml, less than 8 ng/ml, less than 7 ng/ml, less than 6 ng/ml, less than 5 ng/ml, less than 4 ng/ml, less than 3 ng/ml, less than 2 ng/ml, less than 1 ng/ml, less than 500 pg/ml, less than 400 pg/ml, less than 300 pg/ml, less than 200 pg/ml, less than 100 pg/ml, less than 90 pg/ml, less than 80 pg/ml, less than 70 pg/ml, less than 60 pg/ml, less than 50 pg/ml, less than 40 pg/ml, less than 35 pg/ml, less than 30 pg/ml, less than 25 pg/ml, less than 20 pg/ml, less than 19 pg/ml, less than 18 pg/ml, less than 17 pg/ml, less than 16 pg/ml, less than 15 pg/ml, less than 14 pg/ml, less than 13 pg/ml, less than 12 pg/ml, less than 10 pg/ml, etc. In some instances, the detection threshold for a particular detection method described herein may be expressed in the minimum moles of antigen binding agent that may be detected in a sample and, such detection thresholds may range from 200 attomoles to 100 zeptomoles, including but not limited to e.g., 200 attomoles, 190 attomoles, 180 attomoles, 170 attomoles, 160 attomoles, 150 attomoles, 140 attomoles, 130 attomoles, 120 attomoles, 110 attomoles, 100 attomoles, 90 attomoles, 80 attomoles, 70 attomoles, 60 attomoles, 50 attomoles, 40 attomoles, 30 attomoles, 20 attomoles, 10 attomoles, 1 attomole, 900 zeptomoles, 800 zeptomoles, 700 zeptomoles, 600 zeptomoles, 500 zeptomoles, 400 zeptomoles, 350 zeptomoles, 300 zeptomoles, 250 zeptomoles, 200 zeptomoles, 190 zeptomoles, 180 zeptomoles, 170 zeptomoles, 160 zeptomoles, 150 zeptomoles, 140 zeptomoles, 130 zeptomoles, 120 zeptomoles, 110 zeptomoles, 100 zeptomoles, etc.

Following detection, which may or may not include qualitative or quantitative measurement of the amplification product, the result of the detection may be assessed to determine the likelihood that the antigen binding agent is present in the sample. In making such assessments, in some instances, the subject reaction may be compared to one or more control reactions or reference values. Control reactions of the subject method include positive controls, e.g., a reaction known to contain the antigen binding agent of interest and/or known to contain a known amount of antigen of interest. Control reactions may also include negative controls, e.g., reactions known to not contain a critical reagent, e.g., the antigen, the polymerase, a critical polynucleotide, etc. Reference values to which results of a detection reaction may be compared include but are not limited to a reference measurement from any control reaction performed previously, a standard curve gathered from a control reaction, a set of measured fluorescent values from positive or negative controls, user-defined reference values, manufacturer supplied reference values, etc. In some instances, assessment of a subject reaction may include comparison to a scale, e.g., a scale of reference values, which can be used to estimate the amount of antigen binding agent present in the sample.

Multiplexing

According to the methods described herein, a sample is readily screened for the presence of target antigen binding agent. The methods are suitable for detection of a single target antigen binding agent as well as multiplex analyses, in which two or more different target antigen binding agent are assayed in the sample. In these latter multiplex situations, the number of different sets of polynucleotide-bound antigens that may be employed typically ranges from about 2 to about 20 or higher, e.g., as up to 100 or higher, 1000 or higher, etc., including but not limited to e.g., 2 to 50, 2 to 100, 10 to 100, 50 to 100, 50 to 200, 50 to 300, 50 to 400, 50 to 500, etc. In one embodiment, a multiplexed assay may make use of various different antigens bound to uniquely tagged polynucleotides such that amplification of a particularly uniquely tagged polynucleotide is indicative of the presence of the antigen binding agent that corresponds to the particular antigen of the amplified tagged polynucleotide. Accordingly, the subject assays may make use of nucleic acid tagging and/or "barcoding" strategies to allow for the detection and/or quantification of a plurality of antigen binding agents in a sample. The number of different antigens, uniquely tagged with nucleic acid barcodes, that may be included in a multiplexed assay as described herein may vary and may be limited only by, e.g., the available length of polynucleotide in the antigen-bound polynucleotide for the barcode, the physical limit of antigen concentration that may be present in the reaction without negatively impacting the agglutination assay and/or poly nucleotide binding, and the like.

As such, in some instances, a panel of antigen binding agents may be screened in a single reaction and the presence or quantities of each antigen binding agent on the panel may be assessed. The detection methods described above may be utilized in parallel for the detection and measurement of amplification products in a duplexed assay. In some instances, in both multiplexed and non-multiplexed assays, nucleic acid sequencing methods may be utilized for detection and/or measurement of amplification product. For example, in some instances, quantitative sequencing may be utilized, e.g., in a multiplexed assay having produced a plurality of amplification products, to determine the relative amounts or presence of each amplification product allowing for a highly sensitive and highly multiplexed assessment of many different antigen binding agents in a single sample.

In certain embodiments, a multiplexed assay of the instant disclosure may be performed in a pooled reaction to form a plurality of amplicons and the formed amplicons may be subsequently quantified to provide the quantity of the individual antigen binding agents of the multiplexed assay. For example, in one embodiment, a plurality of different polynucleotide-bound antigens may be added to a sample containing or suspected to contain one or more antigen binding agents. Thus, upon agglutination of the antigens and ligation of the polynucleotides (optionally, though the use of a bridging polynucleotide), amplicons are formed corresponding to the antigen binding agents present in the sample. Accordingly, the relative amounts of each amplicon formed will correspond to the relative amounts of each antigen binding agent in the sample. Thus, each antigen binding agent may be quantified through quantification of the formed amplicons.

Quantification of the formed amplicons may be performed by any convenient method where the particular method utilized may depend in part on the number of different antigen binding agents to be detected, the sensitivity of detection desired, the sensitivity of quantification desired, the dynamic range of quantification desired, etc. Quantification may be performed in the pooled reaction or the reaction forming the amplicons may be aliquoted for quantification. For example, in some instances, the amplicons may be formed and quantification may be performed on the pooled sample, e.g., through quantitative sequencing of the amplicons. In other instances, the amplicons may be formed and quantification may be performed by aliquoting the sample and individually quantifying each amplicon, e.g., by qPCR using primers that hybridize to the amplicon.

In one embodiment of a multiplexed assay, each antigen is conjugated to a polynucleotide that contains a sequence unique to the bound antigen and a universal sequence for bridging polynucleotides. The unique sequence may be or may include a primer binding site. The universal sequence may be complementary to a portion of, including e.g., half of, a bridging polynucleotide such that upon agglutination of two antigens the attached polynucleotides are brought into such proximity that a bridging polynucleotide may simultaneously bind the universal sequences of the two antigen bound-polynucleotides, allowing ligation of the two antigen bound-polynucleotides. The sample, containing a plurality of amplicons formed by the ligation reaction may then be aliquoted into individual reactions each containing primer sets specific for the primer binding sites of a particular antigen and allowing for qPCR to be performed for the specific amplicon corresponding to a particular antigen. Accordingly, through amplification of each particular amplicon of the pool the amount of each antigen binding agent originally present in the sample may be determined.

Multiplexed assays of the instant disclosure may be performed using a library of polynucleotide-bound antigens. Such libraries will vary depending the number and/or type of antigens to be screened. Accordingly, in some instances, libraries of the instant disclosure may be categorized by the type of polynucleotide-bound antigens contained in the library, including e.g., pathogen libraries which contain various pathogen antigens for detection of antibodies produced by a host in response to infection by the pathogen or otherwise serve as a biomarker for an infection, autoimmune libraries which contain various self- or auto-antigens for detection of antibodies produced by a subject as part of an autoimmune disease or otherwise serve as a biomarker for autoimmune disease, cancer libraries which contain various antigens for detection of antibodies produced by a subject in response to the presence of a cancer or tumor or otherwise serve as a biomarker for cancer, cytokine libraries which contain various cytokine antigens for detection of antibodies produced by the subject as a result of aging or other neurological disorders, and the like. The number of different polynucleotide-bound antigens in a library will vary and may range from 10 or less to 1000 or more, including but not limited to e.g., 10 to 1000, 20 to 1000, 30 to 1000, 40 to 1000, 50 to 1000, 60 to 1000, 70 to 1000, 80 to 1000, 90 to 1000, 100 to 1000, 100 to 900, 100 to 800, 100 to 700, 100 to 600, 100 to 500, 100 to 400, 100 to 300, 100 to 200, 10 to 900, 10 to 800, 10 to 700, 10 to 600, 10 to 500, 10 to 400, 10 to 300, 10 to 200, 10 to 100, 20 to 100, 30 to 100, 40 to 100, 50 to 100, 60 to 100, 70 to 100, 80 to 100, 90 to 100, 12, 24, 36, 48, 96, 384, etc. The different polynucleotide antigens of a library may be physically separated, e.g., in separate containers or separate wells of a multi-well plate, or may not be physically separated, i.e., may be pooled, in a single solution, in a single container, etc.

In some instances, a library of polynucleotide-bound antigens may include a corresponding library of primers, e.g., primer pairs, for quantification from each antigen. In one embodiment, a pooled library of polynucleotide-bound antigens will have a corresponding library of primer pairs for specifically amplifying and quantifying the unique amplicon of each antigen. In some instances, such a library of primers may contain primer pairs each in individual wells of a multi-well plate such that each well is configured for the amplification and quantification of a particular amplicon specific for a particular antigen upon addition of an aliquot of the ligation reaction to each well. The quantification of each amplicon/antigen of the library thus allows for the determination of the amount of each antibody the library is configured to detect that is present in the initial sample. For example, in some instances, a library having 12 different polynucleotide-bound antigens will have a corresponding 12-well primer library where each well contains a primer pair configured to amplify an amplicon specific to one of the 12 antigens. In other instances, a library having 24 different polynucleotide-bound antigens will have a corresponding 24-well primer library where each well contains a primer pair configured to amplify an amplicon specific to one of the 24 antigens. In yet other instances, a library having 48 different polynucleotide-bound antigens will have a corresponding 48-well primer library where each well contains a primer pair configured to amplify an amplicon specific to one of the 48 antigens. In still other instances, a library having 96 different polynucleotide-bound antigens will have a corresponding 96-well primer library where each well contains a primer pair configured to amplify an amplicon specific to one of the 96 antigens. In other instances, a library having 384 different polynucleotide-bound antigens will have a corresponding 384-well primer library where each well contains a primer pair configured to amplify an amplicon specific to one of the 384 antigens. In some instances, a polynucleotide-bound antigen library will have more antigens than corresponding primer pairs provided on a multi-well primer pair plate, including e.g., where the primer library includes multiple plates of primer pairs in order to allow amplification of all of the amplicons of the antigen library.

Libraries of the present disclosure may also include one or more additional reagents for performing all or part of a method as described herein, including e.g., additional reagents for ligation, amplification, detection, etc. In some instances, additional reagents may be included in a pooled library. For example, in some instances, reagents for ligation, e.g., a ligase, may be included within a pooled library of polynucleotide-bound antigen. In some instances, additional reagents may be included in the individual wells of a multi-well plate. For example, in some instances, reagents for amplification, e.g., a polymerase, dNTPs, etc., may be included within the wells of a multi-well plate primer library. Appropriate buffers, salts, etc. may or may not be included in the libraries as described. In some instances, libraries and/or components thereof, e.g., a primer library, may be provided in a lyophilized form and may be rehydrated upon use.

Utility

The methods and compositions described herein have particular utility in the detection and/or quantification of an antigen binding agent present in sample. Such detection may find various application in a variety of technological fields including but not limited to e.g., basic scientific research (e.g., biomedical research, biochemistry research, immunological research, molecular biology research, microbiological research, cellular biology research, genetics, and the like), medical and/or pharmaceutical research (e.g., drug discovery research, drug design research, drug development research, pharmacology, toxicology, medicinal chemistry, pre-clinical research, clinical research, personalized medicine, and the like), medicine, epidemiology, public health, biotechnology, veterinary science, veterinary medicine, agriculture, material science, molecular detection, molecular diagnostics, and the like.

In some instances, methods described herein find use in detection of an antigen binding agent in a biological sample from a subject. The term "subject" as used herein refers to an animal, including humans, livestock, pets, laboratory animals, bioproduction animals (e.g., animals used to generate a bioproduct, e.g., an antibody), and the like. In some instances, a sample is derived from a mammalian subject, including e.g., mammalian tissue, mammalian cells, mammalian bodily fluid, mammalian excreted bodily fluids, mammalian semi-solid secretions, and the like.

Mammals of interest from which such samples may be derived include but are not limited to e.g., humans, ungulates (e.g., any species or subspecies of porcine (pig), bovine (cattle), ovine (sheep) and caprine (goats), equine (horses), camelids (camels) or, generally, hooved domestic or farm animals, etc.), rodents (e.g., mice, rats, gerbils, hamsters, guinea pigs, and the like), rabbits, cats, dogs, primates, and the like.

In some instances, samples may be derived from non-human animals including but not limited to non-human mammals. Non-human mammals from which samples may be derived include but are not limited to those listed above. Non-human animals from which samples may be derived include but are not limited to those listed above and, in addition, e.g., avians (i.e., birds, such as, e.g., chicken, duck, etc.), amphibians (e.g., frogs), fish, etc.

In some instances, the methods described herein are used to detect the presence and/or measure the amount of an antigen binding agent in a sample derived from a human in order to make an assessment as to whether the subject has a particular condition. In such instances, antigen binding agents derived from the subject will generally be monospecific antigen binding agents, e.g., monospecific antibodies, including e.g., monospecific polyclonal antibodies. Monospecific antibodies measured in a human or non-human subject may be antibodies that are monospecific for a disease antigen where the disease antigen may be endogenous to the host (i.e., a host derived antigen or autoantigen) or may be exogenous to the host (i.e., a non-host derived antigen or infections pathogen derived antigen).

In some embodiments, the methods described herein are utilized for providing an assessment, e.g., in the form of a judgment or appraisal of the presence of, and in some instances a diagnosis of, a subject's condition, determining a therapy for a subject having a condition, monitoring a subject having a condition, etc. In some instances an assessment of a subject's condition using the methods as described herein includes generating a written report that includes an artisan's assessment of the subject's current state of health i.e., a "diagnosis assessment", of the subject's prognosis, i.e., a "prognosis assessment", of possible treatment regimens, i.e., a "treatment assessment" and/or of responsiveness to therapy, i.e., a "prognosis assessment". Thus, a subject method may further include a step of generating or outputting a report providing the results of a diagnosis assessment, a prognosis assessment, treatment assessment, or a monitoring assessment, and combinations thereof, which report can be provided in the form of an electronic medium (e.g., an electronic display on a computer monitor), or in the form of a tangible medium (e.g., a report printed on paper or other tangible medium).

In some instances, assessments as described herein are performed as part of a treatment regimen, e.g., to assess the effectiveness of treatment or to determine the best timing of treatment or to determine whether modulation of treatment is necessary. For, example, in some instances a pretreatment sample may be collected and assessed according to the methods described herein and from the assessment a treatment protocol is selected. In other instances, a post-treatment sample is collected and compared, according to the assessments described herein, to a pre-treatment sample in order to evaluate treatment effectiveness. In other instances, one or more post treatment assessments are performed to best determine the timing of further therapy.

Conditions, including human and non-human animal conditions, for which the detection methods described herein include but are not limited to those conditions involving a subject's immune system and/or immune response. In some instances, a subject condition may be pathogen derived (e.g., an infection) and in other instances a subject condition may be subject derived (e.g., an autoimmune disease) and in some instances the derivation of the condition may be unknown.

Infection conditions, as used herein, may vary and include any condition in which a foreign antigen is present in a host organism including but not limited to common infectious diseases, emerging infectious diseases, symptomatic infections, asymptomatic infections, and the like. Non-limiting examples of infection conditions include but are not limited to those listed here, which are provided with exemplary condition-causing pathogens, e.g., *Acinetobacter* infections (*Acinetobacter baumannii*), Actinomycosis (*Actinomyces israelii, Actinomyces gerencseriae* and *Propionibacterium propionicus*), African sleeping sickness (African trypanosomiasis) (*Trypanosoma brucei*), AIDS (Acquired immunodeficiency syndrome) (HIV (Human immunodeficiency virus)), Amebiasis (*Entamoeba histolytica*), Anaplasmosis (*Anaplasma* genus), Anthrax (*Bacillus anthracis*), *Arcanobacterium haemolyticum* infection (*Arcanobacterium haemolyticum*), Argentine hemorrhagic fever (Junin virus), Ascariasis (*Ascaris lumbricoides*), Aspergillosis (*Aspergillus* genus), Astrovirus infection (Astroviridae family), Babesiosis (*Babesia* genus), *Bacillus cereus* infection (*Bacillus cereus*), Bacterial pneumonia (multiple bacteria), Bacterial vaginosis (BV) (multiple bacteria), *Bacteroides* infection (*Bacteroides* genus), Balantidiasis (*Balantidium coli*), *Baylisascaris* infection (*Baylisascaris* genus), BK virus infection (BK virus), Black piedra (*Piedraia hortae*), *Blastocystis hominis* infection (*Blastocystis hominis*), Blastomycosis (*Blastomyces dermatitidis*), Bolivian hemorrhagic fever (Machupo virus), *Borrelia* infection (*Borrelia* genus), Botulism (and Infant botulism) (*Clostridium botulinum*), Brazilian hemorrhagic fever (Sabia), Brucellosis (*Brucella* genus), Bubonic plague (the bacterial family Enterobacteriaceae), *Burkholderia* infection (usually *Burkholderia cepacia* and other *Burkholderia* species), Buruli ulcer (*Mycobacterium ulcerans*), Calicivirus infection (Norovirus and Sapovirus) (Caliciviridae family), Campylobacteriosis (*Campylobacter* genus), Candidiasis (Moniliasis; Thrush) (usually *Candida albicans* and other *Candida* species), Cat-scratch disease (*Bartonella henselae*), Cellulitis (usually Group A *Streptococcus* and *Staphylococcus*), Chagas Disease (American trypanosomiasis) (*Trypanosoma cruzi*), Chancroid (*Haemophilus ducreyi*), Chickenpox (Varicella zoster virus (VZV)), Chikungunya (Alphavirus), Chlamydia (*Chlamydia trachomatis*), *Chlamydophila pneumoniae* infection (Taiwan acute respiratory agent or TWAR) (*Chlamydophila pneumoniae*), Cholera (*Vibrio cholerae*), Chromoblastomycosis (usually *Fonsecaea pedrosoi*), Clonorchiasis (*Clonorchis sinensis*), *Clostridium difficile* infection (*Clostridium difficile*), Coccidioidomycosis (*Coccidioides immitis* and *Coccidioides posadasii*), Colorado tick fever (CTF) (Colorado tick fever virus (CTFV)), Common cold (Acute viral rhinopharyngitis; Acute coryza) (usually rhinoviruses and coronaviruses.), Creutzfeldt-Jakob disease (CJD) (PRNP), Crimean-Congo hemorrhagic fever (CCHF) (Crimean-Congo hemorrhagic fever virus), Cryptococcosis (*Cryptococcus neoformans*), Cryptosporidiosis (*Cryptosporidium* genus), Cutaneous larva migrans (CLM) (usually *Ancylostoma braziliense*; multiple other parasites), Cyclosporiasis (*Cyclospora cayetanensis*), Cysticercosis (*Taenia solium*), Cytomegalovirus infection (Cytomegalovirus), Dengue fever (Dengue viruses (DEN-1, DEN-2, DEN-3 and DEN-4)—Flaviviruses), *Desmodesmus* infection (Green algae *Desmodesmus armatus*), Dientamoebiasis (*Dientamoeba fragilis*), Diphtheria (*Corynebacterium diphtheriae*), Diphyllobothriasis (*Diphyllobothrium*), Dracunculiasis (*Dracunculus medinensis*), Ebola hemorrhagic fever (Ebolavirus (EBOV)), Echinococcosis (*Echinococcus* genus), Ehrlichiosis (*Ehrlichia* genus), Enterobiasis (Pinworm infection) (*Enterobius vermicularis*), *Enterococcus* infection (*Enterococcus* genus), Enterovirus infection (Enterovirus genus), Epidemic typhus (*Rickettsia prowazekii*), Erythema infectiosum (Fifth disease) (Parvovirus B19), Exanthem subitum (Sixth disease) (Human herpesvirus 6 (HHV-6) and Human herpesvirus 7 (HHV-7)), Fasciolopsiasis (*Fasciolopsis buski*), Fasciolosis (*Fasciola hepatica* and *Fasciola gigantica*), Fatal familial insomnia (FFI) (PRNP), Filariasis (Filarioidea superfamily), Food poisoning by *Clostridium perfringens* (*Clostridium perfringens*), Free-living amebic infection (multiple pathogens), *Fusobacterium* infection (*Fusobacterium* genus), Gas gangrene (*Clostridial myonecrosis*) (usually *Clostridium perfringens*; other *Clostridium* species), Geotrichosis (*Geotrichum candidum*), Gerstmann-Sträussler-Scheinker syndrome (GSS) (PRNP), Giardiasis (*Giardia intestinalis*), Glanders (*Burkholderia mallei*), Gnathostomiasis (*Gnathostoma spinigerum* and *Gnathostoma hispidum*), Gonorrhea (*Neisseria gonorrhoeae*), Granuloma inguinale (Donovanosis) (*Klebsiella granulomatis*), Group A streptococcal infection (*Streptococcus pyogenes*), Group B streptococcal infection (*Streptococcus agalactiae*), *Haemophilus influenzae* infection (*Haemophilus influenzae*), Hand, foot and mouth disease (HFMD) (Enteroviruses, mainly Coxsackie A virus and Enterovirus 71 (EV71)), Hantavirus Pulmonary Syndrome (HPS) (Sin Nombre virus), Heartland virus disease (Heartland virus), *Helicobacter pylori* infection (*Helicobacter pylori*), Hemolytic-uremic syndrome (HUS) (*Escherichia coli* O157:H7, 0111 and 0104:H4), Hemorrhagic fever with renal syndrome (HFRS) (Bunyaviridae family), Hepatitis A (Hepatitis A Virus), Hepatitis B (Hepatitis B Virus), Hepatitis C (Hepatitis C Virus), Hepatitis D (Hepatitis D Virus), Hepatitis E (Hepatitis E Virus), Herpes simplex (Herpes simplex virus 1 and 2 (HSV-1 and HSV-2)), Histoplasmosis (*Histoplasma capsulatum*), Hookworm infection (*Ancylostoma duodenale* and *Necator americanus*), Human bocavirus infection (Human bocavirus (HBoV)), Human *ewingii* ehrlichiosis (*Ehrlichia ewingii*), Human granulocytic anaplasmosis (HGA) (*Anaplasma phagocytophilum*), Human metapneumovirus infection (Human metapneumovirus (hMPV)), Human monocytic ehrlichiosis (*Ehrlichia chaffeensis*), Human papillomavirus (HPV) infection (Human papillomavirus (HPV)), Human parainfluenza virus infection (Human parainfluenza viruses (HPIV)), Hymenolepiasis (*Hymenolepis nana* and *Hymenolepis diminuta*), Epstein-Barr Virus Infectious Mononucleosis (Mono) (Epstein-Barr Virus (EBV)), Influenza (flu) (Orthomyxoviridae family), Isosporiasis (*Isospora belli*), Kawasaki disease (unknown pathogen), Keratitis (multiple pathogens), *Kingella kingae* infection (*Kingella kingae*), Kuru (PRNP), Lassa fever (Lassa virus), Legionellosis (Legionnaires' disease) (*Legionella pneumophila*), Legionellosis (Pontiac fever) (*Legionella pneumophila*), Leishmaniasis (*Leishmania* genus), Leprosy (*Mycobacterium leprae* and *Mycobacterium lepromatosis*), Leptospirosis (*Leptospira* genus), Listeriosis (*Listeria monocytogenes*), Lyme disease (*Lyme borreliosis*) (usually *Borrelia burgdorferi* and other *Borrelia* species), Lymphatic filariasis (Elephantiasis) (*Wuchereria bancrofti* and *Brugia*

*malayi*), Lymphocytic choriomeningitis (Lymphocytic choriomeningitis virus (LCMV)), Malaria (*Plasmodium* genus), Marburg hemorrhagic fever (MHF) (Marburg virus), Measles (Measles virus), Middle East respiratory syndrome (MERS) (Middle East respiratory syndrome coronavirus), Melioidosis (Whitmore's disease) (*Burkholderia pseudomallei*), Meningitis (multiple pathogens), Meningococcal disease (*Neisseria meningitidis*), Metagonimiasis (usually *Metagonimus yokagawai*), Microsporidiosis (*Microsporidia phylum*), *Molluscum contagiosum* (MC) (*Molluscum contagiosum* virus (MCV)), Monkeypox (Monkeypox virus), Mumps (Mumps virus), Murine typhus (Endemic typhus) (*Rickettsia typhi*), *Mycoplasma* pneumonia (*Mycoplasma pneumoniae*), Mycetoma (numerous species of bacteria (Actinomycetoma) and fungi (Eumycetoma)), Myiasis (parasitic dipterous fly larvae), Neonatal conjunctivitis (Ophthalmia neonatorum) (most commonly *Chlamydia trachomatis* and *Neisseria gonorrhoeae*), Nocardiosis (usually *Nocardia asteroides* and other *Nocardia* species), Onchocerciasis (River blindness) (*Onchocerca volvulus*), Paracoccidioidomycosis (South American blastomycosis) (*Paracoccidioides brasiliensis*), Paragonimiasis (usually *Paragonimus westermani* and other *Paragonimus* species), Pasteurellosis (*Pasteurella* genus), Pathogenic enteric diseases (including e.g., those caused by pathogenic strains of enteric bacteria (e.g., pathogenic *Clostridium difficile*, pathogenic *Salmonella enterica*, pathogenic *Bacillus cereus*, pathogenic *Helicobacter pylori*, pathogenic *Campylobacter*, etc.), Pediculosis capitis (Head lice) (*Pediculus humanus* capitis), Pediculosis corporis (Body lice) (*Pediculus humanus* corporis), Pediculosis pubis (Pubic lice, Crab lice) (Phthirus pubis), Pelvic inflammatory disease (PID) (multiple pathogens), Pertussis (Whooping cough) (*Bordetella pertussis*), Plague (*Yersinia pestis*), Pneumococcal infection (*Streptococcus pneumoniae*), *Pneumocystis* pneumonia (PCP) (*Pneumocystis jirovecii*), Pneumonia (multiple pathogens), Poliomyelitis (Poliovirus), *Prevotella* infection (*Prevotella* genus), Primary amoebic meningoencephalitis (PAM) (usually *Naegleria fowleri*), Progressive multifocal leukoencephalopathy (JC virus), Psittacosis (*Chlamydophila psittaci*), Q fever (*Coxiella burnetii*), Rabies (Rabies virus), Rat-bite fever (*Streptobacillus moniliformis* or Spirillum minus), Respiratory syncytial virus infection (Respiratory syncytial virus (RSV)), Rhinosporidiosis (*Rhinosporidium seeberi*), Rhinovirus infection (Rhinovirus), Rickettsial infection (*Rickettsia* genus), Rickettsialpox (*Rickettsia akari*), Rift Valley fever (RVF) (Rift Valley fever virus), Rocky Mountain spotted fever (RMSF) (*Rickettsia rickettsii*), Rotavirus infection (Rotavirus), Rubella (Rubella virus), *Salmonellosis* (*Salmonella* genus), SARS (Severe Acute Respiratory Syndrome) (SARS coronavirus), Scabies (*Sarcoptes scabiei*), Schistosomiasis (*Schistosoma* genus), Sepsis (multiple pathogens, including e.g., Capnocytophaga), Shigellosis (Bacillary dysentery) (*Shigella* genus), Shingles (Herpes zoster) (Varicella zoster virus (VZV)), Smallpox (Variola) (Variola major or Variola minor), Sporotrichosis (*Sporothrix schenckii*), Staphylococcal food poisoning (*Staphylococcus* genus), Staphylococcal infection (*Staphylococcus* genus), Strongyloidiasis (*Strongyloides stercoralis*), Subacute sclerosing panencephalitis (Measles virus), Syphilis (*Treponema pallidum*), Taeniasis (*Taenia* genus), Tetanus (Lockjaw) (*Clostridium tetani*), Tinea barbae (Barber's itch) (usually *Trichophyton* genus), Tinea capitis (Ringworm of the Scalp) (usually *Trichophyton tonsurans*), Tinea corporis (Ringworm of the Body) (usually *Trichophyton* genus), Tinea cruris (Jock itch) (usually *Epidermophyton floccosum, Trichophyton rubrum*, and *Trichophyton mentagrophytes*), Tinea manum (Ringworm of the Hand) (*Trichophyton rubrum*), Tinea nigra (usually *Hortaea werneckii*), Tinea pedis (Athlete's foot) (usually *Trichophyton* genus), Tinea unguium (Onychomycosis) (usually *Trichophyton* genus), Tinea versicolor (*Pityriasis versicolor*) (*Malassezia* genus), Toxocariasis (Ocular Larva Migrans (OLM)) (*Toxocara canis* or *Toxocara cati*), Toxocariasis (Visceral Larva Migrans (VLM)) (*Toxocara canis* or *Toxocara cati*), Trachoma (*Chlamydia trachomatis*), Trinochccliasis (*Toxoplasma gondii*), Trichinlosis (*Trichinella spiralis*), Trichomoniasis (*Trichomonas vaginalis*), Trichuriasis (Whipworm infection) (*Trichuris trichiura*), Tuberculosis (usually *Mycobacterium tuberculosis*), Tularemia (*Francisella tularensis*), Typhoid Fever (*Salmonella enterica* subsp. *enterica*, serovar *typhi*), *Ureaplasma urealyticum* infection (*Ureaplasma urealyticum*), Valley fever (*Coccidioides immitis* or *Coccidioides posadasii*), Venezuelan equine encephalitis (Venezuelan equine encephalitis virus), Venezuelan hemorrhagic fever (Guanarito virus), Viral pneumonia (multiple viruses), West Nile Fever (West Nile virus), White *piedra* (*Tinea blanca*) (*Trichosporon beigelii*), *Yersinia pseudotuberculosis* infection (*Yersinia pseudotuberculosis*), Yersiniosis (*Yersinia enterocolitica*), Yellow fever (Yellow fever virus), Zika virus disease (Zika virus), Zygomycosis (Mucorales order (Mucormycosis) and Entomophthorales order (Entomophthoramycosis)), and the like. Generally herein, detection of an infection condition according to the described methods includes detecting a host immune response to the infection by detecting one or more antigen binding agents, e.g., a host derived antibody to a pathogen derived antigen, present in a sample derived from the host.

Accordingly, in some instances, the instant methods may find use in detecting the presence of a pathogen in a subject derived or other type of sample by detecting the presence of one or more antibodies to the pathogen or a component thereof in the sample. Pathogens that may be detected according to the instant methods include but are not limited to e.g., viral pathogens, bacterial pathogens, fungal pathogens, protozoa pathogens, and the like. As will be readily understood, the presence of a newly discovered pathogen within a sample may be assayed for by isolating an antigenic component from the pathogen for use as a polynucleotide-conjugated antigen in according to one or more embodiments of the instant disclosure.

In some instances, the method described herein will detect and/or measure the presence of an antibody to an HIV antigen including but not limited to e.g., HIV1 antigens, HIV2 antigens, HIV1/2 antigens, p24, gp120, gp160, gp41, gp36, and the like.

Autoimmune conditions, as used herein, may vary and include any condition in which a subject's own immune cells attack healthy tissue and/or a subject develops an immune response to a subject-derived antigen including but not limited to symptomatic autoimmune diseases, asymptomatic autoimmune diseases, acute autoimmune diseases, chronic autoimmune diseases, transplant induced autoimmune diseases, and the like. Without being bound by theory, in some instances an autoimmune disease may be triggered by the presence of a foreign substance but the activated immune response may not be specifically directed to the foreign substance. Areas of the body generally affected by autoimmune conditions include but are not limited to, e.g., blood vessels, connective tissue, endocrine tissues (e.g., thyroid tissues, pancreas tissues, etc.), joint tissues, muscle tissues, hematopoietic tissues (e.g., including red blood cells and the like), epithelial tissues (e.g., including the skin and gut). Non-limiting examples of autoimmune conditions and autoimmune-related conditions include but are not limited to, e.g., Acute Disseminated Encephalomyelitis (ADEM), Acute necrotizing hemorrhagic leukoencephalitis, Addison's disease, Adrenalitis, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called "Wegener's" Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, *Polyarteritis nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA), and the like. Generally herein, detection of an autoimmune condition according to the described methods includes detecting a subject autoimmune response by detecting one or more antigen binding agents, e.g., a subject derived autoimmune antibody to a subject derived antigen, present in a sample derived from the subject. In some instances, a particular autoimmune disease may be characterized by the presence of multiple different autoantibodies and, thus, multiplexed methods for detection, as described herein, may be utilized to detect or measure the levels of a panel of autoimmune-related autoantibodies.

Methods of the instant disclosure may find use in detecting one or more clinically relevant autoantibodies including but not limited to e.g., one or more autoantibodies generated by a subject in response to a neoplasm including but not limited to e.g., where the neoplasm is one or more of prostate cancer, breast cancer, lung cancer, colon cancer, stomach cancer, liver cancer and thyroid cancer. In certain instances, detection may be performed before the presence of disease symptoms. In other instances, detection may be performed following the presence of disease symptoms including e.g., after the appearance of one or more disease symptoms but prior to treatment, during treatment, following treatment, or a combination thereof.

Useful autoantibodies may include cancer autoantibodies (i.e., antibodies that are indicative of the presence of a cancer). Cancer autoantibodies that may identify or predict the presence of a cancer may include but are not limited to e.g., prostate cancer autoantibodies (including but not limited to e.g., those biomarker autoantibodies that specifically bind the gene product of alpha-methylacyl-CoA racemase (AMACR), Bromodomain Containing 2 (BRD2), Caldesmon 1 (CALD1), Eukaryotic Translation Initiation Factor 4 Gamma, 1 (EIF4G1), kallikrein-3 (KLK3), New York Esophageal Squamous Cell Carcinoma 1 (NY-ESO-1), Parkinson Protein 7 (PARK7), PC4 And SFRS1 Interacting Protein 1 (PSIP1), Ribosomal Protein L13a (RPL13A), Ribosomal Protein L22 (RPL22), Synovial Sarcoma, X Breakpoint 2 (SSX2), (TAR DNA Binding Protein (TARDBP), Transferrin Receptor (TFRC), talin 1 (TLN1), X antigen family member 1B (XAGE1B), etc.), breast cancer autoantibodies (including but not limited to e.g., those biomarker autoantibodies that specifically bind the gene product of Alpha2-HS glycoprotein (AHSG), ASB9 ankyrin repeat and SOCS box containing 9 (ASB9), Breast Cancer 1, Early Onset (BRCA1), Breast Cancer 2, Early Onset (BRCA2), Carcinoembryonic antigen-related cell adhesion molecules (CEACAM) genes, Eukaryotic elongation factor-2 kinase (EEF2K), erb-b2 receptor tyrosine kinase 2 (ERBB2), heat-shock protein 60 (HSP60), mucin 1 (MUC1), Myc, NY-ESO-1, cyclin-dependent kinase inhibitor 2A (p16), PARK7, RELT tumor necrosis factor receptor, serine active site containing 1 (SERAC1), tumor protein p53 (TP53), etc.), lung cancer autoantibodies (including but not limited to e.g., those biomarker autoantibodies that specifically bind the gene product of annexin A1 (ANXA1), cancer antigen 1 (CAGE1), CEACAM genes, enolase 1 (ENO1), ERBB2, GBU4-5, gastrin releasing peptide (GRP), MUC1, Myc, NY-ESO-1, phosphoglycolate phosphatase (PGP), ribosomal protein SA (RPSA), superoxide dismutase 2 (SOD2), TP53, Triose phosphate isomerase (TPI), tyrosine 3-monooxygenase/tryptophan 5-monooxygenase activation protein theta (YWHAQ), etc.), colon cancer autoantibodies (including but not limited to e.g., those biomarker autoantibodies that specifically bind the gene product of cyclin B1 (CCNB1), cyclin D1 (CCND1), CEACAM genes, GRP, HSP60, IMP (inosine 5'-monophosphate) dehydrogenase 1 (IMPDH1), insulin like growth factor 2 mRNA binding protein 3 (KOC), mucin SAC (MUCSAC), Myc, nucleobindin 1 (NUCB1), nucleoporin 62 kDa (NUP62), p16, Fas (TNF receptor superfamily member 6) (TNFRSF6), TP53, etc.), stomach cancer autoantibodies (including but not limited to e.g., those biomarker autoantibodies that specifically bind the gene product of CEACAM genes, GRP, MUC1, TP53, etc.), liver cancer autoantibodies (including but not limited to e.g., those biomarker autoantibodies that specifically bind the gene product of alpha fetoprotein (AFP), Apoptosis inducing factor (AIF), angiotensin I converting enzyme (DCP), DEAD-box helicase 3, X-linked (DDX3X), EEF2K, glyceraldehyde-3-phosphate dehydrogenase (GAPDH), thyroid carcinoma, Hurthle cell (HCC), heterogeneous nuclear ribonucleoprotein A2 (HNRNPA2), HSP70, NUP62, polycystin 1, transient receptor potential channel interacting (PBP), peroxiredoxin (PRDX), SOD2, TP53, TPI, etc.), and the like. Accordingly, in some instances, a subject of the instant disclosure may include a subject having cancer, a subject suspected of having cancer and/or a subject having been or being treated for cancer including but not limited to e.g., prostate cancer, breast cancer, lung cancer, colon cancer, stomach cancer, liver cancer, and the like.

In some instances, a subject of the instant disclosure may have or be suspected of having one or more paraneoplastic syndrome, i.e., a syndrome that is the consequence of cancer in the body but that is not due to the local presence of cancer cells. Paraneoplastic syndromes include but are not limited to e.g., endocrine paraneoplastic syndromes (including e.g., Cushing syndrome, syndrome of inappropriate antidiuretic hormone (ADH) secretion (SIADH), hypercalcemia, hypoglycemia, carcinoid syndrome, polycythemia, hyperaldosteronism, etc.), neurological paraneoplastic syndromes (including e.g., Lambert-Eaton myasthenic syndrome (LEMS), Paraneoplastic cerebellar degeneration, Encephalomyelitis, Limbic encephalitis, Brainstem encephalitis, Opsoclonus myoclonus ataxia syndrome, anti-NMDA receptor encephalitis, Polymyositis, etc.), mucocutaneous paraneoplastic syndromes (including e.g., *Acanthosis nigricans*, Dermatomyositis, Leser-Trélat sign, Necrolytic migratory erythema, Sweet's syndrome, Florid cutaneous papillomatosis, Pyoderma gangrenosum, Acquired generalized hypertrichosis, etc.), hematological paraneoplastic syndromes (including e.g., Granulocytosis, Polycythemia, Trousseau sign, Nonbacterial thrombotic endocarditis, Anemia, etc.), Membranous glomerulonephritis, Tumor-induced osteomalacia, Stauffer syndrome, Neoplastic fever, and the like. Accordingly, the instant methods may identify the presence of or predict the presence of one or more paraneoplastic syndromes or a neoplasm associated with the paraneoplastic syndrome in a subject e.g., by the detection of an autoantibody in the subject.

In some instances, the methods of the instant disclosure include identifying or predicting the presence of autoantibodies associated with dermatomyositis, including but not limited to e.g., autoantibodies to one or more gene products of MORC family CW-type zinc finger 3 (NXP2), tripartite motif containing 33 (TIF1γ), small ubiquitin like modifier activating enzyme (SAE), and the like.

In some instances, the methods of the instant disclosure include identifying or predicting the presence of autoantibodies associated with systemic sclerosis, including but not limited to e.g., autoantibodies to RNA polymerase III.

In some instances, the methods of the instant disclosure include identifying or predicting the presence of autoantibodies associated with Lambert-Eaton myasthenic syndrome, including but not limited to autoantibodies to one or more gene products of voltage-gated calcium channel genes.

In some instances, the methods of the instant disclosure include identifying or predicting the presence of autoantibodies associated with Myasthenia gravis, including but not limited to autoantibodies to one or more gene products of Titin, ryanodine receptor, and the like.)

In some instances, the methods of the instant disclosure include identifying or predicting the presence of autoantibodies associated with Paraneoplastic pemphigus, including but not limited to autoantibodies to one or more gene products of Desmoplakins I, esmoplakins II, envoplakin, plectin, periplakin, and the like.

In some instances, the methods of the instant disclosure include identifying or predicting the presence of autoantibodies associated with Paraneoplastic neurological disease including but not limited to autoantibodies to one or more gene products/antigens of Hu (Anti-Neuronal Autoantibody 1 (ANNA1), Yo (Purkinje cell cytoplasmic antibody type 1 (PCA-1)), Ri (Anti-Neuronal Autoantibody 2 (ANNA2), Ma1/2 (Paraneoplastic antigen Ma1/2 PNMA1/2), CV2 (CV2/CRMP5-Ab), amphiphysin, SRY (sex determining region Y)-box 1 (SOX1), Zic family member 4 (Zic4), Tr (Delta/Notch-Like Epidermal Growth Factor-Related Receptor (DNER)), protein kinase C, gamma (PKCγ), CARPVII, Ca/ARHGAP26, and the like.

In some instances, subjects of the instant disclosure may include subjects having or suspected of having or being treated for a neurological disorder, including e.g., neurological disorders with an autoimmune component (e.g., neuroinflammatory diseases, inflammatory neuromuscular diseases, etc.) including but not limited to e.g., Myasthenia gravis, multiple sclerosis, and the like. As such, in some instances, the methods of the instant disclosure may include identifying or predicting the presence of autoantibodies associated with a neurological disorder including but not limited to e.g., autoantibodies that bind a component of the voltage-gated potassium channel complex (e.g., VGKC, LG11, CASPR2, etc.), autoantibodies that bind a NMDA receptor (e.g., NR2), autoantibodies that bind an AMPA receptor, autoantibodies that bind a GABAA/B receptor, autoantibodies that bind a dipeptidyl-peptidase-like protein-6 (DPPX), antibodies that bind to IgLON5, autoantibodies that bind to a pathogenic component of Myasthenia gravis or autoantibodies generally associated with Myasthenia gravis (including but not limited to e.g., anti-acetylcholine receptor (AChR) antibodies, anti-muscle specific kinase (MuSK) antibodies, anti-lipoprotein related protein (LRP)4, antibodies to agrin, antibodies to cortactin, and the like), autoantibodies that bind to a pathogenic component of multiple sclerosis or autoantibodies generally associated with multiple sclerosis (including e.g., anti-aquaporin 4 antibodies, anti-myelin antibodies (anti-MOG, anti-MBP, etc.), anti-KIR4.1 antibodies, anti-SPAG16 antibodies, etc.).

In some instances, subjects of the instant disclosure may be subjects having or suspected of having, or being treated for biliary cirrhosis. As such, in some instances, the methods of the instant disclosure may include identifying or predicting the presence of biliary cirrhosis through the detection or measurement of one or more biliary cirrhosis associated antibodies including but not limited to e.g., anti-M2 mitochondrial antibodies.

In some instances, subjects of the instant disclosure may be subjects having or suspected of having, or being treated for autoimmune rheumatic diseases. As such, in some instances, the methods of the instant disclosure may include identifying or predicting the presence of autoimmune rheumatic diseases through the detection or measurement of one or more autoimmune rheumatic diseases associated antibodies including but not limited to e.g., anti-nuclear antibodies, anti-SSA autoantibodies (Anti-Sjogren's-syndrome-related antigen A) anti-Sjogren's syndrome type B (SSB) antibodies, anti-Smith antibodies, anti-U1RNP antibody, anti-double stranded DNA antibody, anti-phospholipid antibodies, anti-citrullinated protein antibodies, and the like.

In some instances, subjects of the instant disclosure may be subjects having or suspected of having, or being treated for idiopathic inflammatorymyopathies (IIMs), also separately referred to as polymyositis (PM) and dermatomyositis (DM). As such, in some instances, the methods of the instant disclosure may include identifying or predicting the presence of IIMs through the detection or measurement of one or more IIM associated antibodies including but not limited to e.g., anti-Jo-1 antibodies, aminoacyl-tRNA synthetase autoantibodies (e.g., Jo-1 (histidyl) antibodies, PL-7 (threonyl) antibodies, PL-12 (alanyl) antibodies, OJ (isoleucyl) antibodies, EJ (glycyl) antibodies, KS (asparaginyl) antibodies, Zo (phenylalanyl) antibodies and Ha (tyrosyl) antibodies, etc.), anti-Mi-2 antibodies, anti-MDA5 antibodies, anti-NXP2 antibodies, anti-SAE antibodies, and anti-TIF1γ (p155/140) antibodies, and the like.

In some instances, subjects of the instant disclosure may be subjects having or suspected of having, or being treated for non-inflammatory muscle necrosis. As such, in some instances, the methods of the instant disclosure may include identifying or predicting the presence of non-inflammatory muscle necrosis through the detection or measurement of one or more non-inflammatory muscle necrosis associated antibodies including but not limited to e.g., anti-3-hydroxy-3-methylglutaryl-coenzyme A reductase (HMGCR) antibodies.

In some instances, subjects of the instant disclosure may be subjects having or suspected of having, or being treated for systemic sclerosis and mixed-connective tissue disease. As such, in some instances, the methods of the instant disclosure may include identifying or predicting the presence of systemic sclerosis and/or mixed-connective tissue disease through the detection or measurement of one or more systemic sclerosis or mixed-connective tissue disease associated antibodies including but not limited to e.g., anti-PM-Scl antibodies, anti-Ku antibodies, and anti-U1RNP antibodies, and the like.

In some instances, subjects of the instant disclosure may be subjects having or suspected of having, or being treated for a metabolic disease (e.g., diabetes including e.g., type 1 diabetes). As such, in some instances, the methods of the instant disclosure may include identifying or predicting the presence of a metabolic disease through the detection or measurement of one or more metabolic disease associated antibodies including but not limited to e.g., anti-Glutamic acid decarboxylase (GAD) antibodies, anti-tyrosine phosphatase-like molecule antibodies, anti-IA-2 antibodies and anti-insulin antibodies, e.g., as useful in detecting and/or monitoring type 1 diabetes.

In some instances, disorders of the instant disclosure and autoantibodies that may be detected using the methods as described herein for the identification of a condition or as part of a prognosis for a condition in a subject include but are not limited to e.g., those described in Zaenker & Ziman. Cancer Epidemiol Biomarkers Prev. (2013) 22(12):2161-81; Leslie et al. J Clin Invest (2001) 108(10):1417-22; Damoiseaux et al. Autoimmunity Reviews (2015) 14:555-563, the disclosures of which are incorporated herein by reference in their entirety.

In some instances, the methods described herein may find use in monitoring a patient following a treatment, e.g., following surgery, following cancer therapy, following treatment for an infectious condition, following treatment for an autoimmune condition, and the like. In some instances, the methods described herein may be used to monitor a subject following surgical treatment for cancer, e.g., to monitor autoantibody levels associated with the presence or absence of cancer following surgical cancer removal. For example, in one embodiment, the methods described herein may be used to monitor one or more thyroglobulin autoantibodies following thyroidectomy.

In some instances, methods of the instant disclosure find use in detecting one or more anti-thryoglobulin antibodies, one or more anti-C1q antibodies, one or more anti-MPO antibodies, one or more anti-transglutaminase antibodies, one or more anti-Sm/RNP antibodies, one or more anti-GAD65 antibodies, one or more anti-Ro/SSA antibodies, one or more anti-JO-1 antibodies, one or more anti-IA-2 antibodies, one or more anti-La/SSB antibodies, one or more anti-PR3 antibodies, one or more anti-Sm B/B' antibodies, one or more anti-CENP-A antibodies, one or more anti-U1-snRNP-C antibodies, one or more anti-Gliadin antibodies, one or more anti-Histone H3 antibodies, one or more anti-H2B antibodies, one or more anti-SmD antibodies, one or more anti-Histone H4 antibodies or one or more anti-insulin H antibodies. Accordingly, in some instances, an antigen of the instant method may be one or more thryoglobulin antigens, one or more C1q antigens, one or more MPO antigens, one or more transglutaminase antigens, one or more Sm/RNP antigens, one or more GAD65 antigens, one or more Ro/SSA antigens, one or more JO-1 antigens, one or more IA-2 antigens, one or more La/SSB antigens, one or more PR3 antigens, one or more Sm B/B' antigens, one or more CENP-A antigens, one or more U1-snRNP-C antigens, one or more Gliadin antigens, one or more Histone H3 antigens, one or more H2B antigens, one or more SmD antigens, one or more Histone H4 antigens or one or more insulin H antigens. In certain multiplex assays a particular assay may include a combination of multiple antigens, individually conjugated to a polynucleotide as described herein, where the antigens may be each of or be selected from a thryoglobulin antigen, a C1q antigen, a MPO antigen, a transglutaminase antigen, a Sm/RNP antigen, a GAD65 antigen, a Ro/SSA antigen, a JO-1 antigen, a IA-2 antigen, a La/SSB antigen, a PR3 antigen, a Sm B/B' antigen, a CENP-A antigen, a U1-snRNP-C antigen, a Gliadin antigen, a Histone H3 antigen, a H2B antigen, a SmD antigen, a Histone H4 antigen and/or an insulin H antigen.

In some instances, the subject methods find use in normalizing measured values for one or more antigen binding agents present in a sample. For example, in some instances the level of a particular antigen binding agent may be normalized according to the level of a second antigen binding agent present in the sample. In some instances, the level of an antigen binding agent may be normalized according to the level of one or more immunoglobulins present in the sample. In some instances, the level of immunoglobulin in a sample may be indicative of an immunoglobulin deficiency.

Any convenient sample may be used in performing the methods as described herein. In some instances, samples obtained from a subject, e.g., patient samples, may include but are not limited to, e.g., tissues samples (e.g., biopsy samples). Tissue samples, as used herein, generally refers to samples that contain cells and other components and may vary but generally include skin tissue samples, muscle tissue samples, tumor tissue samples, blood samples, bone samples, bone marrow samples, brain tissue samples, connective tissue samples, and the like. In some instances, e.g., where a tissue sample is solid or semi-solid, a tissue sample may be liquefied or a cellular sample may be dissociated and/or homogenized prior to use in the methods as described herein. In some instances, such pre-processing is not necessary, e.g., when the tissue is a liquid tissue sample, e.g., blood. In some instances, the methods described herein may be performed on solid or semi-solid tissue samples without pre-processing, e.g., on tissue sections or cytological samples of cells obtained from a solid or semi-solid tissue, e.g., as performed in histological or cytological methods. Accordingly, in some instances, the subject method may find use in staining, e.g., for the identification of an antigen binding agent, a histological or cytological sample.

In certain embodiments, the specificity of the antigen-binding agent detection method of the instant disclosure is independent of the presence of anti-polynucleotide antibodies in the sample. As such, the described assay may be performed regardless of whether an anti-polynucleotide antibody is or is not present in the sample. In some instances, a sample of the instant disclosure may be a sample known to contain anti-polynucleotide antibodies. In some instances, a sample of the instant disclosure may be a sample suspected to contain anti-polynucleotide antibodies. The term "anti-polynucleotide antibody" as used herein includes those antibodies produced by a subject's immune system that specifically bind one or more polynucleotides including but not limited to e.g., anti-DNA autoantibodies, anti-double-stranded DNA (dsDNA) antibodies, anti-single-stranded DNA (ssDNA) antibodies, etc.

Anti-DNA antibodies have some prevalence in the general population and certain subjects, including those predisposed to of having autoimmune disease, have an increased likelihood of displaying anti-DNA antibodies in their blood. In addition, certain conditions are or may be correlated with the presence and/or increased levels of anti-DNA antibodies. Such conditions include but are not limited to e.g., sytemic lupus erythrumatosus (SLE), Rheumatological diseases (e.g., Antiphospholipid antibody syndrome, Rheumatoid arthritis, CREST (calcinosis, Raynaud's disease, esophageal dysmotility, sclerodactyly, and telangiectasia), Scleroderma, Vasculitis, Juvenile rheumatoid arthritis, Mixed connective tissue disease, etc.), Malignancy diseases (e.g., Lymphoma and other cancers), Infectious diseases (e.g., Tuberculosis and other infections), Endocrine disorders, Hepatitis (e.g., Autoimmune hepatitis, Chronic hepatitis B, etc.), Sarcoidosis, Familial Mediterranean fever, Idiopathic thrombocytopenic purpura, Rheumatic heart disease, Myasthenia Graves' disease, End stage renal disease, Ulcerative colitis, Epilepsy, Fibromyalgia, Osteochondritis, Osteoarthritis, Evans syndrome, Skin psoriasis, Skin rash, multiple sclerosis, and the like. Subjects and conditions associated with the presence or increased levels of anti-DNA antibodies include but are not limited to e.g., those described in e.g., Isenberg et al. Rheumatology (Oxford). (2007) 46(7):1052-6; Attar et al. Saudi Med J. (2010) 31(7):781-7 and Williamson et al. Proc Natl Acad Sci USA. (2001) 98(4):1793-8; the disclosures of which are incorporated herein by reference in their entirety.

In some instances, patient samples (e.g., blood, serum, etc.) may contain or may be more likely to contain or suspected of containing anti-polynucleotide antibodies, including e.g., those anti-DNA antibody associated conditions described above and the human patient population in general. The inventors of the instant disclosure have discovered that, in certain instances, anti-polynucleotide antibodies can interfere with agglutination assays by, without being bound by theory, interfering with agglutination of desired antigens by target antigen binding agents and/or generating false-positive agglutination of polynucleotide-bound antigens with anti-polynucleotide antibodies. In some instances, the deleterious effects of anti-polynucleotide antibodies on an agglutination assay as described herein may be mitigated by the addition of unbound (i.e., free) polynucleotide to the agglutination reaction.

In certain instances, methods of the instant disclosure include the addition of free DNA, e.g., free ssDNA) to the agglutination reaction, including where such free DNA is added to samples known or expected to contain anti-DNA antibodies and where free DNA is added prophylactically to sample where the presence of anti-DNA antibodies is unknown or unexpected. Useful amounts of free DNA in an agglutination reaction will vary and useful concentrations may range from 0.1 µM or less to 1 mM or more, including but not limited to e.g., from 0.1 µM to 1 mM, 1 µM to 1 mM, 2 µM to 1 mM, 3 µM to 1 mM, 4 µM to 1 mM, 5 µM to 1 mM, 6 µM to 1 mM, 7 µM to 1 mM, 8 µM to 1 mM, 9 µM to 1 mM, 10 µM to 1 mM, 0.1 µM to 100 µM, 1 µM to 100 µM, 2 µM to 100 µM, 3 µM to 100 µM, 4 µM to 100 µM, 5 µM to 100 µM, 6 µM to 100 µM, 7 µM to 100 µM, 8 µM to 100 µM, 9 µM to 100 µM, 10 µM to 100 µM, etc. Useful free DNA in agglutination reactions (i.e., competitive DNA or blocking DNA) will generally not have significant homology to the antigen-bound polynucleotides or other polynucleotides (e.g., bridge polynucleotides, splint polynucleotides, etc.), where "significant homology is considered homology sufficient for hybridization under normal reaction conditions. Accordingly, the structure (e.g., length, nucleotide content, sequence, etc.) of such free DNA will vary widely. In some instances, the free DNA may range from 50 or less nucleotides to 100 or more, including but not limited to e.g., 50 to 100 nucleotides, 50 to 95 nucleotides, 50 to 90 nucleotides, 50 to 85 nucleotides, 50 to 80 nucleotides, 55 to 100 nucleotides, 60 to 100 nucleotides, 60 to 90 nucleotides, 60 to 80 nucleotides, 60 nucleotides, 65 nucleotides, 70 nucleotides, 75 nucleotides, 80 nucleotides, 85 nucleotides, etc. In some instances, the G/C content of the free DNA will be 50% or less including but not limited to e.g., from 30% to 50%, 35% to 50%, 40% to 50%, 45% to 50%, etc.

In some instances, a tissue sample is a blood sample. Blood samples may be analyzed as whole blood samples or may be partially or totally fractionated. In some instances, a fractionated blood sample my produce a serum sample upon which the detection methods described herein may be performed or a plasma serum sample upon which the detection methods described herein may be performed.

In some instances, a sample may be an excreted bodily fluid or semi-solid such that obtaining the sample is performed non-invasively and/or without any injury to the subject. Excreted bodily fluids and/or semi-solids of interest include but are not limited to, e.g., urine, saliva, tears, sweat, pus and stool. In some instances, the high sensitivity of the subject methods allow for detection of an antigen binding agent in an excreted bodily fluid or semi-solid where traditional agglutination methods and/or ELISA does not.

In some instances, e.g., in biotechnological and/or pharmaceutical applications, a sample may be assayed for the presence of a particular antigen binding agent and/or measured (e.g., titered) for the amount of a particular antigen binding agent as a step in the process of producing a particular antigen binding agent and/or screening the activity of an agent targeting a particular antigen binding agent. In some instances, samples in which the methods described herein find use are cellular samples generated in a laboratory. Such cellular laboratory samples may be in vitro or in vivo generated. In some instances, a cellular sample is an in vitro derived hybridoma and the subject antigen binding agent is an antibody produced by the hybridoma. In some instances, a cellular sample is an in vivo derived hybridoma and the subject antigen binding agent is an antibody produced by the hybridoma. As such, in some instances, the subject methods described herein, and the multiplexed methods described herein, find use in screening hybridomas. Hybridoma screening may be performed for the detection of a desired natural or synthetically produced antibody including but not limited to e.g., a monoclonal antibody, a polyclonal antibody, a multi-specific antibody (e.g., a bi-specific antibody), and the like. Methods of hybridoma production and analysis wherein the described methods find use will be readily apparent to the ordinary skilled artisan and include, e.g., those described in *Methods in Molecular Biology: Immunochemical Protocols*. Ed. Burns, R., Humana Press, 2005, the disclosure of which is incorporated herein by reference in its entirety.

In some instances, a cell expressing an antigen binding agent, e.g., a B-cell, a T-cell, a hybridoma cell, etc., may be identified as expressing the antigen binding agent, e.g., a B-cell receptor, a T-cell receptor, an antibody, etc., through detection of an associated elongated polynucleotide or amplification product generated according to the methods described herein. In some instances, an elongation and/or amplification product generated based on aggregation of polynucleotide-bound antigen and antigen binding agent may be detected using detectable probe nucleic acid, e.g., a fluorescently tagged probe nucleic acid, allowing identification of a cell associated with the elongation and/or amplification product. For example, in some instances, an elongation and/or amplification product generated based on aggregation of polynucleotide-bound antigen and antibody may be detected using detectable probe nucleic acid, e.g., a fluorescently tagged probe nucleic acid, allowing identification of the cell that produced the antibody. In some instances, such identification allows for the quantification of the relative binding of the antibody of the identified cell to the antigen (e.g., allowing identification of a cell producing an antibody with antigen-antibody binding or with superior antigen-antibody binding). In some instances, such identification allows for the sorting of cells (e.g., by FACS) based on their production of antibody and/or based on their production of relatively superior antibody, e.g., where multiple different cells are assayed in parallel or in multiplexed fashion.

In some instances, the method described herein find use in screening a host animal which has been immunized to generate antibodies. Any convenient host animal antibody production system may find use in combination with the methods described herein and may include but is not limited to, e.g., those subject animals described above.

As biotechnological and/or pharmaceutical applications encompass the use and/or production of monospecific and multispecific (e.g., bispecific) antigen binding members, the subject methods as described herein may generally be configured for the detection of monospecific or multispecific antigen binding agents, e.g., monospecific or multispecific antibodies (e.g., bispecific antibodies).

The above described uses are in no way to be considered limiting as the methods and compositions described herein may have additional utility not described herein.

Compositions and Kits

The instant disclosure includes compositions, e.g., reagents, kit, and devices, useful in practicing the methods described herein. Any of the reagents described herein may find use individually in a method or kit for detecting antigen binding agents. For example, the instant disclosure provides polynucleotide-bound antigens useful in the described agglutination assays.

As noted above, the polynucleotide-bound antigen may be generated by any convenient method. In some instances, the polynucleotide and the antigen may be directly linked, e.g., via a single bond, or indirectly linked e.g., through the use of a suitable linker, e.g., a polymer linker, a chemical linker, or one or more linking molecules or moieties. In some instances, attachment of the polynucleotide to the antigen may be by way of one or more covalent interactions. In some instances, the antigen may be functionalized, e.g., by addition or creation of a reactive functional group, for binding to the polynucleotide. In some instances, the polynucleotide may be functionalized, e.g., by addition or creation of a reactive functional group, for binding to the antigen. Functionalized antigens and/or polynucleotides may be modified to contain any convenient reactive functional group for conjugation. In some instances, the polynucleotide is functionalized to comprise one or more functional groups including an amine functional group, e.g., a terminal amine functional group, a carboxylic functional group, e.g., a terminal carboxylic functional group or a sulfhydryl group, a thiol functional group, e.g., as in thiolated or thiol-modified oligonucleotides, and the like.

In instances where a polynucleotide is functionalized with an amine functional group and/or a carboxylic functional group and/or a sulfhydryl group and the antigen is a polypeptide antigen, the functionalized polynucleotide and the polypeptide antigen may be conjugated by any convenient method of protein conjugation including but not limited to protein crosslinking including but not limited to, e.g., glutaraldehyde crosslinking, carbodiimide crosslinking, succinimide ester crosslinking, imidoester, crosslinking, maleimide crosslinking, iodoacetamide crosslinking, benzidine crosslinking, periodate crosslinking, isothiocyanate crosslinking, and the like. Such conjugation methods may optionally use a reactive sidechain group of an amino acid residue of the polypeptide antigen (e.g., a reactive side-chain group of a Lys, Cys, Ser, Thr, Tyr, His or Arg amino acid residue of the protein, i.e., a polypeptide linking group may be amino-reactive, thiol-reactive, hydroxyl-reactive, imidazolyl-reactive or guanidinyl-reactive). In some cases, a chemoselective reactive functional group may be utilized that conjugates to a compatible function group on the polynucleotide. Chemoselective reactive functional groups for inclusion in the subject polypeptide antigen include, but are not limited to: an azido group, an alkynyl group, a phosphine group, a cysteine residue, a C-terminal thioester, aryl azides, maleimides, carbodiimides, N-hydroxysuccinimide (NHS)-esters, hydrazides, PFP-esters, hydroxymethyl phosphines, psoralens, imidoesters, pyridyl disulfides, isocyanates, aminooxy-, aldehyde, keto, chloroacetyl, bromoacetyl, and vinyl sulfones. Further exemplary functional groups and crosslinking methods and methods of conjugation using such functional groups are described in, e.g., Hermanson, "Bioconjugate Techniques" 2nd Edition, Academic Press, 2008, the disclosure of which is incorporated herein by reference in its entirety.

Depending on the particular functional groups present, whether naturally occurring or synthetic, on the antigen and polynucleotide to be conjugated, in some instances, useful conjugation reagents may include but are not limited to e.g., homobifunctional conjugation reagents (e.g., (Bis(2-[Succinimidooxycarbonyloxy]ethyl) sulfone, 1,4-Di-(3'-[2'pyridyldithio]-propionamido) butane, Disuccinimidyl suberate, Disuccinimidyl tartrate, Sulfodisuccinimidyl tartrate, Dithiobis(succinimidyl propionate), 3,3'-Dithiobis (sulfosuccinimidyl propionate), Ethylene glycol bis(succinimidyl succinate), and the like), heterobifunctional conjugation reagents (e.g., m-Maleimidobenzoyl-N-hydroxysuccinimide ester, m-Maleimidobenzoyl-N-hydroxysulfosuccinimide ester, N-γ-Maleimidobutyryloxysuccinimide ester, N-γ-Maleimidobutyryloxysulfosuccinimide ester, N-(ε-Maleimidocaproic acid) hydrazide, N-(ε-Maleimidocaproyloxy) succinimide ester, N-(ε-Maleimidocaproyloxy) sulfo succinimide ester, N-(ρ-Maleimidophenyl) isocyanate, N-Succinimidyl(4-iodoacetyl)aminobenzoate, Succinimidyl 4-(N-maleimidomethyl) cyclohexane-1-carboxylate, Succinimidyl 4-(ρ-maleimidophenyl) butyrate, N-Sulfosuccinimidyl(4-iodoacetyl)aminobenzoate, Sulfosuccinimidyl 4-(N-maleimidomethyl) cyclohexane-1-carboxylate, Sulfo succinimidyl 4-(ρ-maleimidophenyl) butyrate, 1-Ethyl-3-(3-dimethylaminopropyl) carbodiimide hydrochloride, 1-Ethyl-3-(3-dimethylaminopropyl) carbodiimide hydrochloride, Maleimide PEG N-hydroxysuccinimide ester, and the like), photoreactive conjugation reagents (e.g., p-Azidobenzoyl Hydrazide, N-5-Azido-2-nitrobenzyloxysuccinimide, p-Azidophenyl glyoxal monohydrate, N-(4-[p-Azidosalicylamido]butyl)-3'-(2'-pyridyldithio) propionamide, Bis (β-[4-azidosalicylamido]-ethyl) disulfide, N-Hydroxysuccinimideyl-4-azidosalicyclic acid, N-Hydroxysulfosuccinimidyl-4-azidobenzoate, Sulfosuccinimidyl 2-(7-azido-4-methylcoumarin-3-acetamide)ethyl-1,3-dithiopropionate, Sulfosuccinimidyl 2-(m-azido-o-nitrobenzamido)-ethyl-1, 3'-propionate, Sulfosuccinimidyl 6-(4'-azido-2'-nitrophenylamino)hexanoate, Sulfosuccinimidyl (4-azidophenyl dithio)propionate, Sulfosuccinimidyl-2-(p-azidosalicylamido)ethyl-1,3-dithiopropionate, and the like).

In instances where a polynucleotide is functionalized with a thiol functional group (e.g., a thiolated oligonucleotide), conjugation to an antigen of interest may be achieved through the use of sulfo-sulfosuccinimidyl 4-(N-maleimidomethyl)cyclohexane-1-carboxylate (sulfo-SMCC) conjugation as described herein.

In instances where a polynucleotide is conjugated to a small molecule, any convenient method of conjugation may find use in covalently attaching the polynucleotide to the small molecule depending on various factors including e.g., available reactive groups on the small molecule and the presence or absence of particular modifications on the polynucleotide. In some instances, amine functionalized polynucleotide may be conjugated to a desired small molecule via an amine-reactive crosslinker including but not limited to e.g., NHS ester including e.g., as described herein.

In some instances, attachment of the polynucleotide to the antigen utilizes existing functional moieties already present on the polynucleotide. In some instances, a functional moiety utilized in conjugating the polynucleotide to the antigen is added to a polynucleotide to generate a functionalized polynucleotide. Functionalized polynucleotides may be generated by modifying one or more nucleotides of the polynucleotide or by adding a modified nucleotide to the polynucleotide. Such modified nucleotides may, in some instances, be referred to as functionalized nucleotides.

Modified nucleotides may be introduced into the polynucleotide by any convenient method including but not limited to, e.g., synthetic/chemical synthesis (e.g., solid-phase oligonucleotide synthesis, phosphoramidite synthesis, etc.), recombinant synthesis, enzymatic incorporation, and the like. Modified nucleotides and nucleotide modifications useful in forming an attachment to an antigen of interest include but are not limited to, e.g., those useful in Click-Chemistry functionalization (e.g., azide-functionalized, alkyne-functionalized, dibenzocyclooctyne (DBCO) functionalized, etc.), those useful in nucleic acid labeling, those useful in photocrosslinking, those useful in acrylic phosphoramidite linking, those useful in pyrophosphate linking/ligation, and the like, such as, e.g., 3'-Azido-2',3'-dideoxyadenosine-5'-Triphosphate, 5-(3-Azidopropyl)-uridine-5'-triphosphate, 5-Ethynyl-2'-uridine 5'-triphosphate, 8-Azido-adenosine-5'-triphosphate, $N^6$-(6-Azido)hexyl-3'-deoxyadenosine-5'-triphosphate, Cytidine-5'-phosphate-3'-(15-azido-4,7,10,13-tetraoxa-pentadecanoyl-6-aminohexyl) phosphate, γ-(2-Azidoethyl)-adenosine-5'-triphosphate, γ-(6-Azidohexyl)-adenosine-5'-triphosphate, γ-[(6-Azidohexyl)-imido]-adenosine-5'-triphosphate, $N^6$-(6-Azido) hexyl-adenosine-5'-triphosphate, $N^6$-(6-Azido)hexyl-2'-deoxy-adenosine-5'-triphosphate, $N^6$-(6-Azido)hexyl-3'-deoxyadenosine-5'-triphosphate, 3'-Azido-2',3'-dideoxythymidine-5'-triphosphate, 5-(15-Azido-4,7,10,13-tetraoxa-pentadecanoyl-aminoallyl)-2'-deoxyuridine-5'-triphosphate, $N^6$—Propargyl-adenosine-5'-triphosphate, Adenosine-5'-[γ-(propargyl)]triphosphate, Adenosine-5'-[γ-(propargyl)-imido]triphosphate, 2-Ethynyl-adenosine-5'-triphosphate, 5-(Octa-1,7-diynyl)-2'-deoxycytidine 5'-triphosphate, 5-(Octa-1,7-diynyl)-2'-deoxyuridine 5'-triphosphate, 5-Ethynyl-2'-deoxyuridine 5'-triphosphate, 5-Dibenzylcyclooctyne-2'-deoxyuridine 5'-triphosphate, 2-Aminopurine-2'-deoxyriboside-Triphosphate, 5-Aminoallyl-2'-deoxycytidine-5'-Triphosphate, 5-Aminoallyl-2'-deoxyuridine-5'-Triphosphate, 5-Propargylamino-2'-deoxycytidine-5'-Triphosphate, 5-Propargylamino-2'-deoxyuridine-5'-Triphosphate, 5-Iodouridine-5'-Triphosphate, 4-Thiouridine-5'-Triphosphate, 5-Bromouridine-5'-Triphosphate, 5'-Acrydite modification, 5'-adenylation modification, and the like.

In some instances, attachment of a polynucleotide to an antigen of interest is mediated by one or more functional linkers. A functional linker, as used herein, refers to any suitable linker that has one or more functional groups for the attachment of one molecule to another. For example, in some instances a nucleotide of a polynucleotide of the subject disclosure may be attached to a biomolecule linker that comprises a functional group (e.g., an amino functional group, a thiol functional group, a hydroxyl functional group, an imidazolyl functional group, a guanidinyl functional group, an alkyne functional group, an azide functional group, a strained alkyne functional group, etc.). As a non-limiting example, a nucleotide of a polynucleotide of the subject disclosure may biotinylated with functional biotin that comprises a functional group.

In some instances, those modified nucleotides useful in attachment of a polynucleotide to a desired antigen may include those available from commercial suppliers, including but not limited to, e.g., Integrated DNA Technologies, Inc. (Coralville, IA), TriLink BioTechnologies, Inc. (San Diego, CA), Jena Bioscience GmbH (Jena, Germany), Life Technologies, Inc. (Grand Island, NY), New England Biolabs, Inc. (Ipswich, MA), Zymo Research Corporation, (Irvine, CA), Enzo Life Sciences, Inc. (Farmingdale, NY), and the like.

Generation of the polynucleotide conjugated antigens of the instant disclosure may take into account the efficiency of the conjugation reaction which influences the molar ratio of antigen to polynucleotide, e.g., antigen:DNA molar ratio, following conjugation. The inventors of the instant disclosure have discovered that the molar ratio of antigen to polynucleotide impacts agglutination in the described assay. Without being bound by theory, low antigen to high polynucleotide ratios appear, in some instances, to inhibit agglutination (e.g., by inhibiting access of the binding surfaces of the antigen and the antigen binding agents). In many instances, the antigen-to-polynucleotide molar ratio following conjugation will be greater than 1:5, including but not limited to e.g., greater than 1:4, greater than 1:3, greater than 1:2, etc. In certain instances, the antigen-to-polynucleotide molar ratio following conjugation will range from 1:1 to 1:5 including but not limited to e.g., 1:1 to 1:4, 1:1 to 1:3, 1:1 to 1:2, etc. In other instances, the molar ratio of antigen to polynucleotide following conjugation, for use in an agglutination assay as described, is essentially 1:1, essentially 1:2, essentially 1:3, and the like.

The instant disclosure also provides devices related to the subject agglutination assays and detection of the described antigen binding agents. Such devices may include, but are not limited to "field-use" devices, e.g., dipstick assay devices, lateral-flow assay devices, slide-based devices, and the like, that may allow performing the herein described agglutination assays with minimal or no laboratory amenities, such as, e.g., electricity, chemical reagents, temperature control, refrigeration, etc. Also included are devices for use in the laboratory setting, e.g., those devices utilizing precise quantification of the produced amplification product, including, e.g., PCR devices, qPCR devices, fluorimeters, scintillation counters, microscopes, plate-readers, nucleic acid sequencing devices, etc. In some instances, isothermal amplification devices, such as those described in Cheng et al. (2012) Sensors 12, 8319-8337, the disclosure of which is incorporated herein by reference in its entirety, may be modified for use as devices for practicing the methods as described herein.

In yet another aspect, the present disclosure provides kits for practicing the subject methods, e.g., as described above. The subject kits may include any combination of the herein described reagents, devices, or compositions useful in practicing the methods as described above including but not limited to, e.g., one or more of the described polynucleotide-bound antigens, bridging polynucleotides, splint polynucleotides, enzymatic reagents (e.g., ligases), and the like. Subject kits may further include one or more reagent preparation reagents including but not limited to, e.g., reagents for functionalizing an antigen (including e.g., functionalized polynucleotides for readily conjugating the polynucleotide to an antigen of interest), reagents for functionalizing a polynucleotide (e.g., a functionalized nucleotide (i.e., a nucleotide that includes one or more reactive groups), reagents for conjugation of a polynucleotide and/or an antigen (including e.g., one or more conjugation and/or crosslinking reagents or linkers as described herein).

In addition, subject kits may further include assay reagents or reagents useful in performing an assay of a sample, e.g., a patient sample, to allow for an assessment, e.g., of whether one or more antigen binding agents are present in a sample from the subject. Such assay reagents may include but are not limited to, e.g., detection reagents, sample preparation reagents, amplification reagents (e.g., PCR reagents and/or isothermal amplification reagents and/or qPCR reagents, etc.) and agglutination reagents (e.g., polynucleotide-bound antigen, and the like), buffers, diluents, etc. Such assay kits may further include sample collection components, e.g., sample collection containers and/or sample collection devices, etc. The above components may be present in separate containers or one or more components may be combined into a single container, e.g., a glass or plastic vial or tube.

Kits may further include control reagents and samples including but not limited to, e.g., control samples (e.g., positive control samples, negative control samples, etc.) calibration reagents (e.g., fluorescent calibration reagents, etc.).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, removable drive (e.g., flash memory device), etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

In the following examples the methods and materials provided here were generally applied unless designated otherwise or obviously irrelevant:

The biotin-DNA conjugate was purchased as-is from Integrated DNA Technologies. The DNP-DNA conjugate synthesis was achieved by reacting amine-DNA (5' or 3') (Coralville, Iowa) with the corresponding succinimidyl ester in large excess and purified by serial ethanol precipitations (see below). The protein-DNA conjugates were prepared by lysine-to-thiol crosslinking with sulfo-SMCC (sulfosuccinimidyl 4-(N-maleimidomethyl)cyclohexane-1-carboxylate). Briefly, lysines were activated with maleimides by incubation with SMCC in PBS. Thiol-DNA (5' or 3') was reduced with DTT and then incubated with the maleimide-functionalized protein overnight at 4° C. (see below for more detail). Characterization of the small molecule-DNA conjugates was achieved by high resolution mass spectrometry while protein-DNA conjugates were analyzed by Polyacrylamide gel electrophoresis (PAGE) and silver stain to observe the appropriate mass shift.

Synthesis of Antigen-DNA Conjugates

Figure 20:
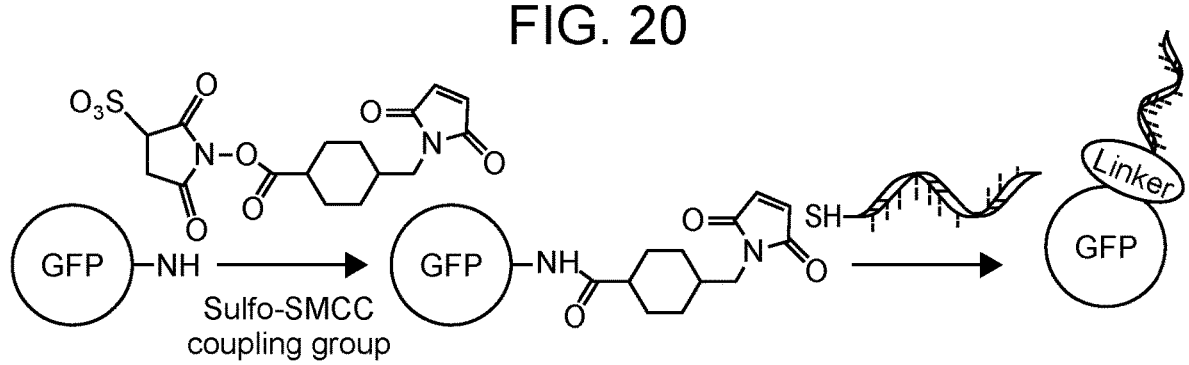
FIG. 20 provides a schematic representation of the conjugation of a polynucleotide to a GFP antigen and the efficiencies of such conjugation reactions as analyzed by silver staining.
Figure 20:
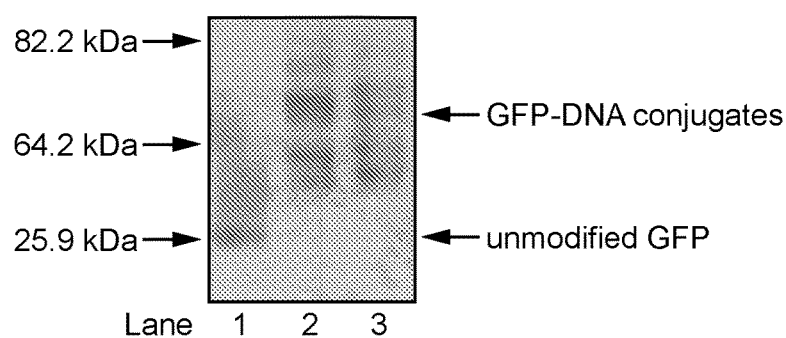

Insulin-DNA conjugate was synthesized by resuspending recombinant insulin (Sigma-Aldrich) to make a 1 mg/mL solution in reaction buffer (55 mM sodium phosphate, 150 mM sodium chloride, 20 mM EDTA, pH 7.2). One µL of a 4 mM solution of sulfo-SMCC (Pierce Biotechnologies) in anhydrous DMSO was added to 10 µL of the protein solution and incubated at RT for 2 h. Thiolated-DNA (IDT) was resuspended to 100 µM in reaction buffer. Three microliters of the 100 µM thiolated-DNA stock was then added to 50 µL of reaction buffer. To this solution, 4 µL of a 100 mM solution of DTT (Life Technologies) was added to reduce the oxidized thiolated-DNA. The solution was then incubated at 37° C. for 1 h. 7 k molecular weight cut off (MWCO) gel microspin columns (Life Technologies) were equilibrated with reaction buffer. The reduced oligonucleotides were desalted by the equilibrated microspin columns twice. Unreacted sulfo-SMCC was removed from the insulin solution by a 3 k MWCO centrifugal filter column (EMD Millipore) to a final volume of 60 µL. The thiolated-DNA and insulin solutions were then mixed, reacted overnight at 4° C., and then purified by 10 k MWCO filter column. Conjugate concentrations were determined by BCA assay (Life Technologies). Conjugation efficiencies were analyzed by SDS-PAGE and silver staining. A representative silver-stain is shown in FIG. 20 (Samples were resolved by SDS-PAGE and then total protein/DNA was visualized by silver staining. Lane 1 is unmodified GFP, lane 2 is GFP-2A conjugate and lane 3 is GFP-2B conjugate. A significant mass shift was observed in lanes 2 and 3 due to the addition a 14 kD oligonucleotide to the protein. Laddering of lanes 2 and 3 is a result of the addition of multiple oligonucleotides to a single protein) along with a schematic of the reaction schemes for GFP-DNA conjugation by sulfo-SMCC. DNA-to-antigen ratios of the conjugates were estimated by UV-vis absorption. Antigen-DNA conjugates were stored at 4° C. for short-term usage or aliquoted for long-term storage at −80° C. GFP-, mouse-IgG-, and thyroglobulin-DNA conjugates were synthesized similarly with slight modifications. Briefly, unreacted SMCC was filtered by 7 k MWCO gel microspin columns. Conjugates were purified from unconjugated DNA by centrifugal filter columns (GFP, 30 k MWCO column; mouse IgG, 100 k MWCO column; thyroglobulin, 100 k MWCO column).

Finally, biotin-DNA conjugates was purchased from IDT. DNP-DNA conjugates were synthesized as follows. Twenty five milligrams DNP-NHS ester (Life Technologies) was dissolved in anhydrous DMSO to make a 50 mM solution. 5' or 3' amine functionalized DNA (IDT) was resuspended in ddH2O to make a 1 mM solution. 40 µL of the 1 mM DNA solution was added to 300 µL of PBS with 50 mM NaHCO$_3$. 80 µL of the NHS ester solution was added over 2 days at RT under constant rotational mixing. Modified DNA was then precipitated by adding 2.5 vol of ethanol and 0.1 vol of 10 M ammonium acetate and then incubated for 4 h. Precipitated DNA was pelleted by centrifugation for 15 min at 4° C., followed by a gentle wash in ice cold 70% ethanol-H2O. The pellet was then resuspended in 100 µL of ddH2O and then purified again by precipitation as before to ensure complete removal of unreacted small molecules. After the second precipitation, the pellet was diluted in ddH2O to make a 100 µM stock solution, which was stored at −20° C. until used. Synthesis was confirmed by high resolution LC-MS.

Antibody Detection by Agglutination-PCR (ADAP).

One fmole of paired antigen-DNA conjugates was resuspended in 2 µL of incubation buffer C (2% BSA, 0.2% Triton X-100, 8 mM EDTA in PBS). Two microliters of analyte was added to the conjugates and then incubated at 37° C. for 30 min. 116 µL of ligation mix (20 mM Tris, 50 mM KCl, 20 mM MgCl2, 20 mM DTT, 25 µM NAD, 0.025 U/µL ligase, 100 nM bridge oligo, 0.01% BSA, pH=7.5) was added, and then incubated at 30° C. for 15 min. Ten microliters uracil-excision mix (0.025 U/µL Epicenter Bio) was added and incubated for 15 min at 30° C. Twenty-five microliters of the solution was added to 25 µL of 2×PCR Master Mix (Qiagen) with 10 nM primers and then amplified by PCR (95° C. for 10 min, 95° C. for 15 s, 60° C. for 30 s 12 cycles). The reaction was then diluted 1:20 in ddH2O. 8.5 µL of the diluted PCR samples were added to 10 µL of 2×qPCR Master Mix (Life Technologies) with 1.5 µL of primers (final concentration 690 nM). qPCR was performed on either a Bio-Rad CFX96 or a Bio-Rad iQ5 real-time PCR detection system.

The ADAP assays for affinity purified anti-insulin (Abcam), anti-biotin (Abcam), anti-GFP (Vector Laboratories), and anti-mouse IgG antibodies (Pierce Biotechnologies) were carried out as described above with the following modifications. For dilution in buffer, 2 µL of antigen-DNA conjugates was mixed with 2 µL of serial diluted antibodies (concentration range: $10^2$-$10^{-4}$ m/mL) in buffer C or buffer only (blank). For dilution in fetal bovine serum (Sigma-Aldrich), antibodies were spiked in fetal bovine serum to obtain 2 wt %/wt antibodies solution, which was then serial diluted in buffer C (concentration range: $10^2$-$10^{-4}$ m/mL) for ADAP assay. Isotype antibodies (Santa Cruz Biotech) subjected to the same preparation were analyzed side-by-side as negative controls.

ADAP Detection Assay for Anti-DNP Antibodies from Antiserum.

The ADAP PCR detection assay for anti-DNP antiserum (Abcam) was carried out as described above with the following modifications. Anti-DNP antiserum was obtained from rabbit inoculated with DNP-conjugated carrier proteins without further purification. Two microliters of DNP-DNA conjugates was mixed with 2 µL of serial diluted anti-DNP antiserum (concentration range: 0.4-0.0002 mg/mL) in buffer C for ADAP detection.

ADAP Detection Assay for Anti-Thyroglobulin Patient Plasma.

The ADAP detection assay for anti-thyroglobulin positive patient plasma (ImmunoVision) was carried out as described above with the following modifications. Two microliters of thyroglobulin-DNA conjugates were mixed with 2 µL of serially diluted patient plasma (dilution factor: $10^0$-$10^6$) in buffer C for ADAP detection.

Multiplexed ADAP for Anti-Biotin and Anti-Mouse IgG Antibodies.

The multiplex ADAP assay for anti-biotin and anti-mouse IgG antibody was carried out as described above with the following modifications. 1 µL of biotin-DNA conjugates (sequence 1 as in Table 2) and 1 µL mouse-IgG-DNA conjugates (sequence 2 as in Table 2) are mixed with 2 µL of serial diluted either (1) anti-biotin antibodies (concentration range: $10^2$-$10^{-4}$ µg/mL) in buffer C or buffer only (blank) (2) anti-mouse antibodies (concentration range: 102-

10-4 µg/mL) in buffer C or buffer only (blank) (3) both anti-biotin and anti-mouse antibodies (concentration range: 102-10-4 µg/mL) in buffer C or buffer only (blank). The antigen and antibody mixtures were processed and analyzed as described above.

Multiplexed ADAP and PLA Detection for Anti-Biotin Antibodies and Total IgG.

ADAP and PLA19-22 (proximity ligation assay) were used in conjunction to quantify the specific antibodies and total antibodies amounts in a given sample. The multiplex ADAP detection assay for anti-biotin and total IgG was carried out as described above with the following modifications. 1 µL biotin-DNA conjugates (sequence 1) and 1 µL anti-goat-IgG-DNA conjugates (sequence 2) are mixed with 2 µL of serially diluted either (1) goat anti-biotin antibodies (concentration range: $10^2$-$10^{-4}$ m/mL) in buffer C or buffer only (blank) (2) goat IgG (concentration range: $10^2$-$10^{-4}$ m/mL) in buffer C or buffer only (blank) (3) both antibiotin and goat IgG in buffer C, where total IgG is fixed at 0.7 µg/mL and anti-biotin antibodies fraction varied from 100%-0% or buffer only (blank). The antigen and antibody mixtures were processed and analyzed as described above.

Direct ELISA Detection of Anti-Insulin Antibodies.

Recombinant human insulin (Sigma) was resuspended to 1 mg/mL in PBS. 75 µL of the insulin solution was added to wells of an enzyme-linked immunosorbent assay (ELISA) plate (Santa Cruz Biotech). The plate was covered with a plastic membrane, and the insulin was allowed to adsorb to the plate overnight at 4° C. Excess supernatant was decanted, and the wells were blocked with 5% BSA in PBS overnight at 4° C. Anti-insulin antibodies were diluted into PBS and allowed to bind at RT for 1 h. The supernatant was decanted and the wells were washed 4× with PBS. Secondary antibody-HRP probes (Santa Cruz Biotech) were diluted 1:5000 in 5% BSA in PBS and added to the wells and allowed to incubate at RT for 1 h. The supernatant was decanted and then washed 4× in PBS. 50 µL of TMB substrate solution as added and allowed to develop for 15 min and then quenched by addition of 50 µL of 2 M $H_2SO_4$. Absorbance was read at 450 nm in a plate reader.

Circumventing Interference from Anti-DNA Antibodies.

Anti-DNA antibodies positive patient plasmas were purchased from ImmunoVision. ADAP detection of anti-DNA plasma was carried out as described above with slight modifications. For detection of anti-GFP antibodies, anti-GFP antibodies are spiked into anti-DNA and normal plasma. A sample of 2 µL serial diluted anti-GFP solution is incubated with 2 µL solution containing GFP-DNA conjugates and with or without 100 µM competition DNA. The competition DNA is purchased from IDT with the sequence:

(SEQ ID NO: 1)
GGCCTCCTCCAATTAAAGAATCACGATGAGACTGGATGAATCACGGTAG

CATAAGGTGCAGTACCCAAATAACGGTTCAC.

Radioimmunoassay and Electrochemiluminescent Assays for Anti-Thyroglobulin Autoantibodies.

Tg-RIAs (Kronus), the Beckman Access TgAb (Beckman Coulter) and Roche Elecsys TgAb (Roche Diagnostics) were performed per the manufactures' instructions. These assays are standardized against WHO reference serum 65/93.

Data Analysis.

Figure 21:
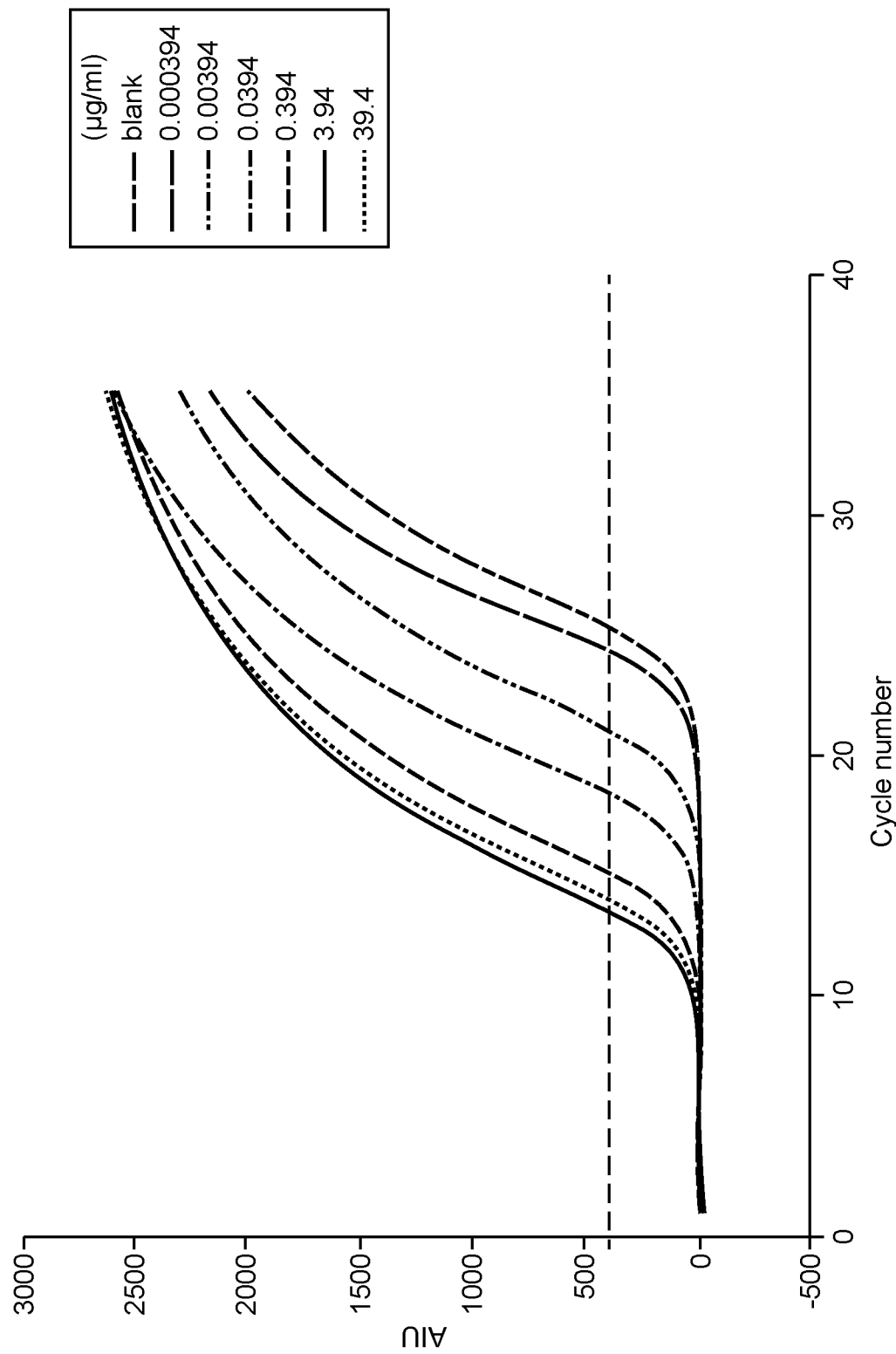
FIG. 21 provides a representative real-time qPCR measurement plot according to one embodiment of the instant disclosure.

Three replicate ADAP measurements were carried out for each antibody sample in buffer C in addition to a blank. The replicates were measured by taking aliquots from the same dilution series and the same preparation of ligation, excision and preamplification steps but placing them in three different wells for qPCR analysis. A representative real-time qPCR measurement plot taken from an ADAP assay for the serial dilution of an anti-biotin antibody is shown in FIG. 21 (dashed line is threshold fluorescence value). A single threshold fluorescence value was automatically chosen by Bio-Rad software. For each curve, the PCR cycle number with the fluorescence value corresponding to the chosen threshold value was defined as the cycle threshold (Ct) value. $\Delta Ct$ is defined as the Ct value of the blank minus the Ct value of the samples. The value of $\Delta Ct$ is proportional to the initial amplicon concentration. This amplicon concentration is then also proportional to the amount of target antibodies present in the initial dilution series. A volume of 2 µL from each serial dilution series was taken for ADAP measurement. Thus, the number of antibody molecules in each measurement is ($2 \times 10^{-6}$ L)×antibody concentration (M)×Avogadro's number. A nonlinear four parameter logistic fit for an antibody dilution series is determined using custom software. The limit of detection for the ADAP assay is defined as the average $\Delta Ct$ value of the buffer C only blank plus 3 standard deviations of the blank. The value of each limit of detection is calculated relative to the corresponding blank.

Intra-Assay and Interassay Variation for ADAP

The intra-assay variation for ADAP was determined by repeating ADAP measurements in triplicate for anti-GFP antibodies six times on the same plate. The intra-assay variation is defined as standard deviation of the triplicate divided by mean of the triplicate and is consistently <1%. The interassay variation for ADAP is evaluated by measuring anti-GFP antibody concentrations in triplicate on five different plates on different days. The interassay variation defined by standard deviation of the concentrations from five different plates divided by the mean of concentrations from five different plates and is <3%. Both the intra-assay and interassay variation of ADAP are far below the accepted biomedical assay variation values, which are 10% and 15% respectively. ADAP's superior intra-assay and interassay performance is likely a result of having fewer overall handling steps, no wash steps, and no centrifugation steps. The extensive washing and centrifuging requirements for other assays might compromise their precision and reproducibility.

Figure 8:
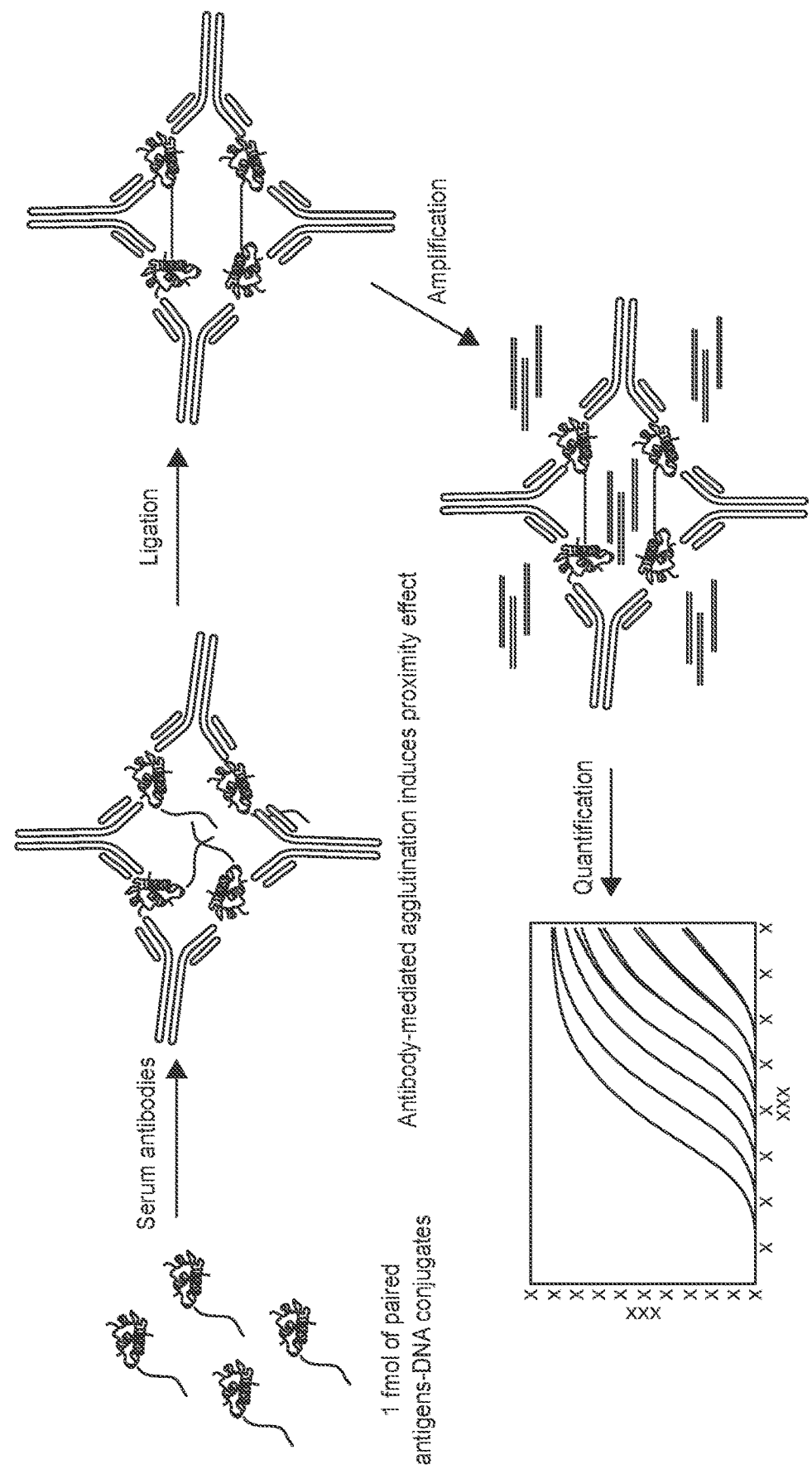
FIG. 8 depicts a schematic of antibody detection by Sensitive Immune Complex Monitoring Platform by Agglutination-Ligation.

Example 1: PCR-Based Agglutination-Ligation Assay Detection of Insulin, DNP, IgG, and Thyroglobulin Antibodies In the agglutination-ligation assay, dubbed "SIMPAL" (Sensitive Immune Complex Monitoring Platform by Agglutination-Ligation) and also referred to as "ADAP" (Antibody Detection by Agglutination-PCR), a PCR amplicon was split into two halves each bearing a primer site. Each half was covalently attached to a recombinant antigen, with the downstream fragment bearing a 5' phosphate group to render it a substrate for DNA ligase. In this assay, 1-2 µL of these antigen-DNA conjugates were incubated at picomolar concentrations with antibodies that bind to and aggregate the antigen-DNA conjugates. The aggregated conjugates are held close to one another, facilitating ligation of the two halves upon treatment with DNA ligase and a short bridging oligonucleotide. Antigen-DNA conjugates left unbound are too dilute to allow ligation. The reconstituted PCR amplicon was then pre-amplified and quantified by fluoresence-based quantitative PCR (FIG. 8).

In this antibody detection experiment, 1 fmol of each antigen-DNA conjugate was diluted in 2 μL of buffer and added to a sample and incubated to allow binding. Next, 120 μL of a ligation mixture containing DNA ligase and a bridging oligonucleotide were added and incubated at 30° C. for 15 minutes. This ligation mixture was diluted and pre-amplified by 13 rounds of PCR in a standard thermocycler. The resulting PCR products are diluted and analyzed by qPCR.

A dose-dependent response to the concentration of a-insulin antibody was observed over five orders of magnitude (e.g., see FIG. 9A) when incubated with insulin-DNA conjugates. Very similar results were obtained in different biological diluents, indicating that the test can work in complex mixtures, as shown by results generated with antibodies diluted in PBS, bovine serum and human saliva. No significant variation was observed. The detection limit in serum was 170 zeptomoles of antibody with a concentration of 15 pg/mL. Incubation with the corresponding isotype control yielded no signal in any case. A panel of protein and small molecule hapten antigen-DNA conjugates such as GFP, Mouse-IgG, and biotin were tested and similar detection limits were found (Table 1 provided in FIG. 10).

Figure 9A:
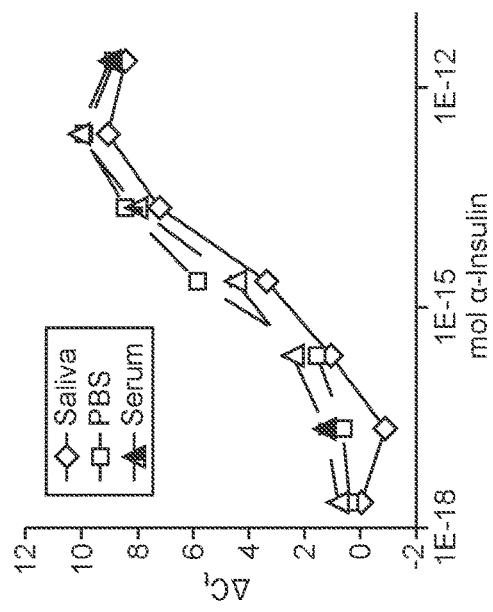
FIG. 9A-9J depict the high sensitivity, with various sample types and targets, and the amenability to multiplexing, of agglutination-mediated antibody detection.

Whole DNP antisera was also used to agglutinate DNP-DNA conjugates. Analysis with ADAP was able to detect agglutination in rabbit serum from as little as 0.74 ng of total antiserum protein (FIG. 9J). This result demonstrates that ADAP can sensitively detect natively produced antibodies from whole serum and has the potential to detect antibodies to small molecules, which pose certain difficulties in conventional detection assays.

Figure 9B:
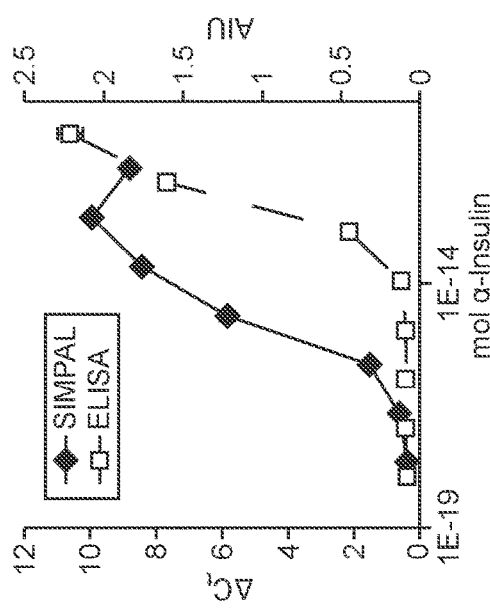

To benchmark the sensitivity of this assay against a well-known standard, a comparison with direct ELISA was performed and an 865-fold improvement of the detection limit was found (FIG. 9B and Table 1). The specificity of ADAP was determined by assaying samples containing isotype control antibodies, which yielded no detectable signal (FIG. 9G). In addition, no detectable signal was observed when the assay was performed with irrelevant antigen-DNA conjugates (FIG. 9H).

The assay was also performed in a multiplex configuration. Due to the sequence space available to detect nucleic acids, arbitrary sequences can be designed and designated to report on the agglutination of different antigens. This is useful for several reasons. For example, many diseases such as type 1 diabetes have multiple autoantibody biomarkers (e.g., Insulin, islet antigen 2 (IA-2), Glutamic acid decarboxylase (GAD), Zinc transporter 8 (ZnT8)). One can simultaneously and separately detect antibodies against multiple antigens using specific nucleic acids bound to different antigens to increase confidence in diagnosis. An additional advantage of the multiplexed embodiment of this assay allows for antibody tests to take into account total immunoglobulin concentration which is typically overlooked in conventional antibody testing. Overlooking immunoglobulin concentration can lead to false negatives results for patients with immunoglobulin deficiency, a common problem, e.g., for patients with Celiac's disease. Using a coupled assay to detect immunoglobulin levels in addition to other target antibodies can ferret out negative results that are the result of abnormally low immunoglobulin levels.

A set of orthogonal antigen-DNA conjugates with biotin and mouse IgG were generated. These amplicons were designed such that Set 1 primers did not amplify the Set 2 amplicon and vice versa, but share a common bridging oligonucleotide (see Table 2). Antigen-DNA conjugates were synthesized as before, labeling the Set 1 oligos with biotin and labeling the Set 2 oligos with mouse IgG. The two antigen-DNA conjugates were pooled and then incubated with antibodies that bind either only biotin, only mouse IgG, or both and then analyzed for agglutination. The sample incubated with the anti-biotin antibodies showed signal only with Set 1 primers, while the sample incubated with the anti-mouse IgG antibodies showed signal only in the Set 2 primers. The mixed sample generated signal with both sets of primers (FIG. 9D, see also FIG. 14A-14C).

To multiplex detection of total IgG and antibody, anti-IgG proximity probes were generated from a single batch of anti-IgG polyclonal antibodies. The batch was split into two and each pool was modified with either the upstream or downstream fragment of the Set 2 PCR amplicon. The two halves of the amplicon are brought close together when the polyclonal antibodies bind nearby epitopes, allowing for ligation and detection by PCR. Goat α-biotin antibodies were diluted into goat IgG such that the total amount of IgG remained constant, but the fraction of IgG that is α-biotin varied. qPCR analysis with the Set 2 primers showed no change in signal, corresponding to the constant concentration of IgG in every sample, whereas signal generated from the Set 1 primers increased as the fraction of α-biotin antibodies increased (FIG. 9I). This data shows that detection of the total antibody levels can be multiplexed with detection of antigen-specific antibodies.

The detection of diagnostic antibodies from patient samples was tested. Thyroglobulin autoantibodies mediate and are diagnostic of autoimmune thyroiditis. Also, following therapeutic thyroidectomy in response to cancer, thyroglobulin titers are often used as a sentinel to ensure complete removal of the offending tumor. Thyroglobulin autoantibodies can interfere with thyroglobulin assays and thus represent an important biomarker for monitoring recovery. Currently, radioimmunoassays remain the gold standard for detecting Thyroglobulin autoantibodies.

SIMPAL analysis was performed with thyroglobulin-DNA conjugates on pooled healthy human plasma in comparison to plasma from patients that tested positive for thyroglobulin autoantibodies. A robust signal from the thyroglobulin-positive samples (2 μl) was observed even after 1:100,000 dilution, with nearly no background from the healthy sample (FIG. 9E). Identical samples were assayed using three FDA-approved clinical laboratory assays: the Kronus/RSR radioimmunoassay and two electrochemiluminescence assays (Beckman Coulter and Roche). Impressively, ADAP detected antithyroglobulin antibodies with a detection limit 3-4 orders of magnitude lower than these standard assays (FIG. 9F).

In conclusion, the developed assay uses PCR to detect antibodies present in complex mixtures. The assay rivals or surpasses the reported detection limit of ELISAs with the ability to detect down to zeptomoles of antibody in a 2 μL sample. As a homogeneous, solution phase immunoassay, agglutination-ligation assay circumvents the protein denaturation and epitope masking problems of surface-immobilized antigen assays. As a no-wash immunoassay, it removes the tedious optimization of washing steps that hamper ELISA development. The developed assay does not require isolation of uniquely paired antibodies as required for a sandwich ELISA. Significantly, this assay can be performed with only standard qPCR equipment and reagents which are readily available in many clinical settings. The assay uses ultralow quantities of an antigen-DNA conjugate (~1.7 million assays from 100 μg of a 60 kDa antigen conjugate) and standard ligation enzymes.

FIG. 8. Antibody detection by SIMPAL or ADAP. Antigen-DNA conjugates are incubated with antibody-containing analyte. The antibodies bind to and agglutinate the conjugates, positioning them in a favorable position for ligation upon the addition of a bridging oligonucleotide and DNA ligase. The bridging oligonucleotide is hydrolyzed and the new amplicon is pre-amplified by PCR. The pool is then analyzed by qPCR to determine the relative antibody levels.

Figure 9C:
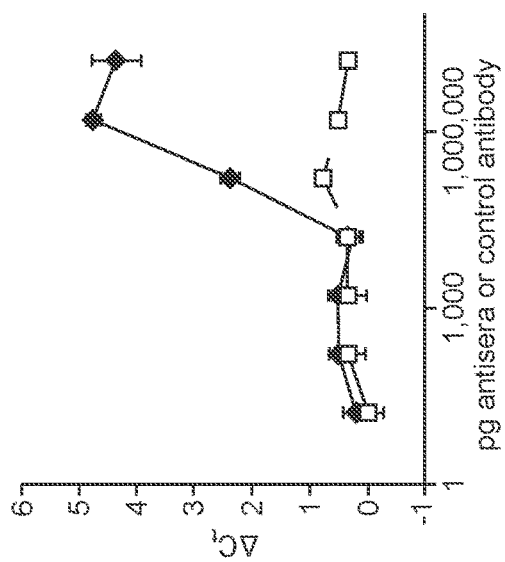
Figure 9E:
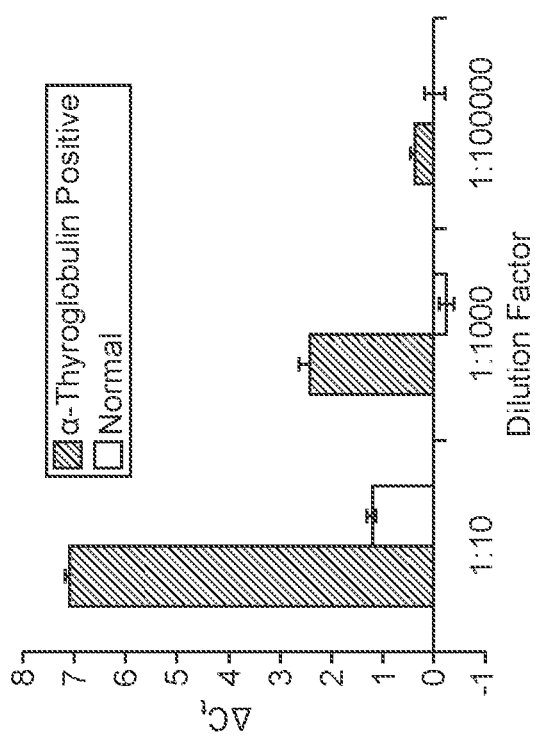
Figure 9D:
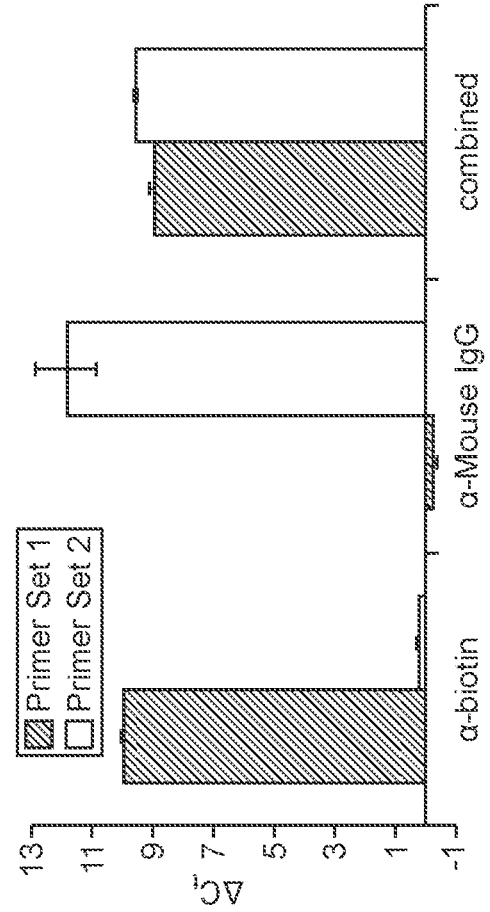
Figure 9F:
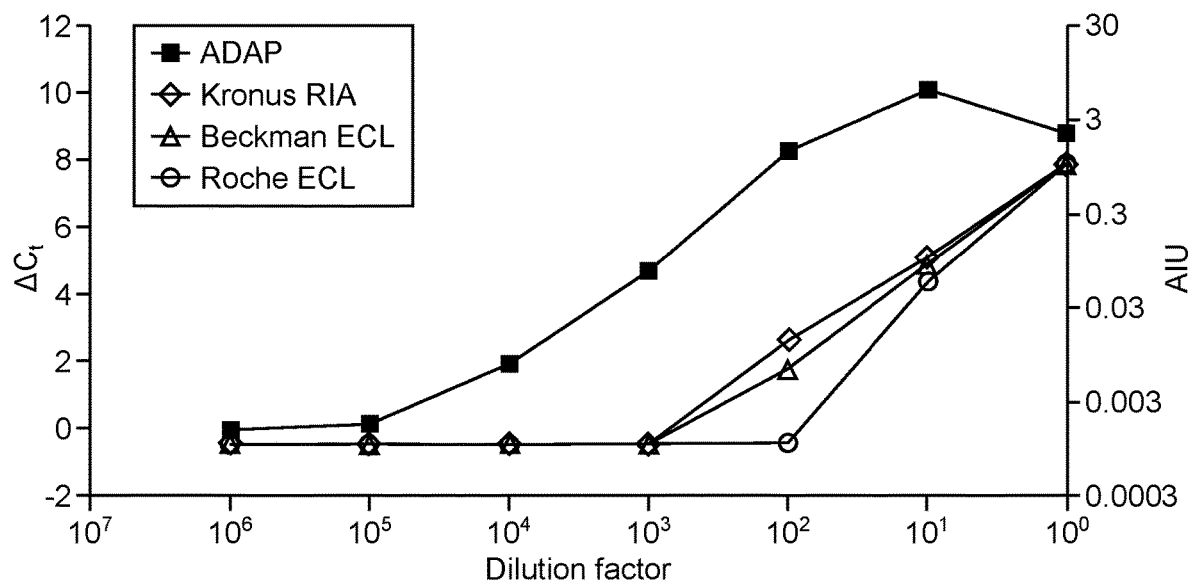
Figure 9G:
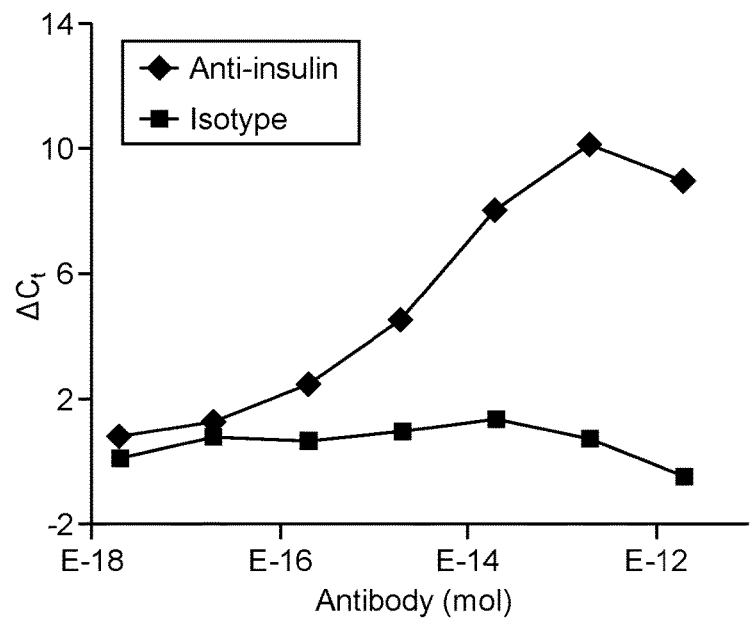
Figure 9H:
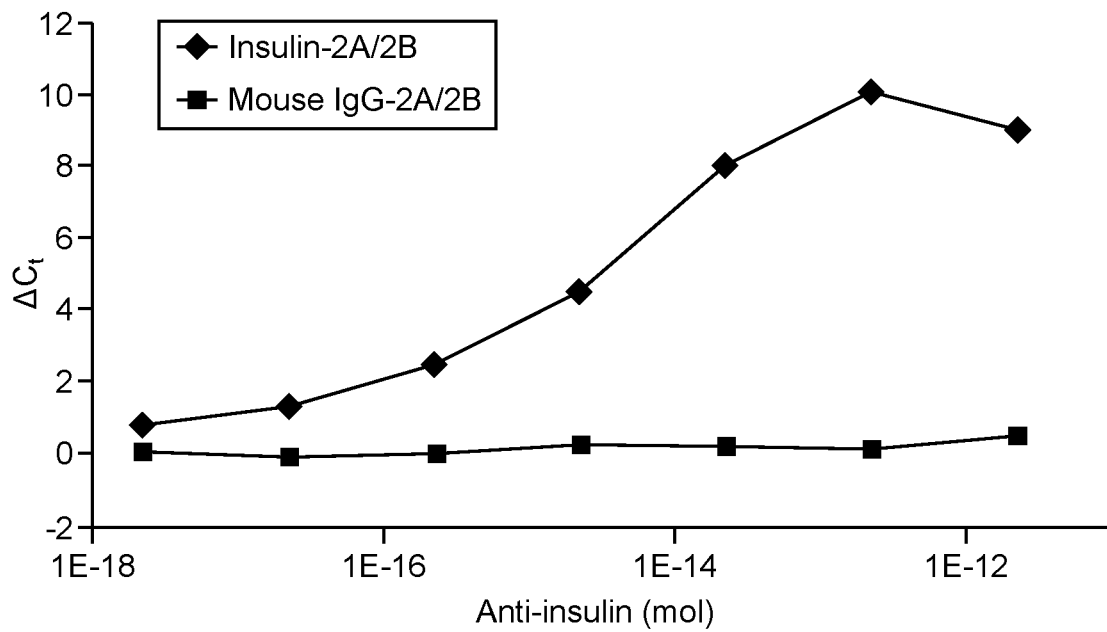
Figure 9I:
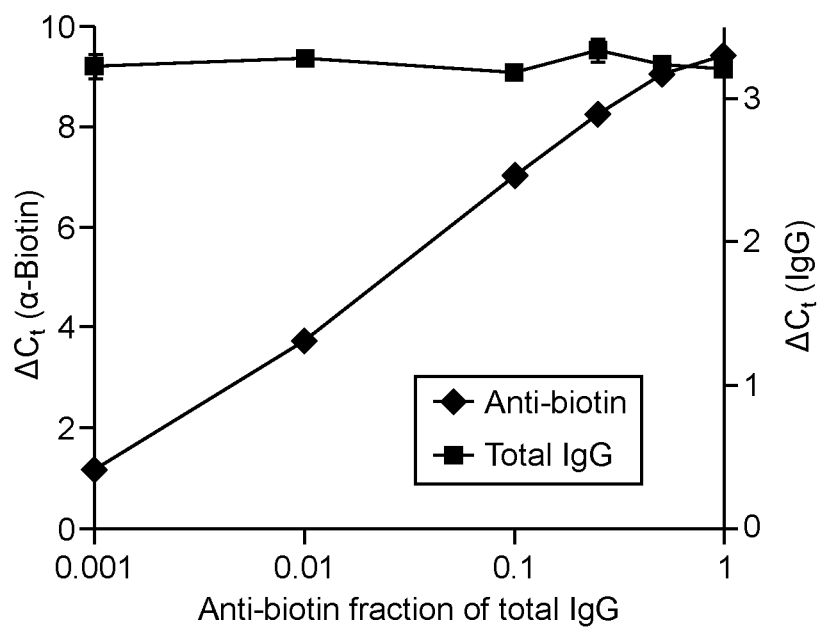
Figure 9J:
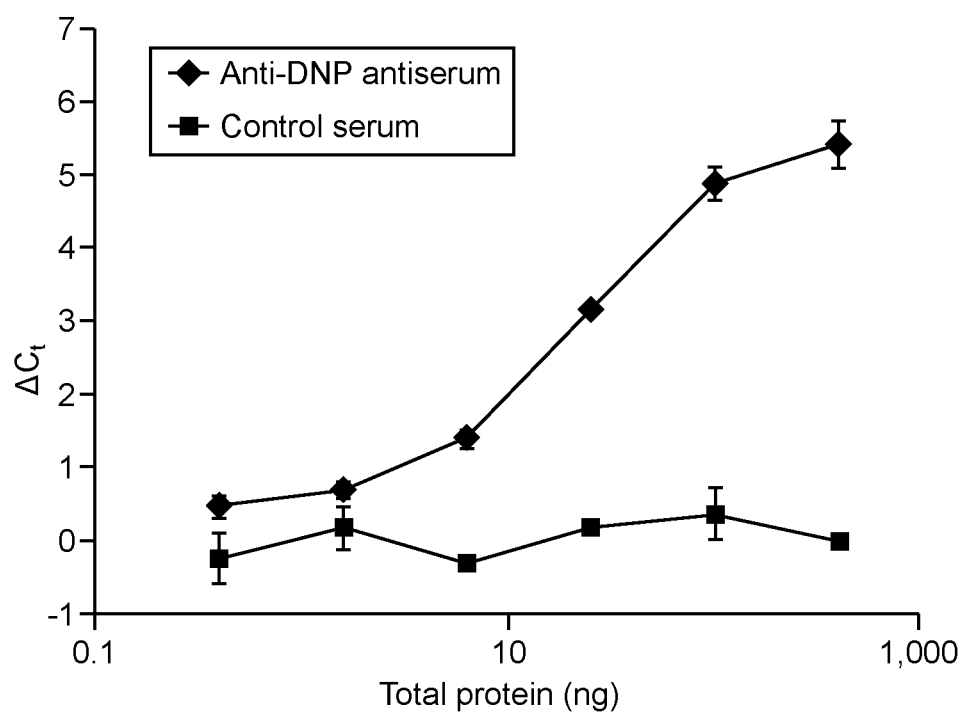

FIG. 9A-9J. SIMPAL or ADAP enables the highly sensitive and multiplexable detection of antibodies in complex matrices. α-Insulin antibodies were diluted into either PBS, fetal bovine serum, or human saliva and then subjected to SIMPAL analysis with insulin-DNA conjugates (FIG. 9A). Both biotin- and mouse IgG-DNA conjugates were incubated with either α-biotin (FIG. 9D, left) or α-mouse IgG antibodies (FIG. 9D, middle), or both (FIG. 9D, right) and then subjected to SIMPAL qPCR analysis. A head-to-head comparison of the agglutination assay and an ELISA assay was performed, demonstrating the superior sensitivity of SIMPAL (FIG. 9B). Equal quantities of α-Insulin antibodies were diluted into PBS and then analyzed by either SIMPAL or direct ELISA. Human samples from patients tested positive for α-thyroglobulin antibodies were analyzed and compared against normal human plasma and purified antibodies (FIG. 9C). SIMPAL was performed using Primer Set 1, specific for oligos bound to α-biotin, and Primer Set 2, specific for α-Mouse IgG, in samples containing only α-biotin, only α-Mouse IgG, and both α-biotin and α-Mouse IgG (FIG. 9D). The detection of diagnostic antibody α-thyroglobulin with thyroglobulin-DNA conjugates was performed on pooled healthy human plasma (Normal) in comparison to plasma from patients that tested positive for thyroglobulin autoantibodies (α-Thyroglobulin Positive) at three separate dilutions (1:10, 1:1000, 1:100,000) (FIG. 9E). Identical samples of anti-thyroglobulin-positive human plasma were analyzed by ADAP, an FDA-approved radioimmunoassay (Kronus RIA) and two electrochemiluminescent assays (Beckman and Roche ECL) (FIG. 9F). The specificity of ADAP was investigated by analysis of serially diluted isotype IgG in serum and no detectable signal was observed (FIG. 9G). Error bars represent standard deviation from triplicate samples, but for many data points are too small to be visualized.

Anti-insulin antibodies were incubated with insulin- or mouse IgG-DNA conjugates in bovine serum and then analyzed by ADAP (FIG. 9H). As expected, the anti-insulin antibodies agglutinate the insulin-DNA conjugates and generate signal but do not agglutinate the mouse IgG-DNA conjugates, as they have no affinity for this unrelated protein, and therefore generate no signal. This result demonstrates that ADAP is specific for the cognate antigen-antibody pair. Multiplexed detection of anti-antigen antibody and total antibody levels by ADAP and proximity ligation assay (PLA), respectively (FIG. 9I). Biotin-DNA conjugates and anti-IgG-DNA conjugates were incubated with samples containing constant total IgG but varied fractions of anti-biotin antibodies. These samples were analyzed by ADAP and PLA. Error bars represent the standard deviation from triplicate samples, but for many data points are too small to be visualized.

Detection and analysis by ADAP of anti-dinitrophenol (DNP) from rabbit antiserum was performed by serially diluting antiserum into PBS (FIG. 9J). A dilution series of antigen-naïve serum was analyzed as a negative control.

TABLE 2

Oligonucleotide Sequences

| Name | 5' mod | 3' mod | Sequence |
|---|---|---|---|
| Set 1 A | Thiol | None | CAGGTAGTAGTACGTCTGTTTCACGATGAGACTGGATGAA (SEQ ID NO: 2) |
| Set 1 B | Phosphate | Thiol | TCACGGTAGCATAAGGTGCAAGATAATACTCTCGCAGCAC (SEQ ID NO: 3) |
| Set 1 bridge* | None | None | CUACCGUGAUUCAUCCAG (SEQ ID NO: 4) |
| Set 1 F | None | None | GGCCTCCTCCAATTAAAGAA (SEQ ID NO: 5) |
| Set 1 R | None | None | GTGAACCGTTATTTGGGTAC (SEQ ID NO: 6) |
| Set 2 A | Thiol | None | GGCCTCCTCCAATTAAAGAATCACGATGAGACTGGATGAA (SEQ ID NO: 7) |
| Set 2 B | Phosphate | Thiol | TCACGGTAGCATAAGGTGCAGTACCCAAATAACGGTTCAC (SEQ ID NO: 8) |
| Set 2 bridge* | None | None | CUACCGUGAUUCAUCCAG (SEQ ID NO: 4) |
| Set 2 F | None | None | GGCCTCCTCCAATTAAAGAA (SEQ ID NO: 5) |
| Set 2 R | None | None | GTGAACCGTTATTTGGGTAC (SEQ ID NO: 6) |
| Set 4 A | Thiol | None | TCGTGGAACTATCTAGCGGTGTACGTGAGTGGGCATGTAGCAAGAGG (SEQ ID NO: 9) |
| Set 4 B | Phosphate | Thiol | GTCATCATTCGAATCGTACTGCAATCGGGTATTAGGCTAGTGACTACTGGTT (SEQ ID NO: 10) |
| Set 4 bridge* | None | None | GAAUGAUGACCCUCUUGCUA (SEQ ID NO: 11) |

TABLE 2-continued

Oligonucleotide Sequences

| Name | 5' mod | 3' mod | Sequence |
|---|---|---|---|
| Set 4 F | None | None | CGTGGAACTATCTAGCGGTGTA (SEQ ID NO: 12) |
| Set 4 R | None | None | ACCCGATTGCAGTACGATTC (SEQ ID NO: 13) |

*U = deoxyribouracil

The above indicates that ADAP enjoys many advantages over conventional antibody detection methods, including ELISA and RIA. ADAP uses very low sample volume with ultra-low reagent consumption in a solution-phase, wash free, non-radiological, reaction. A comparison of ADAP parameters to those of ELISA and RIA are provided below in Table 3. ADAP and ELISA values were calculated from in-house experiments. RIA values were determined from previously reported results, see e.g., Falorni et al. (1995) J. Immunol. Meth. 186:89-99, the disclosure of which is incorporated herein by reference in its entirety.

TABLE 3

ADAP, ELISA and RIA Assay Parameters:

|  | ADAP | ELISA | RIA |
|---|---|---|---|
| Detection Limit (attomole) | 4.3 | 3722 | 32 |
| Sample volume (μL) | 2 | 100 | 25 |
| # of assays per 100 μg of antigen | 1.7 × 10⁶ | 10-50 | N/A |
| Assay duration (hrs) | <3 | <4 | 3-24 |
| Multiplexability | ~2-50 | <9 | None |
| Solid support required | No | Yes | No |
| Washing/centrifugation steps | No | Yes | Yes |
| Radioisotope required | No | No | Yes |
| Detection device | thermocycler | Plate reader | γ counter |

Figure 11C:
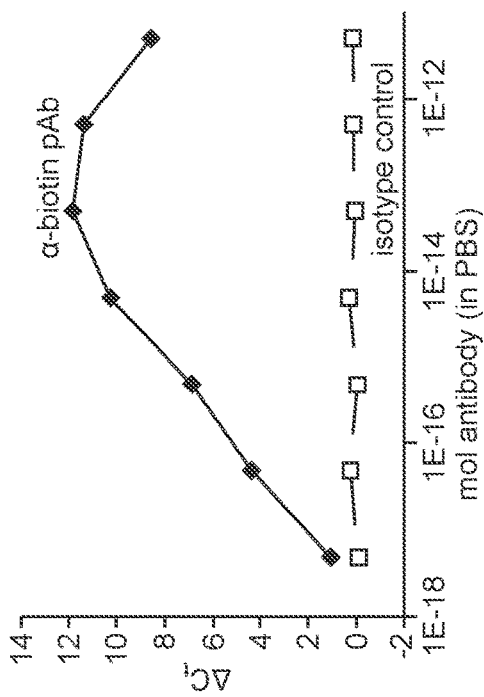
FIG. 11A-11C depict Biotin-DNA conjugate agglutination by anti-biotin antibodies, and quantitative detection thereof, in various sample types and with various detection polynucleotides.
Figure 11A:
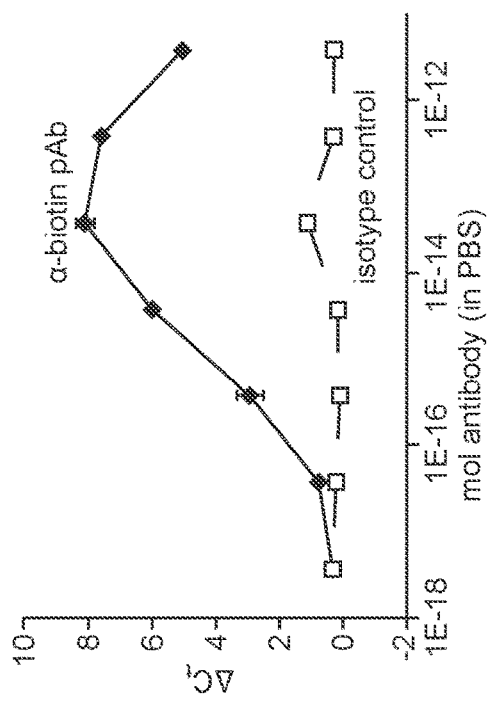
Figure 11B:
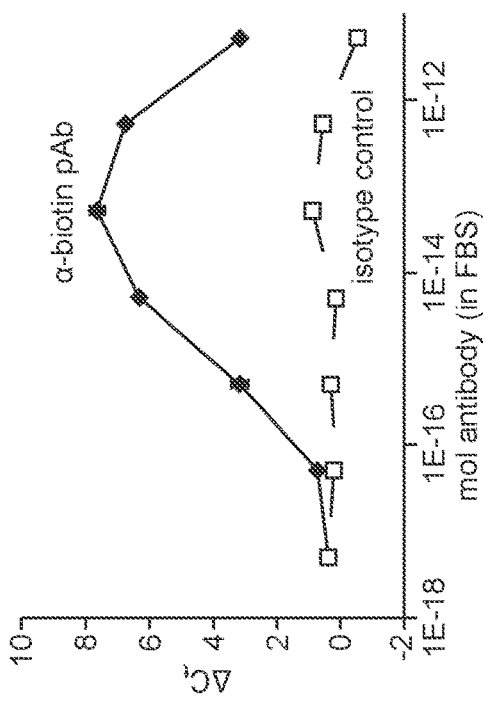

Example 2: PCR-Based Agglutination-Ligation Assays for Biotin, DNP, IgG and GFP Antibodies Antigen-DNA conjugates were incubated at 1 femtomole of each conjugate in 2 μL of buffer into a dilution solution containing DNA ligase and a bridging oligonucleotide that hybridized with the central 20 bp region of both strands. This ligation mixture was then diluted and pre-amplified by 13 rounds of PCR. The resulting PCR products were then analyzed by qPCR using Sybr Green detection. A dose-dependent response to the concentration of agglutinating antibody was observed, with a detection limit of about 37.5 attomoles of antibody (FIG. 11A-11C). Similar detection limits for antibodies were diluted in bovine serum was observed. Incubation with the corresponding isotype control yielded no signal in either case. To establish the generalizability of the sequences used, an orthogonal set of DNA-antigen conjugates was synthesized and the experiment was repeated. This sequence performed slightly better, with a detection limit of 3.75 attomoles of antibody.

Figure 12C:
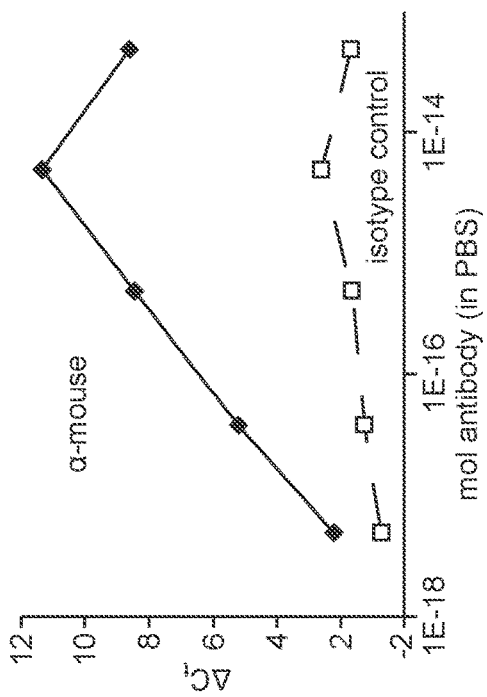
FIG. 12A-12C depict Mouse IgG-DNA conjugate agglutination by anti-mouse IgG antibodies, and quantitative detection thereof, in various sample types and with various detection polynucleotides.
Figure 12A:
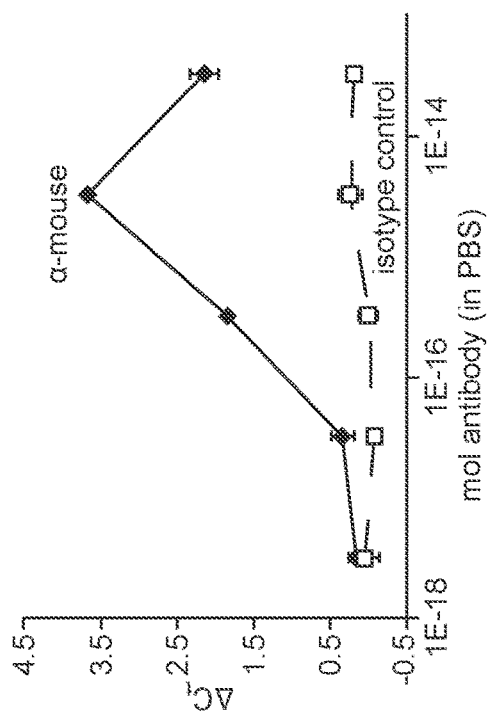
Figure 12B:
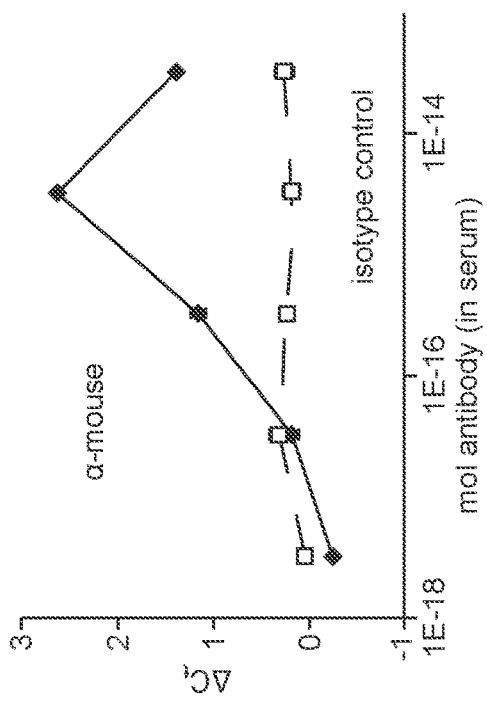
Figure 13:
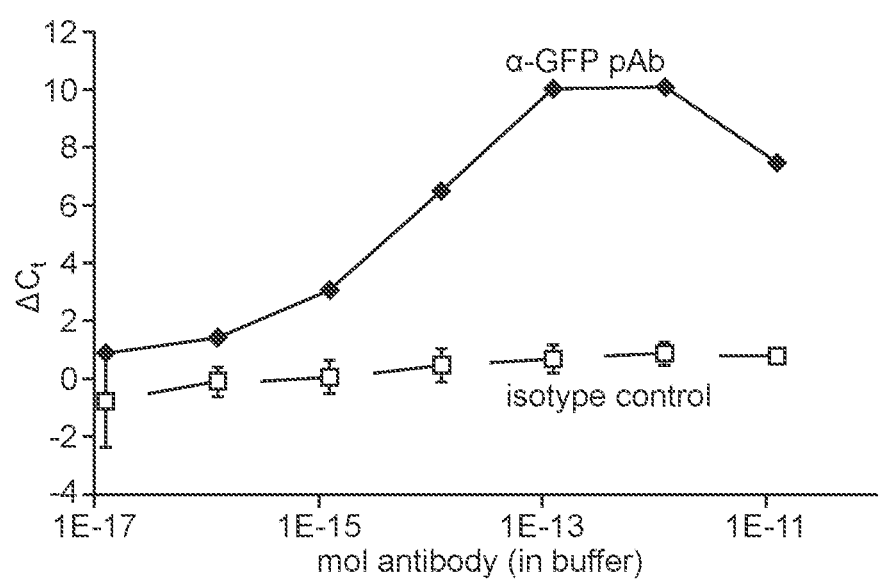
FIG. 13 depicts GFP-DNA conjugate agglutination by anti-GFP antibodies and qPCR-based quantitation thereof.

The detection strategy was tested with protein based antigens. Mouse IgG-DNA conjugate was incubated with a dilution series of a-mouse pAb. After ligation and pre-amplification, the samples were analyzed by qPCR. A dose-dependent signal in response to the concentration of antibody was observed (FIG. 12A-12C). Similarly, pre-incubation of the antibody and antigen-DNA conjugates in serum had no effect on the detection efficiency. Isotype control yielded no signal above background. These experiments were repeated with GFP-DNA conjugates to similar results (FIG. 13).

Figure 14C:
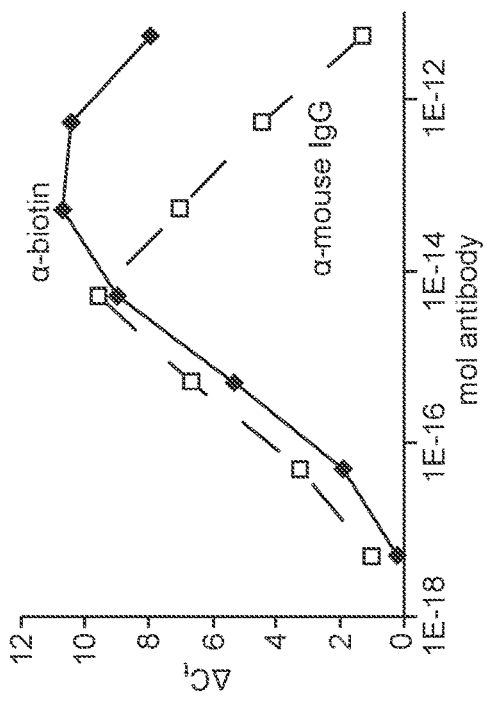
FIG. 14A-14C depict multiplexed quantitative polymerase chain reaction (qPCR)-based detection of Mouse IgG-DNA and biotin-DNA agglutination mediated by corresponding antibodies.
Figure 14A:
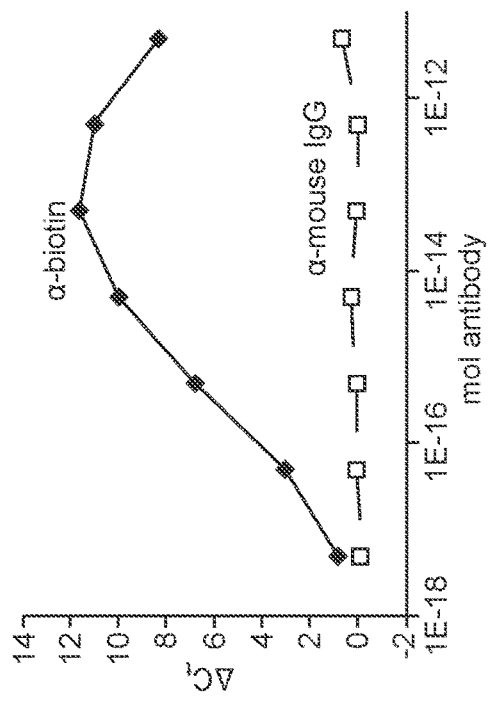
Figure 14B:
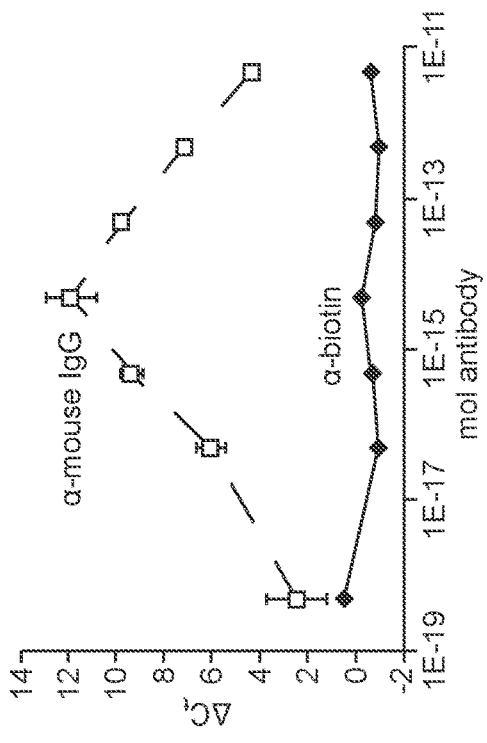

To perform the assay in multiplex, a set of orthogonal antigen-DNA conjugates with biotin (Sequence Set 1) and mouse-IgG (Sequence Set 2) was generated. These amplicons were designed such that Set 1 primers did not amplify the Set 2 amplicon and vice versa. The two antigen-DNA conjugates were pooled and then incubated with antibodies that bind either only mouse IgG (FIG. 14B), only biotin (FIG. 14A), or both (FIG. 14C) and then analyzed for agglutination. The sample incubated with the anti-mouse IgG antibodies showed signal only with Set 1 primers, while the sample incubated with the anti-GPP antibodies showed signal only in the Set 2 primers and the mixed sample generated signal with both sets of primers (FIG. 14A-14C).

FIG. 11A-11C. Biotin-DNA conjugates agglutination by α-biotin antibodies is detected by qPCR. Biotin-DNA conjugates were incubated with various concentrations of α-biotin or isotype control antibodies diluted in buffer (FIG. 11A, FIG. 11C) or serum (FIG. 11B). Samples were then treated with DNA ligase and then analyzed by qPCR. An orthogonal DNA sequence was used in FIG. 11C to show replicability. Y-axis values are shown as $\Delta C_T$ in comparison to a blank. Error bars represent the standard deviation from triplicate but are too small to be visualized for many data points.

FIG. 12A-12C. Mouse IgG-DNA conjugate agglutination is sensitively detected by qPCR. Mouse IgG-DNA conjugates were incubated with various concentrations of a-mouse IgG or isotype control antibodies diluted in buffer (FIG. 12A, FIG. 12C) or serum (FIG. 12B). Samples were then treated with DNA ligase and then analyzed by qPCR. An orthogonal DNA sequence was used in FIG. 12C to show replicability. Y-axis values are shown as $\Delta C_T$ in comparison to a blank. Error bars represent the standard deviation from triplicate but are too small to be visualized for many data points.

Figure 17:
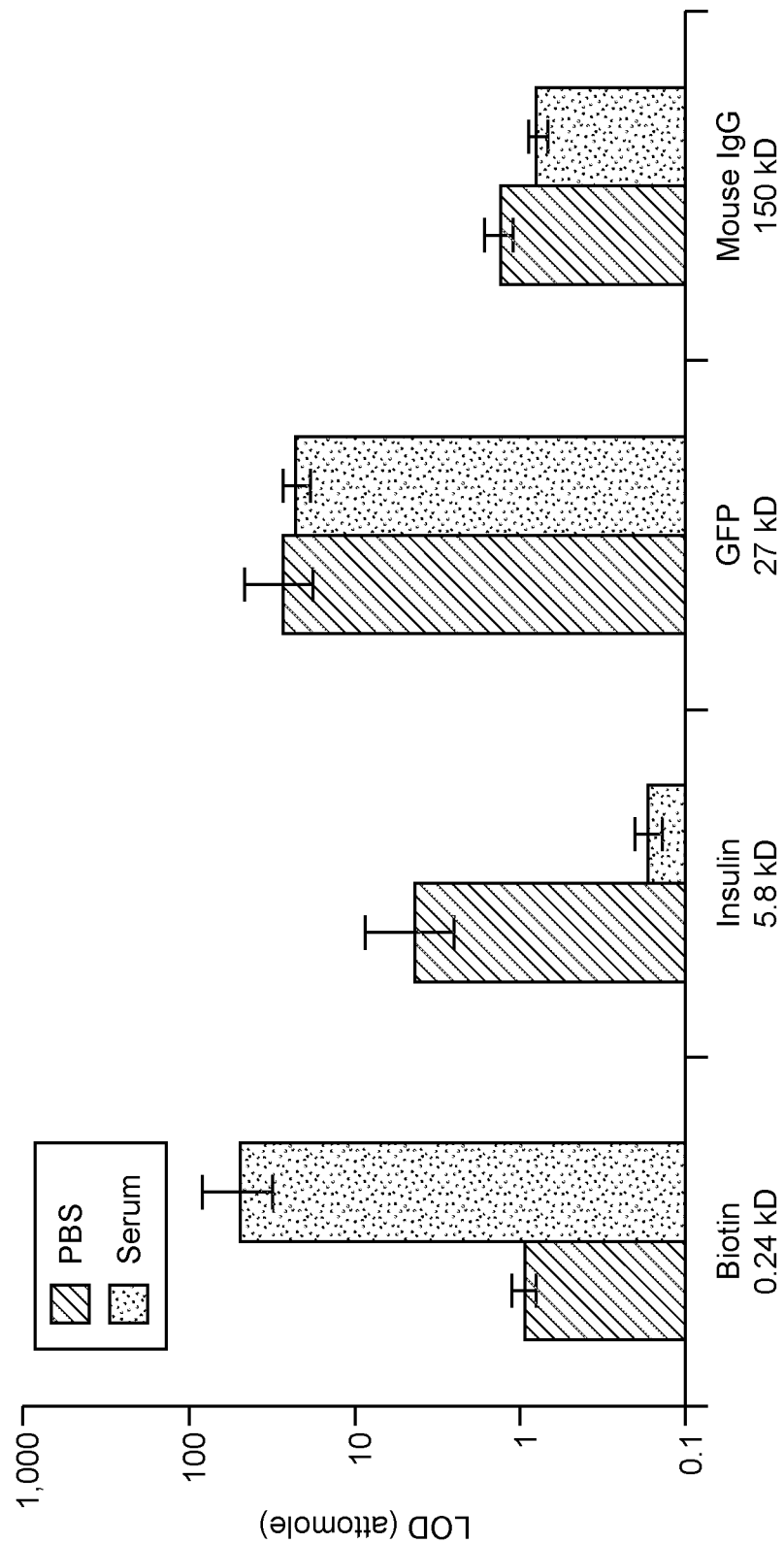
FIG. 17 provides empirically determined limits of detection (LOD) for various antibodies in PBS or serum using an embodiment of the methods described herein.

The above, in Examples 1 and 2, demonstrate that ADAP scales over a broad range of antigen molecular weights, as assays for antigen-antibody pairs for biotin (~0.24 kDa), GFP (26 kDa), and mouse IgG (150 kDa) are all demonstrated (FIG. 17). For all three pairs, ADAP consistently detected low attomoles of antibody (see e.g., Table 1, FIG. 11A-11C, FIG. 12A-12C and FIG. 13)

FIG. 13. GFP-DNA conjugate agglutination is detected by PCR-based agglutination-ligation assay. GFP-DNA conjugates were incubated with various concentrations of anti-GFP or isotype control antibodies diluted in buffer. Samples were then treated with DNA ligase and analyzed by qPCR. Y-axis values are shown as $\Delta C_T$ in comparison to a blank. All experiments were performed in triplicate. Similar results were obtained when anti-GFP or isotype control antibodies were diluted in serum. Error bars represent the standard deviation from triplicate but are too small to be visualized for many data points FIG. 14A-B. Multiplexed detection of antigen agglutination. Mouse IgG-DNA and biotin-DNA conjugates with orthogonal sequences were pooled and incubated with antibodies that bind Mouse IgG only (FIG. 14B), biotin only (FIG. 14A) or both Mouse IgG and biotin (FIG. 14C). Y-axis values are shown as $\Delta C_T$ in comparison to a blank. These results demonstrate the orthogonality of multiplexed antibody detection using ADAP.

FIG. 17. ADAP detects zeptomoles to attomoles of antibodies that bind antigens across a wide molecular weight distribution. The limits of ADAP detection for antibiotin, anti-insulin, anti-GFP, and antimouse IgG antibodies (antigen molecular weights of 0.24, 5.8, 27, and 150 kDa respectively) was determined by analyzing antibodies added into PBS or bovine serum. Error bars represent the standard deviation from triplicate samples.

Example 3: PCR-Based Amplification/Detection of Multivalent Antibodies

Figure 15:
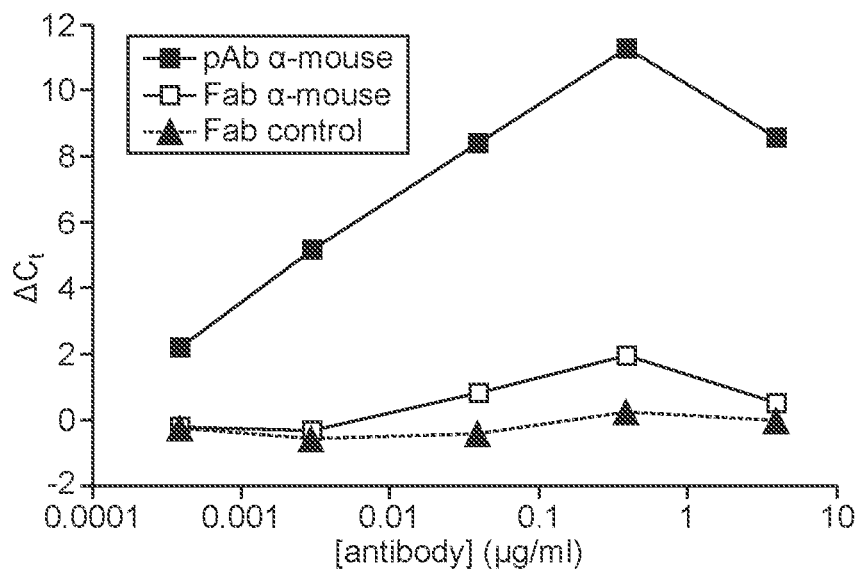
FIG. 15 provides a comparison of detection and quantification of various concentrations of multivalent polyclonal anti-mouse antibody and monovalent anti-mouse digested Fab fragments by qPCR.

Amplification and detection of an antigen binding agent in a sample by agglutination-based assays, as described herein, is dependent on multivalency of the antigen binding agent. Multivalent polyclonal anti-mouse antibody (pAb α-mouse) was detected and quantified in a sample in a concentration dependent manner by qPCR using polynucleotide-bound antigen in a PCR-based agglutination assay as described herein (FIG. 15). Robust signal was generated for polyclonal antibody (pAb α-mouse), however, digested monovalent antibody fragments (Fab α-mouse) and negative control antibody fragments (Fab control) did not generate significant signal at any tested concentration by qPCR using polynucleotide-bound antigen in the PCR-based agglutination assay (FIG. 15).

Figure 16:
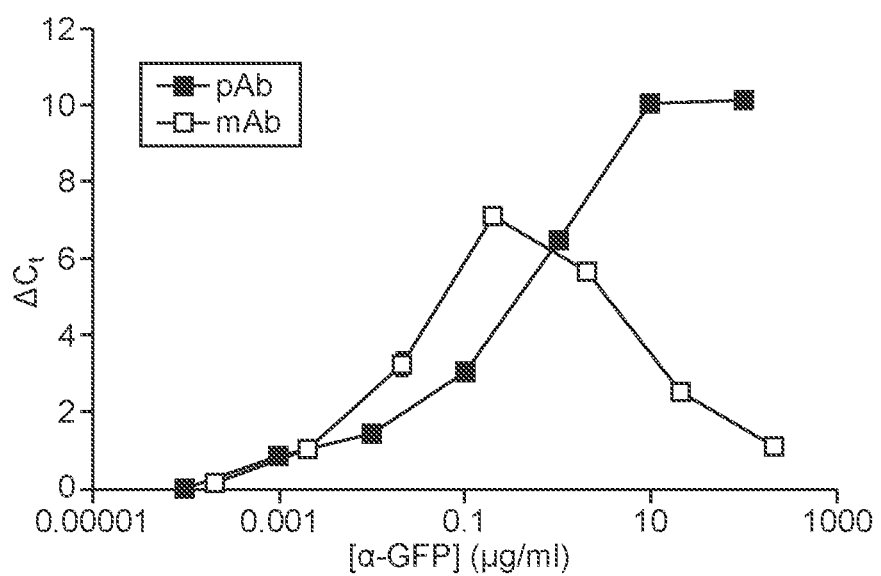
FIG. 16 provides a comparison of detection and quantification of various concentrations of polyclonal antibody and monoclonal antibody by qPCR.

In PCR-based amplification/detection assays where amplification is dependent on multivalent antibody complex formation with polynucleotide bound antigen, monoclonal antibody and polyclonal antibody were detected with similar detection limits (FIG. 16). In such an assay, the dynamic range of detection of a-GFP monoclonal antibody (mAb) and a-GFP polyclonal antibody (pAb) was unequal (about 6 or 4 orders of magnitude for polyclonal or monoclonal antibody, respectively), showing detection and quantification of pAb over a larger dynamic range than that for mAb. The inflection point of the quantification curve of mAb (0.1 µg/ml) reflects the point where the concentration of added mAb was approximately equivalent to the concentration of added antigen-DNA conjugates in the sample which, without being bound by theory, may indicate competition for antigen epitope binding sites between individual molecules of mAb. These findings shed light on the mechanistic behavior or agglutination in the described assay while also demonstrating that, although differing dynamic ranges may be expected, ADAP is well-suited for the detection of both poly- and monoclonal antibodies.

FIG. 15. Comparison of detection and quantification of various concentrations of multivalent polyclonal anti-mouse antibody (pAb α-mouse) and monovalent anti-mouse digested Fab fragments (Fab α-mouse) by qPCR amplification/detection with polynucleotide-bound antigen.

FIG. 16. Comparison of detection and quantification of various concentrations of polyclonal anti-GFP antibody (pAb) and monoclonal anti-GFP antibody (mAb) by qPCR amplification/detection with polynucleotide-bound antigen.

In both FIG. 15 and FIG. 16 errors bars represent the standard deviation from triplicate samples, but for many data points the error bars are too small to be visualized.

Example 4: Circumventing Interference from Anti-DNA Autoantibodies

Interference from endogenous anti-DNA autoantibodies in ADAP was investigated. Such antibodies could potentially agglutinate antigen-DNA conjugates in an antigen-agnostic manner and result in false positives. Patients suffering from autoimmune disorders such as systemic lupus erythematosus (SLE) often produce anti-DNA antibodies in high titer. They are also generally present in small quantities in about 10% of healthy adults.

Patient plasma was obtained that was independently verified to harbor anti-DNA antibodies. Normal plasma was also obtained, as a negative control, which harbored much lower levels of anti-DNA antibodies. GFP-DNA conjugates were used as a control antigen to observe the extent of interference from anti-DNA autoantibodies, since there should be no naturally occurring anti-GFP antibodies in human plasma.

As expected, strong signal from anti-DNA-positive patient plasma was observed as was weak yet robust signal from normal plasma (FIG. 18A), demonstrating that these antibodies can interfere with ADAP analysis. Interestingly, after adding in anti-GFP antibodies, identical dose-response curves were observed for both anti-DNA-positive patient plasma and normal plasma (FIG. 19). This observation is consistent with the notion that high affinity anti-GFP antibodies dominate the agglutination event and ADAP signal, regardless of the presence of anti-DNA antibodies.

In an abundance of caution, a general solution to circumvent potential interference from anti-DNA autoantibodies was sought. To this end, free DNA was titrated in as a competitor to "protect" the antigen-DNA conjugates from counterfeit aggregation (FIG. 18B). At 100 µM of the competitor DNA, spurious signal from anti-DNA antibodies was no longer observed (FIG. 18B-18C). To validate that competitor DNA does not otherwise complicate ADAP performance, both anti-GFP antibodies and competitor DNA were added to anti-DNA positive plasma and normal plasma (FIG. 18D). ADAP analysis of these samples showed the expected dose response with no interference from anti-DNA antibodies. The limit of detection of anti-GFP antibodies in human plasma was similar to that in buffer (48 and 27 attomoles, respectively; the former indicating a detection limit in human plasma of 3.6±0.5 ng/ml). Together, these results demonstrate that the addition of competitor DNA allows us to circumvent interference in human plasma samples.

Figure 18A:
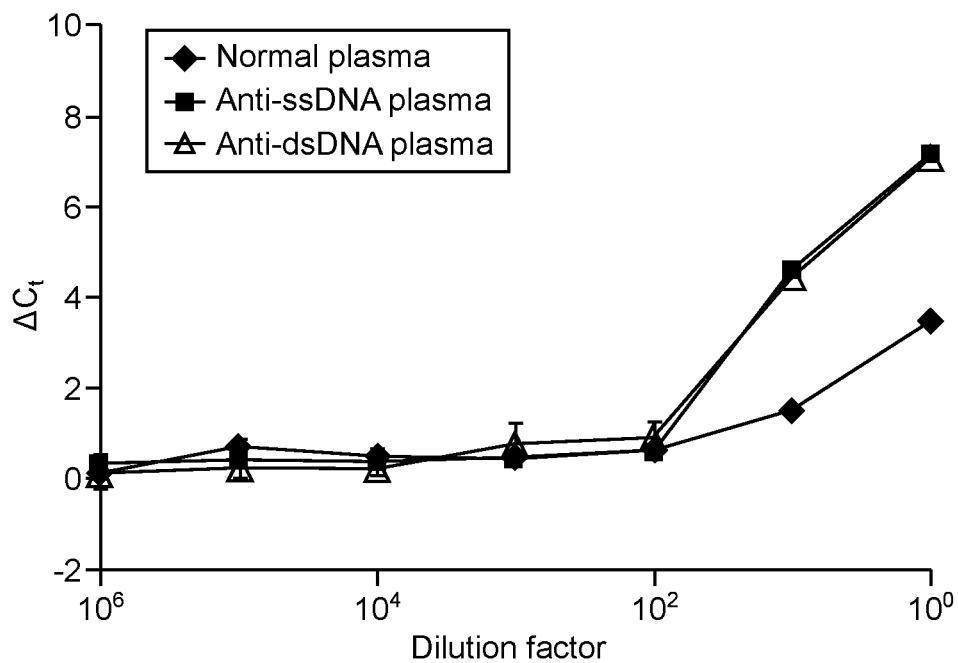
FIG. 18A-18D demonstrate that interference of target antibody detection by anti-nucleic acid antibodies in the sample can be circumvented in the instantly disclosed method.
Figure 18B:
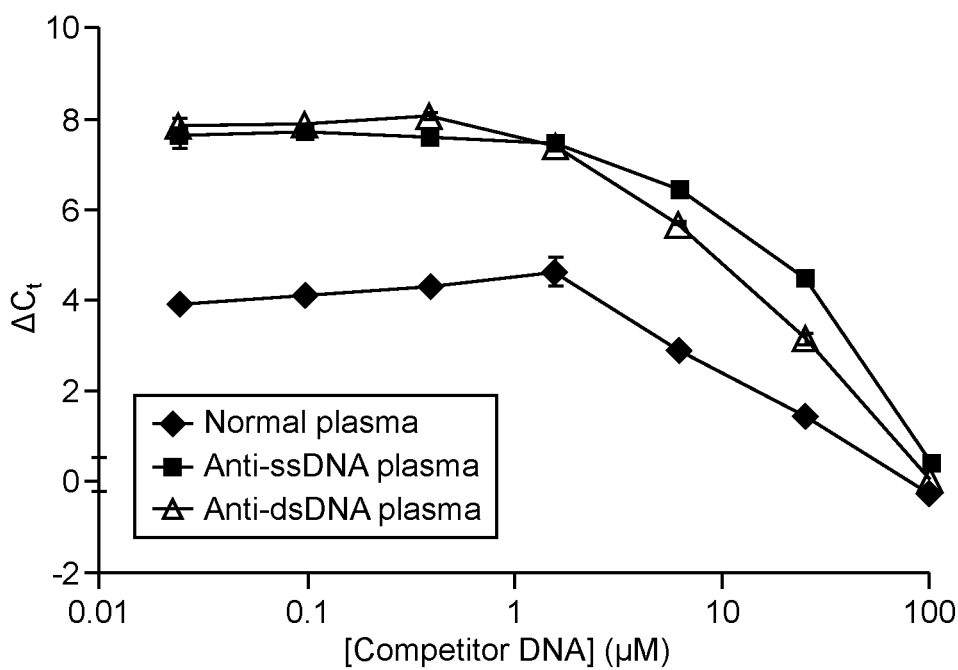
Figure 18C:
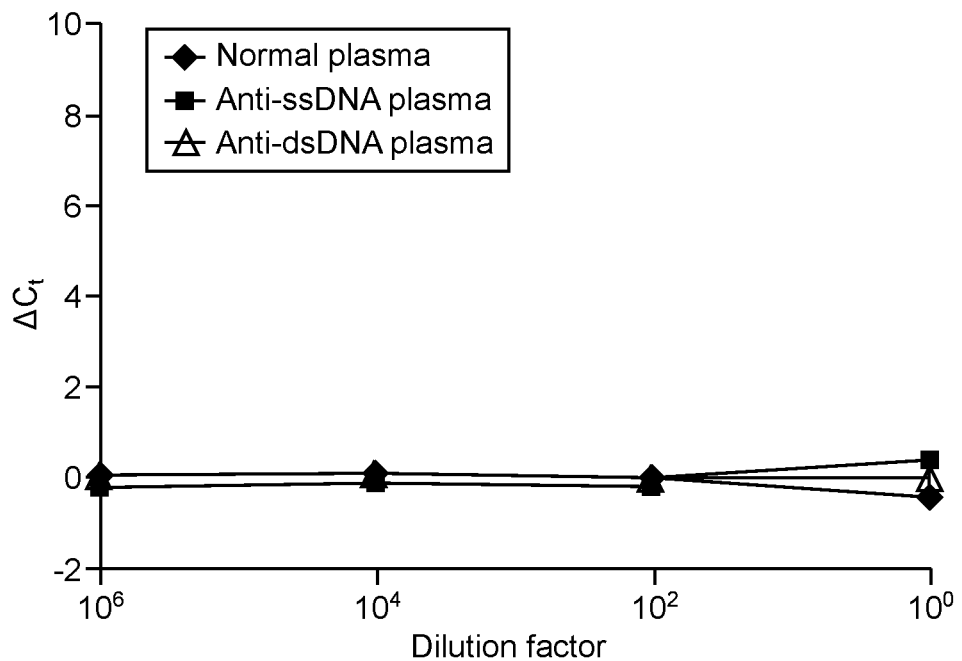
Figure 18D:
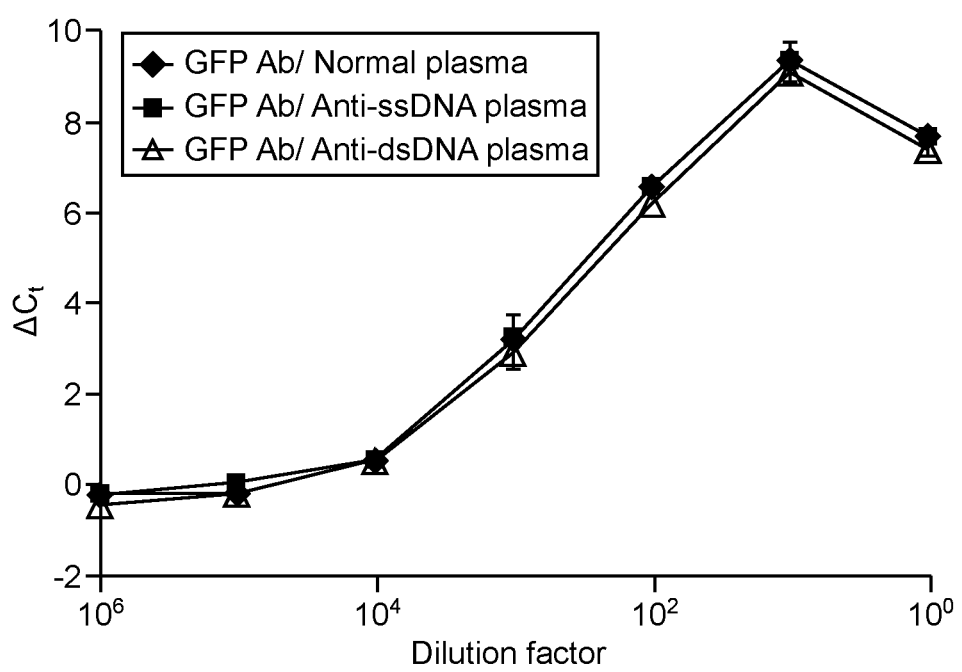
Figure 19:
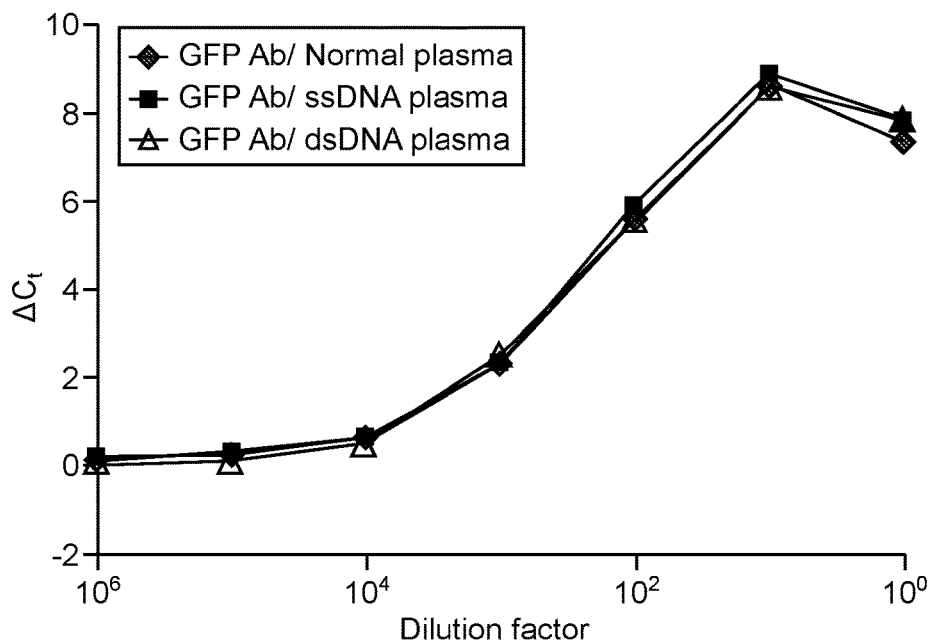
FIG. 19 depict the detection of anti-GFP antibodies in anti-DNA and normal plasma without competition DNA.

FIG. 18A-18D. Circumventing interference from anti-DNA autoantibodies by competition with free DNA. Investigation of interference from anti-DNA autoantibodies. GFP-DNA conjugates were used to analyze anti-DNA-positive patient plasma and healthy normal plasma (FIG. 18A). Patient samples were grouped into those containing anti-single-stranded DNA antibodies (ssDNA) and those with anti-dsDNA antibodies (dsDNA). Interference was observed at dilution factors of 1 and 10 for all sample types (FIG. 18B) Competitor DNA was titrated into undiluted patient and normal plasma. The addition of competitor DNA eliminated background signal from interfering antibodies. The experiment in FIG. 18A was repeated but with the addition of 100 µM competitor DNA which eliminated interference (FIG. 18C). Purified GFP antibodies were added to anti- DNA positive and normal plasma. Detection of GFP antibodies was performed in the presence of 100 µM competitor DNA in all samples to confirm that it did not disrupt ADAP performance (FIG. 18D).

FIG. 19. Detection of anti-GFP antibodies in anti-DNA and normal plasma without competition DNA. Anti-GFP antibodies were diluted into anti-DNA plasma or normal plasma and then analyzed by ADAP with GFP-DNA conjugates as the probes. Though interference is observed for anti-DNA and normal plasma at 1:1 and 1:10 dilutions as shown in FIG. 18A, no interference is observed in the presence of anti-GFP antibodies. This might be attributed to high affinity anti-GFP antibodies dominate the agglutination of GFP-DNA conjugates, which thus masks the interference from anti-DNA antibodies.

Example 5: Synthesis of Antigen-DNA Conjugates

Central to a sensitive ADAP assay is the creation of antigen-DNA conjugates. For protein antigens, these components were synthesized by lysine-to-thiol cross-linking using sulfosuccinimidyl 4-(N-maleimidomethyl)-cyclohexane-1-carboxylate (sulfo-SMCC) and thiolated oligonucleotides. Briefly, maleimides were installed on lysines of purified antigen by reaction with sulfo-SMCC in PBS (FIG. 20). Thiolated oligonucleotides were activated by dithiothreitol (DTT)-mediated reduction. Both antigen and oligonucleotides were desalted, pooled, and allowed to react overnight. Unreacted reagents were removed by extensive purification with size-exclusion spin columns. Antigen-DNA conjugation ratios were determined by UV-vis spectroscopy and by SDS-PAGE analysis. Typically, a 1:2 antigen-to-DNA conjugation ratio yielded the optimal signal in ADAP assays. Greater degrees of antigen-DNA conjugation were found to be capable of masking epitopes for antibody binding and thus leading to reduced assay sensitivity (FIG. 22).

Figure 23:
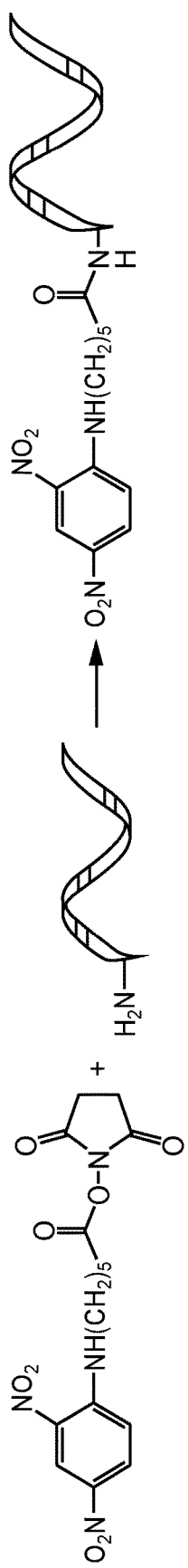
FIG. 23 provides a schematic representation of a reaction scheme for small molecule-DNA conjugate synthesis according to one embodiment of the instant disclosure.

For small molecule antigens, N-hydroxysuccinimidyl (NHS) ester-activated derivatives were incubated with amine-modified oligonucleotides in a one-step conjugation (FIG. 23). The resulting small molecule-DNA conjugates were characterized by high-resolution mass spectrometry. In contrast to protein-based antigens, small molecules contain far fewer antibody epitopes due to their size. It is thus critical to design conjugation sites that still preserve the accessibility of epitopes to antibodies. For the dinitrophenol (DNP)-DNA conjugate, the same conjugation site was used as was used to generate the immunogen for the antibody tested (a DNP-BSA conjugate in which DNP was linked to lysine side chains).

Figure 22:
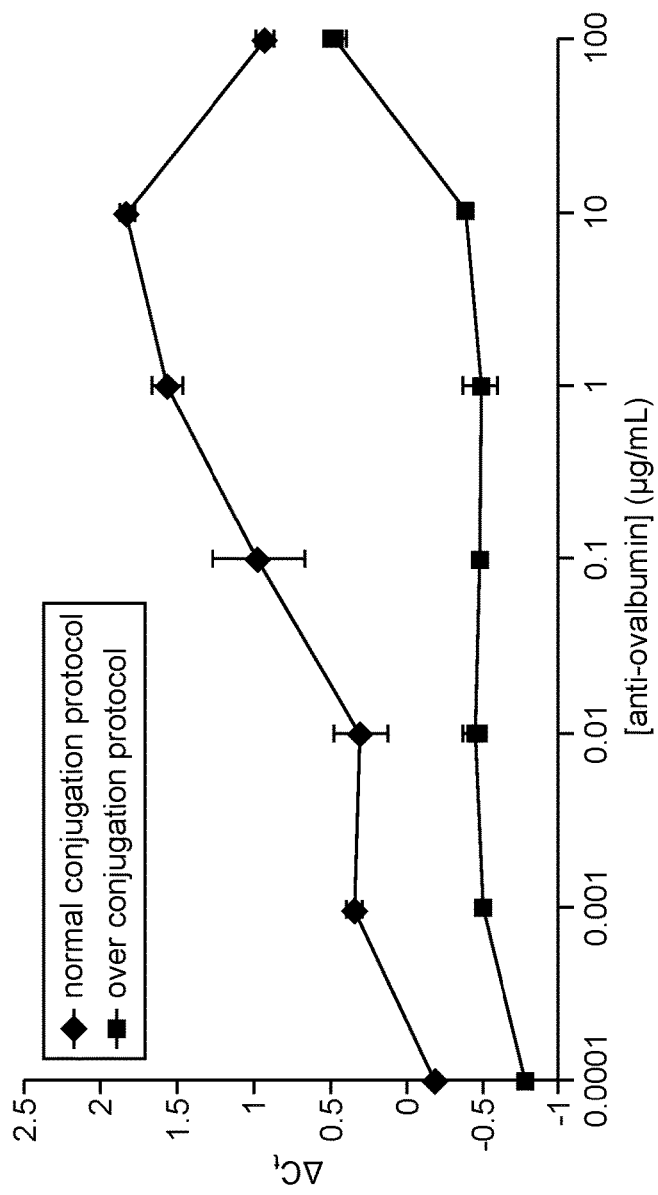
FIG. 22 demonstrates the effect of antigen:DNA conjugation ratio on assay performance.

FIG. 22. Effect of antigen:DNA conjugation ratio on ADAP performance. Ovalbumin (OVA)-antigens DNA conjugates were synthesized with either low or high antigen:DNA ratios (1:2 or 1:6 respectively). The ovalbumin conjugates are incubated with a dilution series of monoclonal anti-OVA antibodies in buffer and subjected to ADAP analysis. The overconjugated ovalbumin show significantly reduced assay performance while the normally conjugated ovalbumin shows concentration dependent signal as expected. Without being bound by theory, this may be the result of epitope masking when antigens are overconjugated with oligonucleotides.

FIG. 23. Reaction scheme for small molecule-DNA conjugate synthesis. DNP-DNA conjugates are synthesized by reacting succinimidyl ester-activated DNP with amine modified DNA in one step. The conjugation product is then characterized by mass spectrometry.

Example 6: Oral Sample HIV Screening by ADAP Assay

Increasing the number of individuals screened for HIV magnifies public health officers' ability to interrupt highly infectious sources of transmission. While serum/plasma-based HIV testing is the standard for definitive diagnosis, the number of samples that can be collected with this format is limited due to low compliance and safety issues. Oral fluid samples can be acquired from larger populations, as the collection process is non-invasive and much safer.

However, antibody levels in oral fluid are ~1000-fold lower than that found in serum or plasma. Current FDA-approved oral fluid tests lack the analytical sensitivity to detect the extremely low level of antibodies within the first 2-6 weeks of HIV infection, when patients are most likely to transmit the disease. A highly sensitive oral fluid assay that can detect the very low levels of antibodies would be able to identify patients at during this critical window while improving the number of patients that can be screened.

To address this issue, an HIV specific ADAP assay using antigen-DNA conjugated probes specific for HIV (p24, gp120, gp160, gp41, gp36, etc.) was designed. An assay for the detection of antibodies in oral fluid for HIV must take into account that the HIV in host immune response is a dynamic process. B-cells first release IgM, which later undergoes class-switching to produce IgG. To identify the disease at the earliest phase, the oral fluid assay must detect virus-specific antibodies in both isotypes. ADAP exploits the multivalency and agglutination power of IgM and IgG antibodies to drive the formation of amplifiable dsDNA upon antibody-antigen binding, and thus is well-suited to detect both antibody isotypes. Compounding the difficulty in HIV detection by this method are is the combination of inherently low levels of antibody in oral samples and low levels of virus-specific antibodies in recently infected individuals.

Figure 24A:
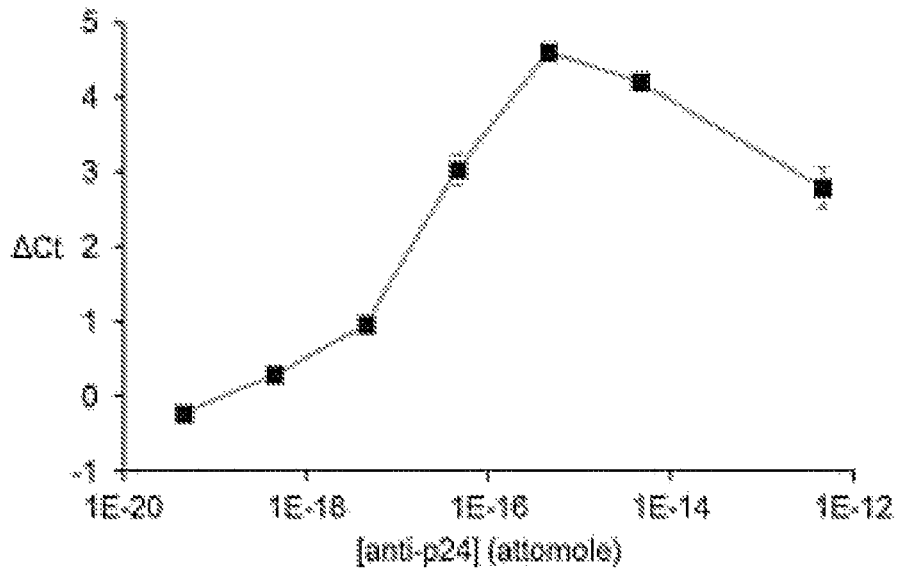
FIG. 24A-24B demonstrate the solo and multiplexed detection of HIV antibodies in an agglutination detection assay as described herein.

In initially testing, ADAP has been demonstrated to detect attomoles of anti-p24 antibodies (purified from HIV infected individuals) in 2 µl samples (FIG. 24A). Multiplexed detection of two different relevant antibodies (anti-gp120 and anti-p24) has also been demonstrated (FIG. 24B).

Figure 25:
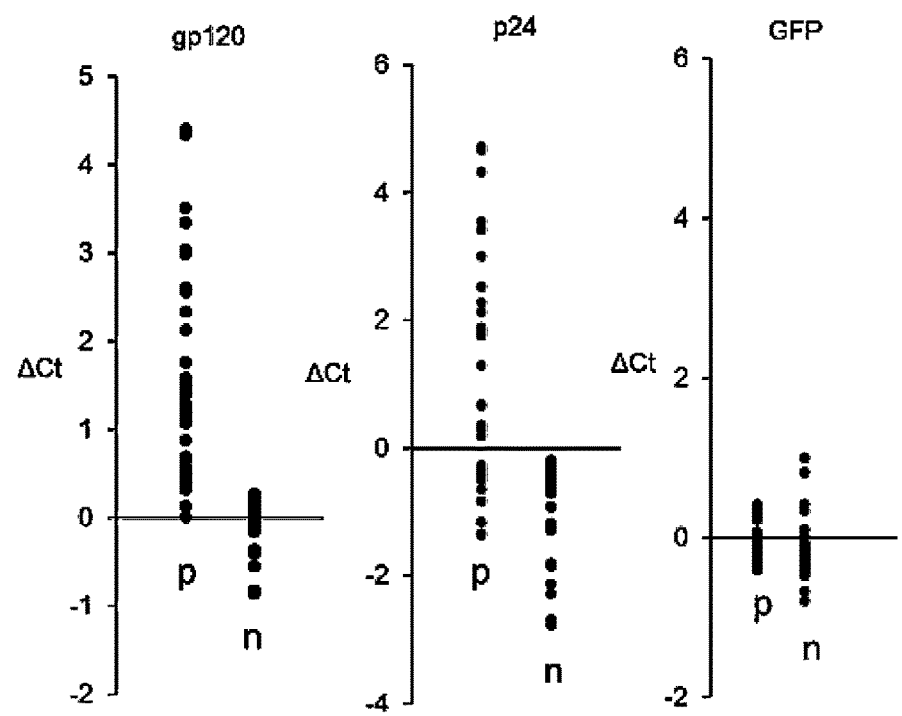
FIG. 25 demonstrates the segregation of HIV negative and positive subject populations as determined by an agglutination assay detecting HIV antibodies in human oral fluid samples.
Figure 26:
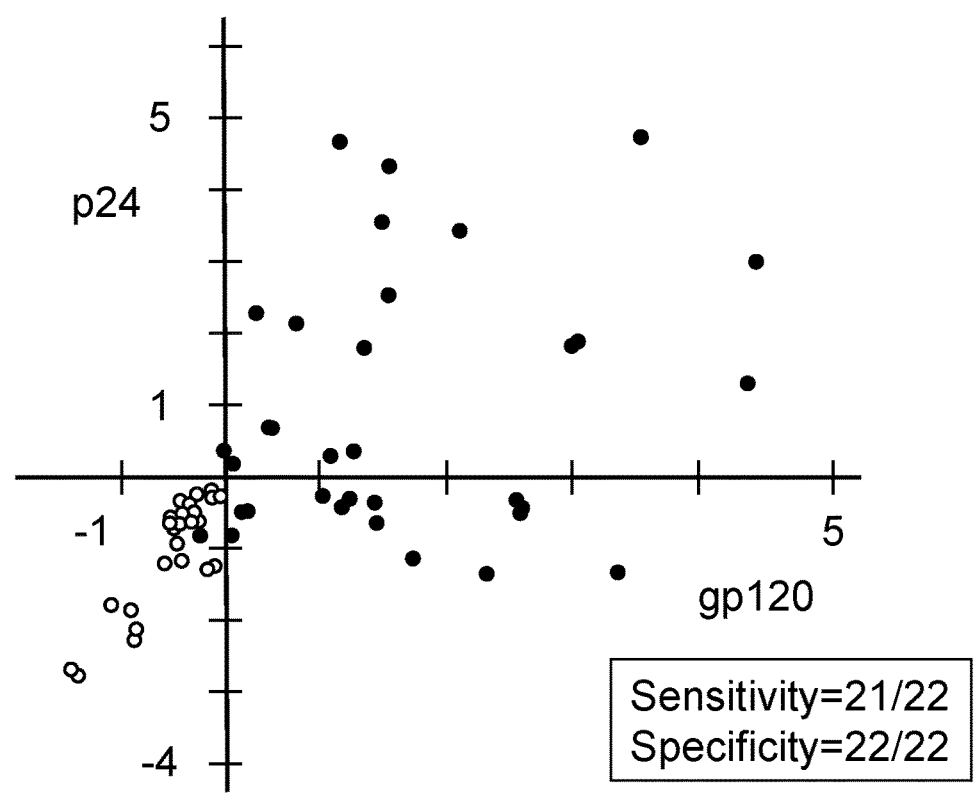
FIG. 26 depicts the clinical sensitivity and specificity of an HIV agglutination assay detecting two different HIV antibodies.

In a larger test, a cohort of 44 archived oral fluid samples were assayed by ADAP for the presence of anti-p24 and anti-gp120 antibodies (FIG. 25 and FIG. 26). Such testing found significantly higher levels of anti-p24 and anti-gp120 detection in the HIV positive patient population, demonstrating that the designed ADAP assay can differentiate HIV positive from normal oral sample populations. Considering both antigens together, this assay exhibited 95% sensitivity and 100% specificity. Furthermore, negative controls (GFP-DNA conjugates) showed no significant difference between the HIV positive and HIV negative patient populations.

These results demonstrate the functionality of the ADAP assay on real-world oral samples for the detection of HIV antibodies.

Figure 24B:
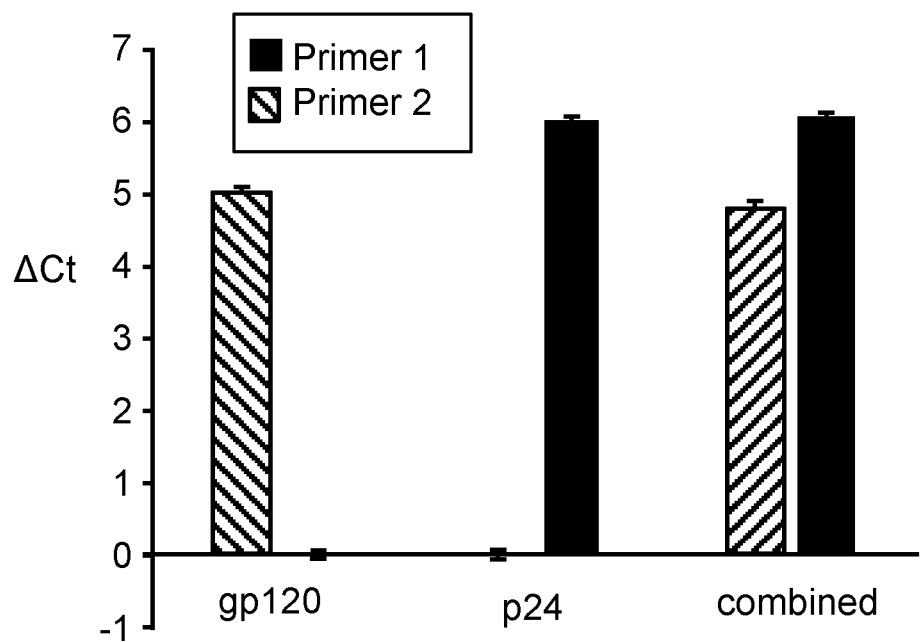

FIG. 24A-24B. Ultrasensitive detection of antibodies by ADAP technology. ADAP detects anti-p24 antibodies and demonstrates attomolar sensitivity in 2 µL samples (FIG. 24A). Specificity of ADAP was confirmed by assaying serum spiked with an isotype control antibody. No signal was detected from the negative control experiment. Multiplexed detection of anti-gp120 and anti-p24 antibodies (FIG. 24B). Gp120 and p24 antigens were coded with DNA sequences amplified either by Primer 1 or Primer 2, respectively. Their cognate antibodies are detected by an ADAP assay using Primer 1 for gp120 (dashed bars) or Primer 2 for p24 (solid bars). Most error bars for individual data points arising from technical replicates are too small to be seen (ΔCt: change in cycle threshold; a standard means of reporting qPCR signal relative to a control sample).

FIG. 25. ADAP-based antibody detection in human oral fluid samples. An ADAP assay detecting anti-gp120 (left) or p24 antibodies (center) segregate into HIV positive ("p") and negative ("n") populations. An ADAP assay detecting anti-GFP antibodies (right) shows little difference between the two populations.

FIG. 26. Clinical sensitivity and specificity based on gp120 and p24. Initial ADAP assays on 44 oral fluid samples achieved 95% sensitivity and 100% specificity using 1 µL of oral fluid. The inclusion of additional antigens (e.g., gp160 and gp41) will further enhance the assay's performance. (Closed Circles=positive oral fluid; Open Circles=negative oral fluid).

Example 7: Multiplexed Antibody Detection

A multiplexed antibody discovery kit was designed for the parallel detection of multiple different antibodies from small aliquots of a single sample. An initial 96-well-detection-plate-based assay was designed using 96 antigens including most common antigens associated with autoimmune diseases, including, as representative examples, thryoglobulin, C1q, MPO, transglutaminase, Sm/RNP, GAD65, Ro/SSA, JO-1, IA-2, La/SSB, PR3, Sm B/B', CENP-A, U1-snRNP-C, Gliadin, Histone H3, H2B, SmD, Histone H4 and insulin H.

The antigens are first categorized by molecular weight into two groups ("Group A"=molecular weight greater than 9 kDa, and "Group B"=molecular weight less than 9 kDa) for antigen-DNA conjugation.

The various different antigens are each independently conjugated to a unique polynucleotide containing a unique primer binding region and a terminal universal region that has homology to one half of a bridge oligonucleotide. The universal sequence allows the use of the same bridge oligo in the ligation step for all antigens. The two unique primer sites (i.e., one on each polynucleotide joined by the bridging oligo) define the identity of each antigen. Although the described method has immense potential multiplexability and thus is not so limited, in the instantly described embodiment an initial 96-plex format was used in order to comport with convention 96-well qPCR amplification and detection devices.

The antigen-DNA conjugates from Group A are synthesized by using excess of DNA (13 kDa) to drive antigen-DNA conjugate formation. The excess DNA is separated from antigen-DNA conjugates (larger than 22 kDa) by a 20 kDa MWCO filter plate. Group B antigen-DNA conjugates are synthesized by employing an excess of antigens to drive reaction product formation. The free antigens (smaller than 9 kDa) are separated from the antigen-DNA conjugates (at least 13 kDa) by a 10 kDa MWCO filter plate.

As exemplary antigens of Group A and B, respectively, this process will be described for histone H3 (15 kDa) and insulin (5.8 kDa). Briefly, for histone H3, 5 molar equivalent of sulfo-SMCC is incubated with 1 mg of histone H3 for 2 h at RT. At the same time, 100 µM of thiolated-DNA is incubated with DTT for 1h at 37° C. Both the histone and DNA will be separated from unreacted small molecules by desalting plates (e.g., as available from Thermo Fisher Scientific, Inc.). The activated histone and DNA are then incubated overnight at 4° C. Next, the reaction mixtures are aliquoted into a 96-well 20 kDa MWCO filter plate and efficiently separated from unreacted DNA. The purity of product and yield from each individual well of the plate can be validated by electrophoresis and UV-VIS spectroscopy methods.

The insulin-DNA conjugates are similarly prepared using a 10 kDa MWCO cutoff filter plate, with the primary difference being that an excess of antigens is incubated with limited DNA. Thus, the 10 kDa MWCO filter plate is used to remove antigens, rather than DNA as described for histone H3.

The antigen-DNA conjugates can be characterized for conjugation efficiency by 24-well SDS-PAGE electrophoresis and by silver staining, the latter of which allows visualization of all three components: antigen-DNA conjugates, unconjugated antigens, free DNA. Antigen-DNA conjugates can be confirmed by comparing mobility difference using SDS-PAGE to that of pure antigens. The DNA conjugation ratio on antigens can be verified by UV-VIS spectroscopy and BCA assay, where the former reveals information about DNA amounts and the latter informs of the protein concentration. The ratio between the two measurements (with appropriate standards) indicates the conjugation ratio, which, in this embodiment, is targeted to an antigen-to-DNA ratio of 1:2.

Successful antigen-DNA conjugation has been performed over a wide range of antigen molecular weights, including e.g., 9 kDa (insulin), 29 kDa (GFP), 65 kDa (GAD65) and 660 kDa (thyroglobulin). In addition, antigen-DNA conjugates with membrane protein antigens, which generally have increased hydrophobicity, have also been successfully produced (e.g., gp120).

The developed multiplex ADAP assay is validated with human patient serum samples, including those from systemic lupus erythematosus (SLE) and rheumatoid arthritis (RA) patients. The assay contains essential self-antigens that bind antibodies known to be produced in SLE (e.g., histone H2B, Jo-1, Ro-52) and RA patients. The results obtained using the multiplexed ADAP assay and the improved sensitivity can be independently verified against a protein microarray using the same samples.

In the general multiplex assay protocol, 2 µL samples are mixed with 2 µL probes (containing all 96 antigen-DNA conjugates pooled together) for 15 min. Next, 116 µL of ligation mixture (which contains a universal bridge oligo, ligase and buffer) is added. This ligation step is performed at 30° C. for 15 min. The resulting ligation products are aliquoted into a 96-well qPCR plate where unique primer pairs have been preloaded into each well. Quantification is performed in standard qPCR machinery by adding qPCR master mix to a final volume of 20 µL. The whole process requires minimum sample consumption and can be completed in less than 2 h with standard lab instruments.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting a polyclonal antibody in a sample, the method comprising:
   a) contacting the sample with:
      i) a first conjugate comprising a first polynucleotide conjugated to a first molecule of an antigen in a molar ratio of less than 5:1, wherein the antigen comprises more than two different binding sites for the antibody; and
      ii) a second conjugate comprising a second polynucleotide conjugated to a second molecule of the antigen in a molar ratio of less than 5:1,
      wherein said contacting is under conditions sufficient to form an agglutination complex in which the first molecule of the antigen and second molecule of the antigen simultaneously bind two or more molecules of the antibody such that the agglutination complex comprises at least two molecules of the antibody;
   b) binding the first polynucleotide and the second polynucleotide of the complex to form an amplicon; and
   c) detecting the amplicon, wherein detection of the amplicon provides for detection of the polyclonal antibody.

2. The method according to claim 1, wherein the antigen is a polypeptide.

3. The method according to claim 1, wherein the binding comprises ligating the first polynucleotide and the second polynucleotide.

4. The method according to claim 1, wherein the method further comprises contacting the sample with a splint polynucleotide and the binding comprises ligating the splint polynucleotide to the first polynucleotide or the second polynucleotide or both the first and second polynucleotides.

5. The method according to claim 4, wherein the first polynucleotide, second polynucleotide, and splint polynucleotide are DNA polynucleotides and the ligating comprises contacting the sample with a DNA ligase.

6. The method according to claim 1, comprising amplifying the amplicon to generate an amplification product; and detecting the amplification product, wherein detection of the amplification product provides for detection of the polyclonal.

7. The method according to claim 6, wherein the amplifying comprises polymerase chain reaction (PCR) amplification or isothermal amplification.

8. The method according to claim 1, wherein the detecting comprises measuring the amount of the antibody in the sample based on quantifying the amplicon.

9. The method according to claim 1, wherein the sample is obtained from a subject suspected of having anti-polynucleotide antibodies.

10. The method according to claim 1, wherein the sample is obtained from a subject suspected of having a condition.

11. The method according to claim 10, wherein the condition comprises an infection, an autoimmune disorder, an inflammatory disorder, an immune response to a neoplasm, or a metabolic disease.

12. The method according to claim 1, wherein the sample is a tissue sample.

13. The method according to claim 1, wherein the sample is derived from a cell.

14. The method according to claim 1, wherein the sample comprises urine, saliva, cerebrospinal fluid, interstitial fluid, ocular fluid, synovial fluid, blood, plasma, or serum.

15. The method according to claim 1, wherein the polyclonal antibody comprises one or more of an IgG antibody, an IgM antibody, and an IgE antibody.

16. The method according to claim 1, wherein the polyclonal antibody is present in the sample at a concentration of less than 15 ng/ml.

17. The method according to claim 1, wherein the polyclonal antibody is present in the sample at a concentration of less than 100 pg/mL.

18. The method according to claim 1, wherein the polyclonal antibody is present in the sample in a zeptomole to attomole range.

19. The method according to claim 1, wherein the first polynucleotide is conjugated to the first molecule of the antigen in a molar ratio of from 1:1 to 4:1, and wherein the second polynucleotide is conjugated to the second molecule of the antigen in a molar ratio of from 1:1 to 4:1.

20. The method according to claim 1, wherein the method further comprises contacting the sample with a bridging polynucleotide and the binding comprises ligating the bridging polynucleotide to the first polynucleotide or the second polynucleotide or both the first and second polynucleotides.

21. The method according to claim 20, wherein the method further comprises contacting the sample with a splint polynucleotide and the binding comprises ligating the splint polynucleotide to the first polynucleotide or the second polynucleotide or the bridging polynucleotide or any two or all three of the first, second and bridging polynucleotides.

22. A kit for the detection of a polyclonal antibody, the kit comprising:
   a) a first conjugate comprising a first polynucleotide conjugated to a first molecule of an antigen in a molar ratio of less than 5:1, wherein the antigen comprises more than two different binding sites for the antibody; and
   b) a second conjugate comprising a second polynucleotide conjugated to a second molecule of the antigen in a molar ratio of less than 5:1.

* * * * *

SEQUENCE LISTING

<160> NUMBER OF SEQ ID NOS: 13

<210> SEQ ID NO 1
<211> LENGTH: 80
<212> TYPE: DNA
<213> ORGANISM: Artificial sequence
<220> FEATURE:
<223> OTHER INFORMATION: synthetic oligonucleotide

<400> SEQUENCE: 1
ggcctcctcc aattaaagaa tcacgatgag actggatgaa tcacggtagc ataaggtgca    60
gtacccaaat aacggttcac                                                80

<210> SEQ ID NO 2
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 2
caggtagtag tacgtctgtt tcacgatgag actggatgaa                          40

<210> SEQ ID NO 3
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 3
tcacggtagc ataaggtgca agataatact ctcgcagcac                          40

<210> SEQ ID NO 4
<211> LENGTH: 18
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: deoxyribouracil
<220> FEATURE:
<221> NAME/KEY: misc_feature
<222> LOCATION: (7)..(7)
<223> OTHER INFORMATION: deoxyribouracil
<220> FEATURE:
<221> NAME/KEY: misc_feature
<222> LOCATION: (10)..(11)
<223> OTHER INFORMATION: deoxyribouracil
<220> FEATURE:
<221> NAME/KEY: misc_feature
<222> LOCATION: (14)..(14)
<223> OTHER INFORMATION: deoxyribouracil

<400> SEQUENCE: 4
cnaccgngan ncanccag                                                  18

<210> SEQ ID NO 5
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 5
ggcctcctcc aattaaagaa                                                20

<210> SEQ ID NO 6
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 6
gtgaaccgtt atttgggtac                                              20

<210> SEQ ID NO 7
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 7
ggcctcctcc aattaaagaa tcacgatgag actggatgaa                         40

<210> SEQ ID NO 8
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 8
tcacggtagc ataaggtgca gtacccaaat aacggttcac                         40

<210> SEQ ID NO 9
<211> LENGTH: 47
<212> TYPE: DNA
<213> ORGANISM: Artificial sequence
<220> FEATURE:
<223> OTHER INFORMATION: synthetic oligonucleotide

<400> SEQUENCE: 9
tcgtggaact atctagcggt gtacgtgagt gggcatgtag caagagg                 47

<210> SEQ ID NO 10
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 10
gtcatcattc gaatcgtact gcaatcgggt attaggctag tgactactgg tt           52

<210> SEQ ID NO 11
<211> LENGTH: 20
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: deoxyribouracil
<220> FEATURE:
<221> NAME/KEY: misc_feature
<222> LOCATION: (7)..(7)
<223> OTHER INFORMATION: deoxyribouracil
<220> FEATURE:
<221> NAME/KEY: misc_feature
<222> LOCATION: (13)..(13)

```
<223> OTHER INFORMATION: deoxyribouracil
<220> FEATURE:
<221> NAME/KEY: misc_feature
<222> LOCATION: (15)..(16)
<223> OTHER INFORMATION: deoxyribouracil
<220> FEATURE:
<221> NAME/KEY: misc_feature
<222> LOCATION: (19)..(19)
<223> OTHER INFORMATION: deoxyribouracil

<400> SEQUENCE: 11
gaangangac ccncnngcna                                              20

<210> SEQ ID NO 12
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 12
cgtggaacta tctagcggtg ta                                           22

<210> SEQ ID NO 13
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 13
acccgattgc agtacgattc                                              20
```